US012188053B2

(12) United States Patent
Crowe, Jr. et al.

(10) Patent No.: US 12,188,053 B2
(45) Date of Patent: Jan. 7, 2025

(54) HUMAN MONOCLONAL ANTIBODIES THAT NEUTRALIZE PANDEMIC GII.4 NOROVIRUSES

(71) Applicants: Vanderbilt University, Nashville, TN (US); BAYLOR COLLEGE OF MEDICINE, Houston, TX (US)

(72) Inventors: James E. Crowe, Jr., Nashville, TN (US); Mary Estes, Houston, TX (US)

(73) Assignees: VANDERBILT UNIVERSITY, Nashville, TN (US); BAYLOR COLLEGE OF MEDICINE, Houston, TX (US)

(*) Notice: Subject to any disclaimer, the term of this patent is extended or adjusted under 35 U.S.C. 154(b) by 825 days.

(21) Appl. No.: 17/271,843

(22) PCT Filed: Aug. 27, 2019

(86) PCT No.: PCT/US2019/048231
§ 371 (c)(1),
(2) Date: Feb. 26, 2021

(87) PCT Pub. No.: WO2020/046857
PCT Pub. Date: Mar. 5, 2020

(65) Prior Publication Data
US 2021/0324050 A1  Oct. 21, 2021

Related U.S. Application Data

(60) Provisional application No. 62/723,565, filed on Aug. 28, 2018, provisional application No. 62/723,155, filed on Aug. 27, 2018.

(51) Int. Cl.
*C12N 7/00* (2006.01)
*C07K 16/10* (2006.01)
*G01N 33/569* (2006.01)

(52) U.S. Cl.
CPC ............... *C12N 7/00* (2013.01); *C07K 16/10* (2013.01); *G01N 33/56983* (2013.01); *C07K 2317/21* (2013.01); *C07K 2317/33* (2013.01); *C07K 2317/55* (2013.01); *C07K 2317/76* (2013.01); *G01N 2333/08* (2013.01)

(58) Field of Classification Search
None
See application file for complete search history.

(56) References Cited

U.S. PATENT DOCUMENTS

| | | | |
|---|---|---|---|
| 6,610,305 B1 | 8/2003 | Elbers et al. | |
| 9,244,072 B2 | 1/2016 | Miki | |
| 2005/0152911 A1 | 7/2005 | Hardy | |
| 2017/0247434 A1 | 8/2017 | Hansman et al. | |

FOREIGN PATENT DOCUMENTS

| | | |
|---|---|---|
| WO | 2017/011394 | 1/2017 |
| WO | WO-2017011394 A1 * | 1/2017 |
| WO | 2019/057755 | 3/2019 |

OTHER PUBLICATIONS

Horsager-Boehrer. Published Jan. 2, 2018, accessed Jun. 6, 2024 at https://utswmed.org/medblog/gastroenteritis-norovirus-stomach-flu/; Should pregnant moms be concerned about gastroenteritis? 5-page printout. (Year: 2018).*
Alvarado et al., "Human Monoclonal Antibodies That Neutralize Pandemic GII.4 Noroviruses", *Gastroenterology*, 155(6): 1898-1907, 2018.
Atmar et al., "Human noroviruses: recent advances in a 50-year history", *Curr Opin Infect Dis.*, 31(5):422-432, 2018.
Atmar et al., "Serological Correlates of Protection against a GII.4 Norovirus", *Clin Vaccine Immunol.*, 22(8):923-929, 2015.
Crawford et al., "Mapping Broadly Reactive Norovirus Genogroup I and II Monoclonal Antibodies," *Clin. Vaccine Immunol.*, 22:168-177, 2015.
Czako et al., "Experimental Human Infection with Norwalk Virus Elicits a Surrogate Neutralizing Antibody Response with Cross-Genogroup Activity", *Clin Vaccine Immunol.*, 22(2):221-228, 2015.
Debbink et al., "Emergence of New Pandemic GII.4 Sydney Norovirus Strain Correlates With Escape From Herd Immunity", *J Infect Dis.*, 208(11):1877-1887, 2013.
Debbink et al., "Genetic Mapping of a Highly Variable Norovirus GII.4 Blockade Epitope: Potential Role in Escape from Human Herd Immunity", *J Virol.*, 86:1214-1226, 2012.
Huang et al., "Identification of human single-chain antibodies with broad reactivity for noroviruses", *Protein Eng Des Sel.*, 27(10):339-349, 2014.
Koromyslova and Hansman, "Nanobodies targeting norovirus capsid reveal functional epitopes and potential mechanisms of neutralization", *PLoS Pathog.*, 13:e1006636, 2017.
Koromyslova et al., Nanobody Binding to a Conserved Epitope Promotes Norovirus Particle Disassembly, J. Virol., 89(5):2718-2730, 2015.
Lindesmith et al., "Immunogenetic Mechanisms Driving Norovirus GII.4 Antigenic Variation", *PLoS Pathog.*, 8:e1002705, 2012a.
Lindesmith et al., "Monoclonal Antibody-Based Antigenic Mapping of Norovirus GII.4-2002", *J Virol.*, 86(2):873-883, 2012b.
Lochridge et al., "Epitopes in the P2 domain of norovirus VP1 recognized by monoclonal antibodies that block cell interactions", *J Gen Virol.*, 86:2799-2806, 2005.

(Continued)

Primary Examiner — Benjamin P Blumel
Assistant Examiner — Jeffrey Mark Sifford
(74) Attorney, Agent, or Firm — Parker Highlander PLLC

(57) ABSTRACT

The present disclosure is directed to antibodies binding to and neutralizing norovirus and methods for use thereof. Thus, in accordance with the present disclosure, there is provided a method of detecting a norovirus infection in a subject comprising (a) contacting a sample from the subject with an antibody or antibody fragment having clone-paired heavy and light chain CDR sequences; and (b) detecting norovirus in the sample by binding of the antibody or antibody fragment to a norovirus antigen in the sample.

21 Claims, 17 Drawing Sheets
Specification includes a Sequence Listing.

(56) References Cited

OTHER PUBLICATIONS

Parker et al., "Identification of Genogroup I and Genogroup II Broadly Reactive Epitopes on the Norovirus Capsid", *J. Virol.*, 79(12), 7402-7409, 2005.
Parra et al., "Mapping and modeling of a strain-specific epitope in the Norwalk virus capsid inner shell", Virology, 492:232-241, 2016.
PCT International Search Report and Written Opinion issued in International Application No. PCT/US2019/048231, dated Jan. 7, 2020.
Sapparapu et al., "Frequent Use of the IgA Isotype in Human B Cells Encoding Potent Norovirus-Specific Monoclonal Antibodies That Block HBGA Binding," *PLoS Pathog.*, 12:e1005719, 2016.

\* cited by examiner

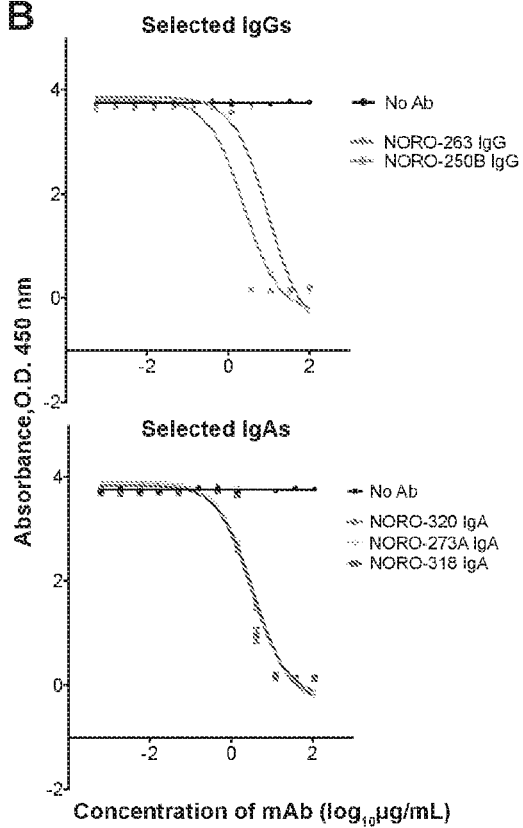
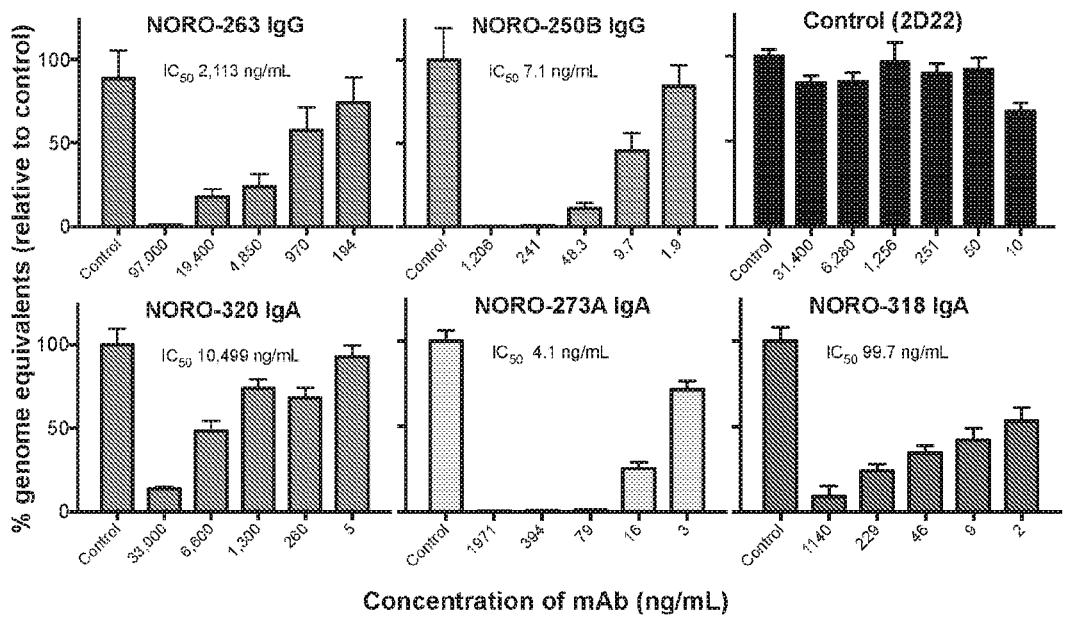
FIGS. 1A-C

| | | | EC$_{50}$ (nM) for binding to protruding or shell domain protein | | | | | | | |
|---|---|---|---|---|---|---|---|---|---|---|
| | | | Genogroup I | | Genogroup II | | | | | |
| | | | GI.3 | | GII.4 | | GII.6 | | GII.17 | |
| Isotype | NORO- | Domain specificity | Protruding | Shell | Protruding | Shell | Protruding | Shell | Protruding | Shell |
| IgM | 155.5 | ND | > | > | > | > | > | > | > | > |
| | 156.3 | ND | > | > | > | > | > | > | > | > |
| | 168.2 | P/S | 143 | 37 | 238 | 78 | 135 | 162 | 390 | 183 |
| | 170.5 | S | > | 385 | > | > | > | 304 | > | 255 |
| IgG | 167.3 | S | > | > | > | 90 | > | > | > | > |
| | 178.6 | P/S | 336 | > | > | 8 | > | > | > | > |
| | 202A.2 | S | > | > | > | 3 | > | > | > | > |
| | 279A | S | > | > | > | 3 | > | > | > | > |
| | 310A | P/S | 60 | > | 219 | 19 | > | > | > | > |
| | 323A | P | 7 | > | 172 | > | > | > | > | > |
| IgA | 232A.2 | P | > | > | 3 | > | 2 | > | 2 | > |
| | 320 | P | > | > | 2 | > | 3 | > | 3 | > |

FIG. 11

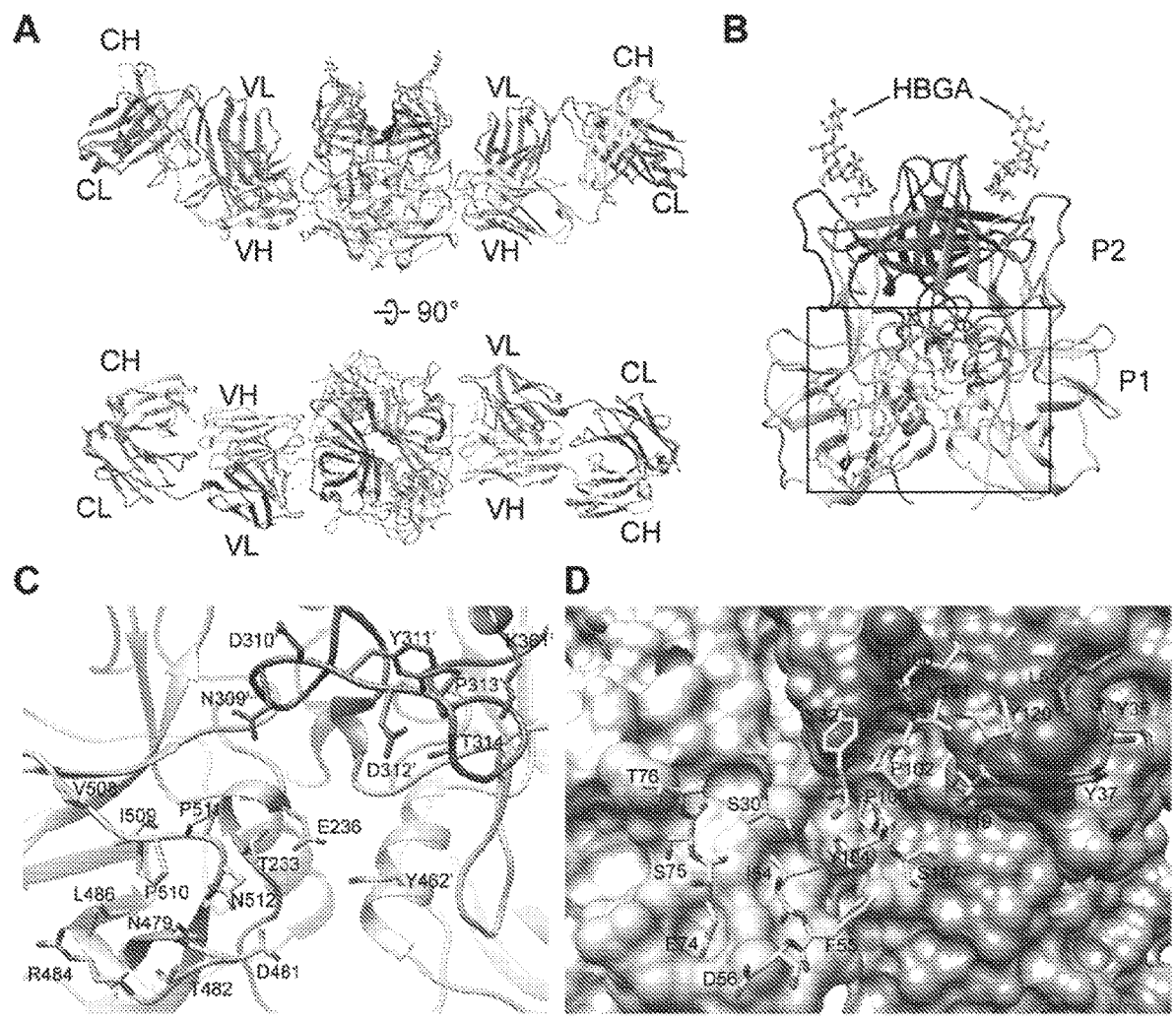
FIGS. 12A-D

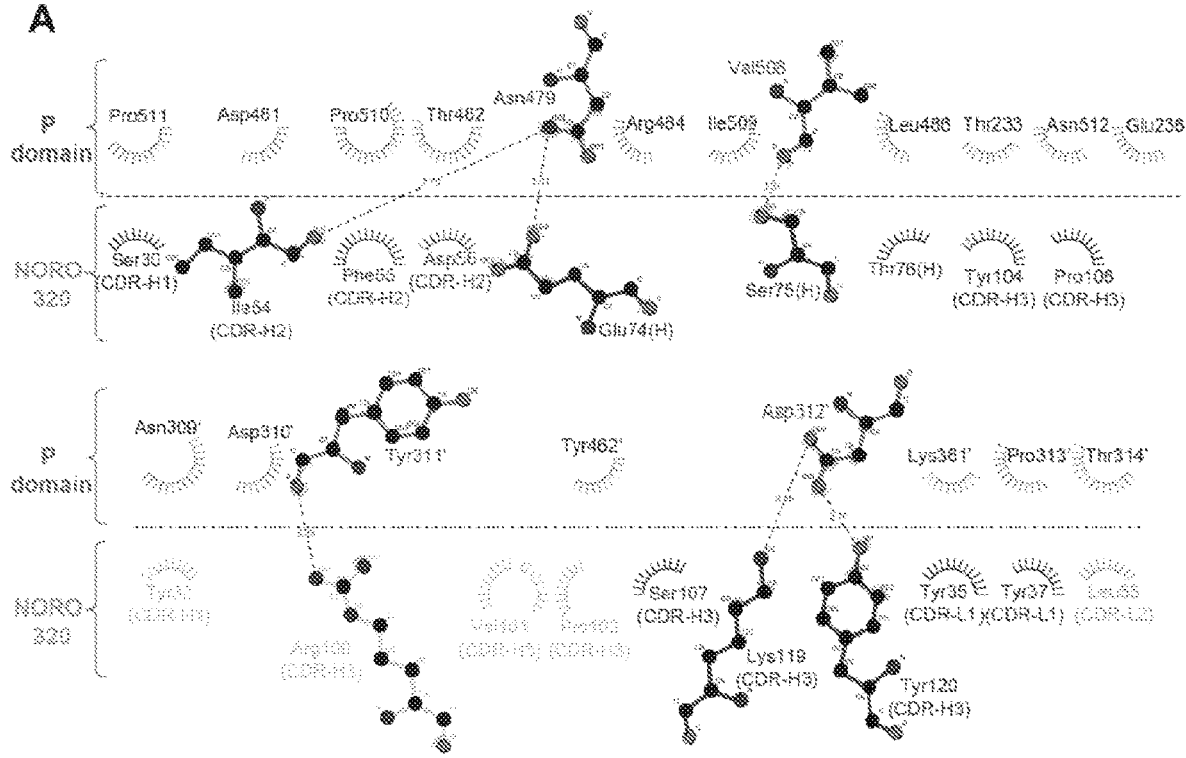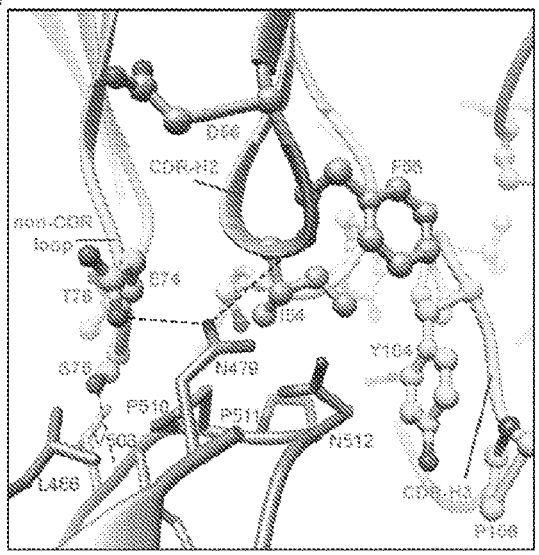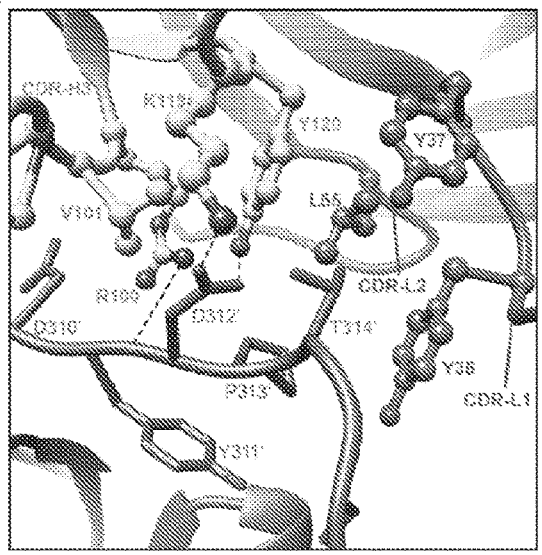
FIGS. 13A-C

FIG. 14

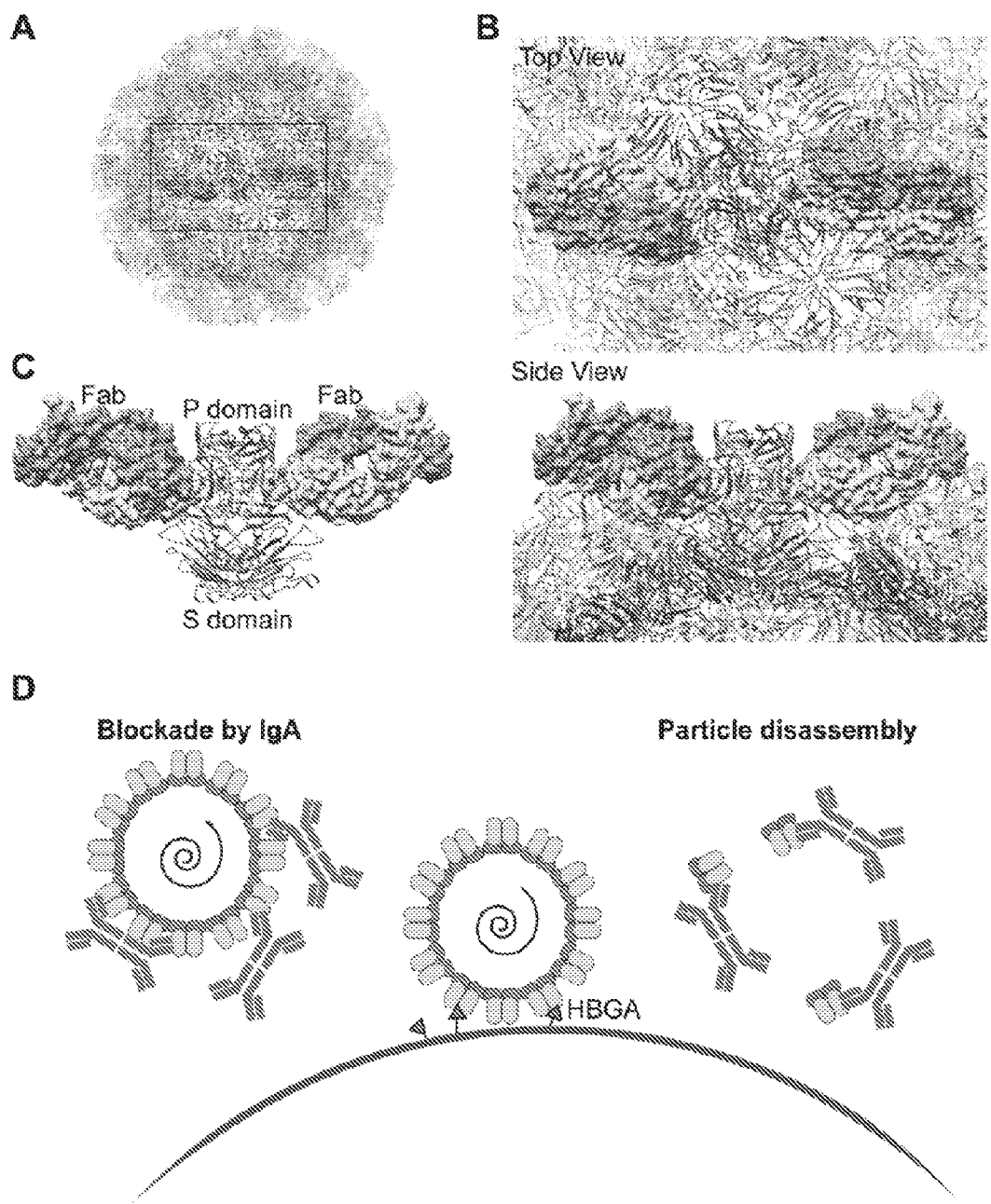
FIGS. 17A-D

SEQUENCE LISTING

```
<160> NUMBER OF SEQ ID NOS: 337

<210> SEQ ID NO 1
<211> LENGTH: 367
<212> TYPE: DNA
<213> ORGANISM: Artificial sequence
<220> FEATURE:
<223> OTHER INFORMATION: Synthetic oligonucleotide

<400> SEQUENCE: 1
caggtgcagc tggtggagtc tggggagc ttggtcaagc ctgggggtc cctgagactc      60 tcctgtacag cctctggaat caccatcagt ggctactaca tgagttggat ccgccaggct    120
ccagggaagg gactggaatg gattgtatac attaatacaa gtggtagaac catatactac   180
gcagactctg tgaagggccg gttctccgtc tccagggaca acgccaagga gtcgctgtat   240
ttgcaaatgg acagcctgac ggtcgatgac acgggcatat attattgtgc gagagatcga   300
ttaccagcat ctggttccca ctggttccac ccctgggcc agggaaccct ggtcaccgtc   360
tcctcag                                                             367

<210> SEQ ID NO 2
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 2
gacatcgtga tgacccagtc tccagactcc ctggctgtgt ctctgggcgg gagggccacc    60
atcaactgca agtccagcca gagtgtttta tacacctccg acaataagaa ctacttagcc    120
```

```
tggtaccagc agcaaccagg acagcctcct aagctgctca tttcctgggc ttctactcgg    180
gaatccgggg tccctgaccg attcagtggc agcgggtctg ggacagattt cactctcacc    240
atcagcaacc tgcaggctga agatgtggca gtttattact gtcagcagta ttataatagt    300
cctctcgctt cggcggagg gaccaaggtg gagatcaaa                             339

<210> SEQ ID NO 3
<211> LENGTH: 393
<212> TYPE: DNA
<213> ORGANISM: Artificial sequence
<220> FEATURE:
<223> OTHER INFORMATION: Synthetic oligonucleotide

<400> SEQUENCE: 3
caggtgcagc tggtggagtc tgggggaggc gtggtccagc ctgggaggtc cctgagactc     60
tcctgttcaa cctctggatt caccttcagt caatatccta tgcactgggt ccgccaggct    120
ccaggcaagg ggctggagtg ggtggcactt atatcctatg atggaatgaa taaatactac    180
gcagactccg tgaggggccg attcaccatc tccagagaca attccgagaa cacgcagtat    240
ctgcaaatga acagcctgag aggtgacgac acggctgtct attattgtgc gagagtcacg    300
ggcgattgta ctggtaatag atgctcatat tgggcatact actactacgg tctggacgtc    360
tggggccaag ggaccctggt caccgtctcc tca                                  393

<210> SEQ ID NO 4
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 4
cagtctgccc tgactcagcc tccctccgcg tccgggtctc ctggacagtc agtcaccatc     60
tcctgcactg gaaccagtag tgacgttggt ggttataagt atgtctcctg gtaccaacag    120
cacccaggca agcccccaa actcatgatt tatgaggtca ctaggcgcc ctcaggggtc      180 cctgatcgct tctctggctc caagtctggc aacacggcct cctgaccgt ctctgggctc    240 caggctgagg atgaggctga ttattactgc ggctcatatg caggcagcac cacttccggg    300
tatgtcttcg gaactgggac caaggtcatc gtccta                               336

<210> SEQ ID NO 5
<211> LENGTH: 367
<212> TYPE: DNA
<213> ORGANISM: Artificial sequence
<220> FEATURE:
<223> OTHER INFORMATION: Synthetic oligonucleotide

<400> SEQUENCE: 5
caggtgcagt tggtgcagtc tggggctgag gtgaagaagc ctggggcctc agtgaaggtc     60
tcctgcaagg cttctgaata cacctttacc ggctactatt tgcagtgggt gcgacaggcc    120
cctggacatg ggcttgaatg gatgggatgg atcaatccca gtggtggcac aaagtattca    180
cagaagtttc agggcagggt caccatgacc agggacacgt ccatcactac tgtctacatg    240
gaactgagca gactgagatc tgacgacacg gccgtctatt actgtgcgag agaccttctt    300
aggaactggg gtgatcatga tgcttttgat gtctggggcc aggggacaat ggtcaccgtc    360
tcctcag                                                               367
```

<210> SEQ ID NO 6
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 6

```
cagtctgtgc tgactcagcc accctcagcg tctgagaccc ccgggcaggg ggtcaccatc      60
tcttgttctg gaagcagctc caacatcgga agtaattttg tatgctggta ccagcaggtc     120
ccaggaacgg cccccaaact cctcatctat aagaataatc agcggccctc agggtccct     180 gaccgattct ctggctccaa gtctggcacc tcagcctccc tggccatcag tgggctccgg     240
tccgaggatg aggctgatta ttactgttca gcatgggatg acagcctgag tggtccggta     300
ttcggcggag ggaccaagct gaccgtccta g                                     331
```

<210> SEQ ID NO 7
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 7

```
caggtgcagc tggtggagtc tgggggaggc ttggtcaagc ctggagggtc cctgacactc      60
tcctgtgcag cctctggatt caccttcagt gactactaca tgaactggat ccgccaggct     120
ccagggaaga gactggagtg ggtttcatac attagtggta ttatgagttc cacaaactac     180
gcagactctg tgaagggccg attcaccatc tccagagaca ccgccaagaa gtcagtgtat     240
ctgcaaatga acagcctgag agccgaggat acggctgtgt attactgtgc gagagcaacc     300
tcacagggag ctacctctta ctactttgac tcctggggcc agggaaccct ggtcaccgtc     360
tcctca                                                                 366
```

<210> SEQ ID NO 8
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 8

```
cagtctgtgc tgacgcagcc gccctcagtg tctggggccc cagggcagag ggtcaccatc      60
tcctgcactg ggagcagctc caacatcggg gcagattatg atgttcactg gtaccaacaa     120
cttccaggag cagcccccag actcctcatc tatgctgaca tcaatcggcc ctcaggggtc     180
cctgatcgat tctctggctc caagtctggc acctcagcct ccctggccat cactgggctc     240
caggctgagg atgaggctga ttattactgc caatcctatg acagaagcgt gagtggttcg     300
gcggtgttcg gcggagggac caaggtgacc gtccta                                336
```

<210> SEQ ID NO 9
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 9

```
caggtgcagc tggtggagtc tgggggaggc gtggtccagc ctggagggtc cctgagactc      60
```

```
tcctgtgcag cctctggatt caccttcagg agctatggca ttcactgggt ccgccaggct    120
ccaggcaagg ggctggagtg ggtggcactt atatcatatg atggaagtag taaatactat    180
gcagactcag tgaagggccg attcaccatc tccagagaca attccaagaa cacgttgtat    240
ctgcaaatga acagcctgag aagtgaggac acggctgtgt attactgtgc gaaagtgagg    300
ttgacaagtt atagcattgg ctggttttcc tttgactact ggggccaggg taccctggtc    360
accgtctcct ca                                                        372

<210> SEQ ID NO 10
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 10
caggtgcagc tggtggagtc tgggggaggc gtggtccagc ctgggaggtc cctgagactc     60
tcctgtgcag cctctggatt caccttcagg agctatggca ttcactgggt ccgccaggct    120
ccaggcaagg ggctggagtg ggtggcactt atatcatatg atggaagtag taaatactat    180
gcagactcag tgaagggccg attcaccatc tccagagaca attccaagaa cacgttgtat    240
ctgcaaatga acagcctgag aagtgaggac acggctgtgt attactgtgc gaaagtgagg    300
ttgacaagtt atagcattgg ctggttttcc tttgactact ggggccaggg taccctggtc    360
accgtctcct ca                                                        372

<210> SEQ ID NO 11
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 11
caggtgcagc tggtggagtc tgggggaggc gtggtccagg ctgggaggtc cctgagactc     60
tcctgtgcag cctctggatt caccttcaga agttatggca tgcactgggt ccgccaggct    120
ccaggcaagg ggctggagtg ggtggcaatt atatcatatg atggaggtag taaatattat    180
gcagactccg tgaagggccg attcaccatc tccagagaca attccaagaa cacgttgtat    240
ctgcaaatga acagcctgag agttgaggac acggctctat attactgtgc gaaagatttt    300
ttacgtgtat acagttatgg ttggcactct tttgatattt ggggcctagg gaccctggtc    360
accgtctcct ca                                                        372

<210> SEQ ID NO 12
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 12
cagtctgtgt tgacgcagcc gccctcagtg tctgcggccc caggacagag ggtcaccatc     60
tcctgctctg gaagcagctc caacattggg acttattatg tctcctggta ccagcatctc    120
ccaggaacag cccccaaact cctcatttat gacaatgata agcgaccctc agggattcct    180
gaccgattct ctgcctccaa gtctggcacg tcagccaccc tggacatcgc cggactccaa    240
```

```
actggggacg aggccgatta ttactgcgga acatgggatc tcagcctgac tgctggctgg    300
gtgttcggcg gagggaccaa gttgaccgtc cta                                 333
```

<210> SEQ ID NO 13
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 13

```
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gaaagttacc   300
attatagcag cagctgattt gcttgactac tggggccagg gaaccctggt caccgtctcc   360
tca                                                                 363
```

<210> SEQ ID NO 14
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 14

```
cagtctgtgc tgacgcagcc gccctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtggtccg   300
gtggtattcg gcggagggac caagctgacc gtccta                             336
```

<210> SEQ ID NO 15
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 15

```
caggtgcagc tggtggagtc tgggggaggc gtggtccagc ctgggaggtc cctgagactc    60
tcctgcgcag cctctggatt caccttcaca aaatatggca tgcactgggt ccgccaggct   120
ccaggcaagg ggctggagtg ggtggctttt atagcatatg atggaagtgt taaatattat   180
ggagactccg cgaagggccg attcgccatt tccagagaca tcccaagaa tacagtatat    240 ctgcaaatga acagcctgag agcagaagac acggctgtat attattgtgc gaaagtggag   300
atacactatt attcgaatag tctcttaggt atggacgtct ggggccaagg gaccctggtc   360
accgtctcct ca                                                       372
```

<210> SEQ ID NO 16
<211> LENGTH: 327
<212> TYPE: DNA
<213> ORGANISM: Artificial sequence

```
<220> FEATURE:
<223> OTHER INFORMATION: Synthetic oligonucleotide

<400> SEQUENCE: 16
cagtctgtgc tgactcagcc accctcagcg tctgggaccc ccgggcagag ggtcaccatc      60
tcttgttctg gaggcaactc caacatcgga attagttatg tgtactggta ccagcatctc     120
ccaggaacgg cccccaaact cctcatatct aaaaataatc tgcggccctc agggqtccct     180 gaccgattct ctgcctccaa gtctggcact tcagcctccc tggccatcag tggactccgg     240
tccgaggatg aggctgaata ttactgtgca acattggata tcaatatgac ctgggtattc     300
ggcggaggga ccaagctgac cgtccta                                          327

<210> SEQ ID NO 17
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 17
caggtgcagc tggtggagtc tgggggaggc ttggtcaagc ctggagggtc cctgagactc      60
tcctgtgcag cctctggatt caccttcagt gagtactaca tgagctgggt ccgccaggct     120
ccagggaagg cgctggagtg ggtttcatac attactagta gtttcagttc acaagctat     180 gcagactctg tgaagggccg attcgtcatc tccagagaca acgccaagaa ctcactgtat     240
ctacaaatga acagcctgag agtcgaggac acggccgtgt attactgtgc gagatatggc     300
gcggagtatg gttcgcggag tttctacttc ctggactggg gccagggcac cctggtcacc     360
gtctcctca                                                              369

<210> SEQ ID NO 18
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 18
cagtctgtgc tgacgcagcc gccctcagtg tctggggccc cagagcagag ggtcaccatc      60
tcctgcactg ggagcagctc caacatcggg gcaggttatg atgtacactg gtaccaggtg     120
cttccaggaa tagcccccaa actcctcatc tacgataaca acaagcggcc ctcaggggtc     180
cctgaccgat tctctggctc caagtctggc acctcagcct ccctggccat cactgggctc     240
caggctgagg atgaggctga ttattactgc cagtcctatg acagcaggct gagtagcaat     300
gtggtattcg gcggagggac caaactgacc gtcctg                                336

<210> SEQ ID NO 19
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 19
caggtgcagc tggtggagtc tgggggaggc gtggtccagc ctggagggtc cctgagactc      60
tcctgtgcag cctctggatt catcttcagt agctatgcta tgcactgggt ccgccaggct     120
ccaggcaagg ggctagagtg ggtggcagtt atgtcatatg atggaaataa taatactac     180
```

```
gcagactccg tgaagggccg attcaccatc tccagagaca attccaagaa cacgctgttt      240
ctgcaaatga acagcctgag acctgaggac acggccgtgt attattgtgc gagagattgt      300
cgagtcgggt gggtattcac ctacggtatg gacgtctggg gccaagggac cctggtcacc      360
gtctcctca                                                              369

<210> SEQ ID NO 20
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 20
cagtctgccc tgactcagcc tccctccgcg tccgggtctc ctggacagtc agtcaccatc      60
tcctgcactg gaaccagcag tgacgttggt ggttataact atgtctcctg gtaccaacag      120
cacccaggca aagcccccaa actcatgatt tatgagatca gtaagcggcc ctcaggggtc      180
cctattcgct tctctggctc caagtctggc aacacggcct ccctgaccgt ctctgggctc      240
caggctgagg atgaggctga ttattactgc agctcatatg caggcaccta caactgtgtg      300
gtattcggcg gagggaccaa gctgaccgtc cta                                   333

<210> SEQ ID NO 21
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 21
gaggtgcagc tggtggagtc tgggggaggc ttggtccggc ctggggagtc cctgagactc      60
tcctgtgtag cctctggatt cagcgtcagt gacaactaca tgagctgggt ccgccaggct      120
ccagggaagg gactgcagtg gtctccgtt atttatagcg gtggtactac attctacaca      180
gactccgtga agggcagatt caccatctcc agagacaagt ccaagaacac gctgtttctt      240
caaatgaaca gcctgagagc cgaggacacg gctgtgtatt tctgtacgcg agatccatcg      300
caatactatg atagtcgtgg tcattactac cagactttca ctccctcctt tgactcctgg      360
ggccagggaa ccctggtcac cgtctcctca                                       390

<210> SEQ ID NO 22
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 22
gacatccaga tgacccagtc tccatctgtc atgtctgcat ctgtaggaga cagagtcacc      60
atcacttgtc gggcgagtca ggacattagc gattatttag cctggtttca gcagaagcca      120
gggaaagtcc ctaagcgcct gatctatgct gcatccagtt tgcaaaatgg ggtcccatca      180
aggttcagcg gcagtggatc tgggacagaa ttcactctca caatcagcag cctgcagcct      240
gaagattttg caacttatta ctgtctacag catgatactt accctctcac tttcggcgga      300
gggaccaagg tggagatcaa a                                                321

<210> SEQ ID NO 23
<211> LENGTH: 375
```

```
<212> TYPE: DNA
<213> ORGANISM: Artificial sequence
<220> FEATURE:
<223> OTHER INFORMATION: Synthetic oligonucleotide

<400> SEQUENCE: 23
caggtgcagc tggtggagtc tgggggagcc ttggtcaagc ctggagagtc cctgagactc      60
tcctgtgcag cctctggatt caccttcagt gactcctaca tgagctggat ccgccaggct     120
ccagggaagg gactggagtg ggttgcatac attagtggta tcatgagttc cacaaaactac    180 gcagattctg tgaaaggccg attcaccatc tccagagaca acggcaagaa ctcagtgtat     240
ctgcaaatga acaacctgag agccgaggac acggctgtgt actactgtgc aagagatgcc     300
caatattgca gtggcggtag gtgctacttg gtatttgact actggggcca gggaaccctg     360
gtcaccgtct cctca                                                      375

<210> SEQ ID NO 24
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 24
cagtctgtgc tgacgcagcc gccctcagtg tctggggccc caggacagag ggtcaccatc      60
tcttgcactg ggagcagctc caacatcggg gcaggttatg aagtacactg gtaccagcaa     120
cttccaggag cagcccccaa actcatcatc tatggtaaca acaatcggcc ctcaggggtc     180
cctgaccgat tctctggctc caagtctggc acctcagcct ccctggccat cactgggctc     240
caggctgacg atgaggctga ttattactgc cagtcttatg acaacaggct aagggtattc     300
ggcgggggga ccaagctgac cgtccta                                         327

<210> SEQ ID NO 25
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 25
caggtgcagc tggtggagtc tgggggaggc ttggtcaagc ctggagggtc cctgagactc      60
tcctgtgcag cctctggatt caccttcagt gacttctaca tgagctggat ccgccaggct     120
ccagggaagg gctggagtg ggttgggtac attagctcta ttgctggtgc cacaaattac      180
gcagactctg tgaagggccg attcaccatc tccagagaca gctccaagag gtcactgtat     240
ctgcaaatga acagcctgag agtcgaggac acggctgtat actactgtgc gagaatgggg    300
cgcttagagc tggagcgacg gccccattat tactaccctt tggacgtctg gggccaaggg    360
accctggtca ccgtctcctc a                                              381

<210> SEQ ID NO 26
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 26
gatattgtga tgacccagtc tccactctcc ctgcccgtca cccctggaga gccggcctcc      60
```

```
atctcctgca ggtctagtca gagcctcctg catagtaatg gatacaacta tttggattgg    120
tacttgcaga agccagggca gtctccacag ctcctgatct ttttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcgg    300
acttttggcc aggggaccaa gctggagatc aaa                                  333

<210> SEQ ID NO 27
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 27
caggtgcagc tggtggagtc tgggggaggc ttggtcaagc ctggagggtc cctgagactc     60
tcctgtgtgg cctctggatt caccttcagc gactactaca tgacctggtt ccgccagact    120
ccagggaggg ggctggagtg gctttcatac attagtgcta tcggaggtta cacagaatac    180
gcagactctg tgaagagccg attcatcatc tctagagaca acggcaagaa atcactgtat    240
cttcaaatga acagcctcag agccgaggac tccggtgtct attactgtgc gagagaagat    300
tgtcatggta ctagttgcta ctcgggcgac tggggccagg gaaccctggt caccgtctcc    360
tca                                                                   363

<210> SEQ ID NO 28
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 28
cagtctgtgc tgacgcagcc gccctcagtg tctggggccc cagggcagag ggtcaccatc     60
tcctgcactg ggagcagctc caacatcggg gcaggttatg atgtacactg gtaccagcag    120
cttccaggaa cagcccccaa actcctcatc tatcataaca ccaatcggcc ctcgggggtc    180
cctgaccgat tctctggctc caagtctggc acctcagcct acctgaccat cactgggctc    240
caggctgagg atgaggctga ttattactgc cagtcatatg acagaagcct cagtaaatcg    300
agggtgttca gcggagggac caagctgacc gtccta                               336

<210> SEQ ID NO 29
<211> LENGTH: 393
<212> TYPE: DNA
<213> ORGANISM: Artificial sequence
<220> FEATURE:
<223> OTHER INFORMATION: Synthetic oligonucleotide

<400> SEQUENCE: 29
caggtgcagc tggtggagtc tgggggaggc ttggtcaagc ctggagggtc cctgagactc     60
tcctgtgtag catctggatt caccttcagt gactactaca tcagctgggt ccgccaggct    120
ccagggaagg ggctggagtg ggtttcatac attagtgcta ttaatagtta tacaaactat    180
gcagactctg tgaggggccg attcaccgtc tccagagaca acgccaagaa gtcagtcttt    240
ttgcaaatga atagcctgag agtcgacgac acggctgtgt attattgtgc gagagatgtc    300
ggcggctcgt tcggtatag cagcaactcg aacaaaaaat cctacaacta cttcgacccc    360
tggggccagg gaaccctggt caccgtctcc tca                                  393
```

<210> SEQ ID NO 30
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 30

```
tcctatgagc tgacacagcc accctcggtg tcagtgtccc caggacagac ggccacgatc    60
acctgctcgg gagatgtttt gtcaaaggag tttgcttatt ggtaccagca gaagccaggc   120
caggcccctg tgttggtgat atataaagac aatgagaggc cctcaggat acctgagcga    180 ttctctggct ccacctcagg gacaacagtc acgttgacca tcagtggagt cctggcagaa   240
gacgaggctc actattattg tcaatcagta gacaccaggg gcacttataa agtgttcggc   300
ggagggacca agctgaccgt ccta                                          324
```

<210> SEQ ID NO 31
<211> LENGTH: 405
<212> TYPE: DNA
<213> ORGANISM: Artificial sequence
<220> FEATURE:
<223> OTHER INFORMATION: Synthetic oligonucleotide

<400> SEQUENCE: 31

```
caggtgcagc tggtgcagtc tgggcctgag gtgaagaagc ctgggtcctc ggtgaaggtc    60
tcctgcaagg cttctggagg caccgtcagc agctatgcta tcagctgggt gcgacaggcc   120
cctggacaag ggcttgagtg gatgggaggg atcatcccca tctttgatac aacaaactac   180
gcacagaaat tccagggcag agttacgatt accgcggacg aatccacggg cacaagcgac   240
atggaactga gcagccttag atctgaggac acggccgtgt attactgtgc gagagatcgc   300
gtcccgtctt attctccttc gcggaggttt tccactaagg gggcgatgtg gggaaaatac   360
ggtatggacg tctggggcca agggaccctg gtcaccgtct cctca                   405
```

<210> SEQ ID NO 32
<211> LENGTH: 336
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (69)..(69)
<223> OTHER INFORMATION: n is a, c, g, or t

<400> SEQUENCE: 32

```
gatattgtga tgactcagtc tccactctcc ctgcccgtca cccctggaga gccggcctcc    60
atctcctgna ggtctagtca gagcctcctg catagtaatg gatacaacta tttggattgg   120
tacctgcaga agccagggca gtctccacag ctcctgatct atttggttc taatcgggcc    180 tccggggtcc ctgacaggtt cagtggcagt ggatcaggca cagatttac actgaaaatc    240 agcaaagtgg aggctgagga tgttggggtt tattactgca tgcaagctct acaaactcct   300
cggacgttcg gccaagggac caaggtggaa atcaaa                             336
```

<210> SEQ ID NO 33
<211> LENGTH: 366
<212> TYPE: DNA
<213> ORGANISM: Artificial sequence
<220> FEATURE:

<223> OTHER INFORMATION: Synthetic oligonucleotide

<400> SEQUENCE: 33

```
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg gatttcatat attagcagta gttttggttc cacagactac     180
gcaggctcta tgaagggccg attcaccatc tccagagaca cgccaagaa ttcactgtat      240
ctgcaaatga acagcctgag agccgaggac acggctgtgt attactgtgc gagatacaat     300
tactatggtt cggggagttt cgtctttgac tactggggcc aggggaccct ggtcaccgtc     360
tcctca                                                                366
```

<210> SEQ ID NO 34
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 34

```
cagtctgtgg cgactcagcc accctcagcg tctgggaccc ccgggcagag ggtcaccatc      60
tcttgttctg ggagcagctc caacatcgga agtaatactg taagctggta ccagcaactc     120
ccaggaacgg cccccaaact cctcatttat agtaatgatc agcggccctc agggggtcct    180
ggccgattct ctggctccaa gtctggcacc tcagcctccc tggccatcag tgggctccag     240
tctgaggatg aggtgattta tcctgtgca gcatgggatg acagcctgaa tggttgggtg      300
ttcggcggag ggaccaagct gaccgtccta                                      330
```

<210> SEQ ID NO 35
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 35

```
Gln Val Gln Leu Val Glu Ser Gly Gly Gly Leu Val Lys Pro Gly
  1               5                  10                  15
Ser Leu Arg Leu Ser Cys Thr Ala Ser Gly Ile Thr Ile Ser Gly Tyr
             20                  25                  30
Tyr Met Ser Trp Ile Arg Gln Ala Pro Gly Lys Gly Leu Glu Trp Ile
         35                  40                  45
Val Tyr Ile Asn Thr Ser Gly Arg Thr Ile Tyr Tyr Ala Asp Ser Val
     50                  55                  60
Lys Gly Arg Phe Ser Val Ser Arg Asp Asn Ala Lys Glu Ser Leu Tyr
 65                  70                  75                  80
Leu Gln Met Asp Ser Leu Thr Val Asp Asp Thr Gly Ile Tyr Tyr Cys
                 85                  90                  95
Ala Arg Asp Arg Leu Pro Ala Ser Gly Ser His Trp Phe His Pro Trp
            100                 105                 110
Gly Gln Gly Thr Leu Val Thr Val Ser Ser
        115                 120
```

<210> SEQ ID NO 36
<211> LENGTH: 113
<212> TYPE: PRT
<213> ORGANISM: Artificial sequence

```
<220> FEATURE:
<223> OTHER INFORMATION: Synthetic polypeptide

<400> SEQUENCE: 36

Asp Ile Val Met Thr Gln Ser Pro Asp Ser Leu Ala Val Ser Leu Gly
1               5                   10                  15

Gly Arg Ala Thr Ile Asn Cys Lys Ser Ser Gln Ser Val Leu Tyr Thr
                20                  25                  30

Ser Asp Asn Lys Asn Tyr Leu Ala Trp Tyr Gln Gln Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Asn Leu Gln Ala Glu Asp Val Ala Val Tyr Tyr Cys Gln Gln
                85                  90                  95

Tyr Tyr Asn Ser Pro Leu Ala Phe Gly Gly Gly Thr Lys Val Glu Ile
            100                 105                 110

Lys

<210> SEQ ID NO 37
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ser Thr Ser Gly Phe Thr Phe Ser Gln Tyr
                20                  25                  30

Pro Met His Trp Val Arg Gln Ala Pro Gly Lys Gly Leu Glu Trp Val
            35                  40                  45

Ala Leu Ile Ser Tyr Asp Gly Met Asn Lys Tyr Tyr Ala Asp Ser Val
    50                  55                  60

Arg Gly Arg Phe Thr Ile Ser Arg Asp Asn Ser Glu Asn Thr Gln Tyr
65                  70                  75                  80

Leu Gln Met Asn Ser Leu Arg Gly Asp Asp Thr Ala Val Tyr Tyr Cys
                85                  90                  95

Ala Arg Val Thr Gly Asp Cys Thr Gly Asn Arg Cys Ser Tyr Trp Ala
            100                 105                 110

Tyr Tyr Tyr Tyr Gly Leu Asp Val Trp Gly Gln Gly Thr Leu Val Thr
        115                 120                 125

Val Ser Ser
    130

<210> SEQ ID NO 38
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 38

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
```

```
                20                  25                  30
Lys Tyr Val Ser Trp Tyr Gln Gln His Pro Gly Lys Ala Pro Lys Leu
            35                  40                  45

Met Ile Tyr Glu Val Thr Arg Arg Pro Ser Gly Val Pro Asp Arg Phe
    50                  55                  60

Ser Gly Ser Lys Ser Gly Asn Thr Ala Phe Leu Thr Val Ser Gly Leu
65                  70                  75                  80

Gln Ala Glu Asp Glu Ala Asp Tyr Tyr Cys Gly Ser Tyr Ala Gly Ser
                85                  90                  95

Thr Thr Ser Gly Tyr Val Phe Gly Thr Gly Thr Lys Val Ile Val Leu
            100                 105                 110

<210> SEQ ID NO 39
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Glu Tyr Thr Phe Thr Gly Tyr
            20                  25                  30

Tyr Leu Gln Trp Val Arg Gln Ala Pro Gly His Gly Leu Glu Trp Met
        35                  40                  45

Gly Trp Ile Asn Pro Ser Gly Gly Thr Lys Tyr Ser Gln Lys Phe Gln
    50                  55                  60

Gly Arg Val Thr Met Thr Arg Asp Thr Ser Ile Thr Thr Val Tyr Met
65                  70                  75                  80

Glu Leu Ser Arg Leu Arg Ser Asp Asp Thr Ala Val Tyr Tyr Cys Ala
                85                  90                  95

Arg Asp Leu Leu Arg Asn Trp Gly Asp His Asp Ala Phe Asp Val Trp
            100                 105                 110

Gly Gln Gly Thr Met Val Thr Val Ser Ser
        115                 120

<210> SEQ ID NO 40
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 40

Gln Ser Val Leu Thr Gln Pro Pro Ser Ala Ser Glu Thr Pro Gly Gln
1               5                   10                  15

Gly Val Thr Ile Ser Cys Ser Gly Ser Ser Ser Asn Ile Gly Ser Asn
            20                  25                  30

Phe Val Cys Trp Tyr Gln Gln Val Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ala Trp Asp Asp Ser Leu
                85                  90                  95
```

Ser Gly Pro Val Phe Gly Gly Thr Lys Leu Thr Val Leu
            100                 105                 110

<210> SEQ ID NO 41
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 41

Gln Val Gln Leu Val Glu Ser Gly Gly Gly Leu Val Lys Pro Gly Gly
1               5                   10                  15

Ser Leu Thr Leu Ser Cys Ala Ala Ser Gly Phe Thr Phe Ser Asp Tyr
            20                  25                  30

Tyr Met Asn Trp Ile Arg Gln Ala Pro Gly Lys Arg Leu Glu Trp Val
        35                  40                  45

Ser Tyr Ile Ser Gly Ile Met Ser Ser Thr Asn Tyr Ala Asp Ser Val
    50                  55                  60

Lys Gly Arg Phe Thr Ile Ser Arg Asp Thr Ala Lys Lys Ser Val Tyr
65                  70                  75                  80

Leu Gln Met Asn Ser Leu Arg Ala Glu Asp Thr Ala Val Tyr Tyr Cys
                85                  90                  95

Ala Arg Ala Thr Ser Gln Gly Ala Thr Ser Tyr Tyr Phe Asp Ser Trp
            100                 105                 110

Gly Gln Gly Thr Leu Val Thr Val Ser Ser
            115                 120

<210> SEQ ID NO 42
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 42

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Asp
            20                  25                  30

Tyr Asp Val His Trp Tyr Gln Gln Leu Pro Gly Ala Ala Pro Arg Leu
        35                  40                  45

Leu Ile Tyr Ala Asp Ile Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Arg Ser
                85                  90                  95

Val Ser Gly Ser Ala Val Phe Gly Gly Gly Thr Lys Val Thr Val Leu
            100                 105                 110

<210> SEQ ID NO 43
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 43

Gln Val Gln Leu Val Glu Ser Gly Gly Gly Val Val Gln Pro Gly Arg

-continued

```
                1               5                   10                  15
            Ser Leu Arg Leu Ser Cys Ala Ala Ser Gly Phe Thr Phe Arg Ser Tyr
                            20                  25                  30

Gly Ile His Trp Val Arg Gln Ala Pro Gly Lys Gly Leu Glu Trp Val
                            35                  40                  45

Ala Leu Ile Ser Tyr Asp Gly Ser Ser Lys Tyr Tyr Ala Asp Ser Val
                            50                  55                  60

Lys Gly Arg Phe Thr Ile Ser Arg Asp Asn Ser Lys Asn Thr Leu Tyr
             65                 70                  75                  80

Leu Gln Met Asn Ser Leu Arg Ser Glu Asp Thr Ala Val Tyr Tyr Cys
                            85                  90                  95

Ala Lys Val Arg Leu Thr Ser Tyr Ser Ile Gly Trp Phe Ser Phe Asp
                            100                 105                 110

Tyr Trp Gly Gln Gly Thr Leu Val Thr Val Ser Ser
                            115                 120
```

<210> SEQ ID NO 44
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 44

```
            Gln Ser Val Leu Thr Gln Pro Pro Ser Val Ser Ala Ala Pro Gly Gln
             1              5                   10                  15

Lys Val Thr Ile Ser Cys Ser Gly Ser Ser Ser Asn Ile Ala Asn Tyr
                            20                  25                  30

Tyr Val Ser Trp Tyr Gln Gln Leu Pro Gly Arg Ala Pro Lys Leu Leu
                            35                  40                  45

Ile Tyr Asp Asn Asn Lys Arg Pro Ser Gly Ile Pro Asp Arg Ile Ser
                            50                  55                  60

Gly Ser Lys Ser Gly Thr Ser Ala Thr Leu Gly Ile Thr Gly Leu Gln
             65                 70                  75                  80

Thr Gly Asp Glu Ala Asp Tyr Tyr Cys Gly Thr Trp Asp Thr Ser Leu
                            85                  90                  95

Ser Ala Trp Val Phe Gly Gly Gly Thr Lys Leu Thr Val Leu
                            100                 105                 110
```

<210> SEQ ID NO 45
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 45

```
            Gln Val Gln Leu Val Glu Ser Gly Gly Gly Val Val Gln Ala Gly Arg
             1              5                   10                  15

Ser Leu Arg Leu Ser Cys Ala Ala Ser Gly Phe Thr Phe Arg Ser Tyr
                            20                  25                  30

Gly Met His Trp Val Arg Gln Ala Pro Gly Lys Gly Leu Glu Trp Val
                            35                  40                  45

Ala Ile Ile Ser Tyr Asp Gly Ser Lys Tyr Tyr Ala Asp Ser Val
                            50                  55                  60

Lys Gly Arg Phe Thr Ile Ser Arg Asp Asn Ser Lys Asn Thr Leu Tyr
             65                 70                  75                  80
```

-continued

Leu Gln Met Asn Ser Leu Arg Val Glu Asp Thr Ala Leu Tyr Tyr Cys
                85                  90                  95

Ala Lys Asp Phe Leu Arg Val Tyr Ser Tyr Gly Trp His Ser Phe Asp
            100                 105                 110

Ile Trp Gly Leu Gly Thr Leu Val Thr Val Ser Ser
        115                 120

<210> SEQ ID NO 46
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 46

Gln Ser Val Leu Thr Gln Pro Pro Ser Val Ser Ala Ala Pro Gly Gln
1               5                   10                  15

Arg Val Thr Ile Ser Cys Ser Gly Ser Ser Ser Asn Ile Gly Thr Tyr
            20                  25                  30

Tyr Val Ser Trp Tyr Gln His Leu Pro Gly Thr Ala Pro Lys Leu Leu
        35                  40                  45

Ile Tyr Asp Asn Asp Lys Arg Pro Ser Gly Ile Pro Asp Arg Phe Ser
    50                  55                  60

Ala Ser Lys Ser Gly Thr Ser Ala Thr Leu Asp Ile Ala Gly Leu Gln
65                  70                  75                  80

Thr Gly Asp Glu Ala Asp Tyr Tyr Cys Gly Thr Trp Asp Leu Ser Leu
                85                  90                  95

Thr Ala Gly Trp Val Phe Gly Gly Gly Thr Lys Leu Thr Val Leu
            100                 105                 110

<210> SEQ ID NO 47
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 47

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Thr Ile Ile Ala Ala Ala Asp Leu Leu Asp Tyr Trp Gly
            100                 105                 110

Gln Gly Thr Leu Val Thr Val Ser Ser
        115                 120

<210> SEQ ID NO 48
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 48

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Pro Val Val Phe Gly Gly Gly Thr Lys Leu Thr Val Leu
            100                 105                 110

<210> SEQ ID NO 49
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 49

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Lys Tyr
            20                  25                  30

Gly Met His Trp Val Arg Gln Ala Pro Gly Lys Gly Leu Glu Trp Val
        35                  40                  45

Ala Phe Ile Ala Tyr Asp Gly Ser Val Lys Tyr Tyr Gly Asp Ser Ala
    50                  55                  60

Lys Gly Arg Phe Ala Ile Ser Arg Asp Asn Pro Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Val Glu Ile His Tyr Tyr Ser Asn Ser Leu Leu Gly Met Asp
            100                 105                 110

Val Trp Gly Gln Gly Thr Leu Val Thr Val Ser Ser
        115                 120

<210> SEQ ID NO 50
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 50

Gln Ser Val Leu Thr Gln Pro Pro Ser Ala Ser Gly Thr Pro Gly Gln
1               5                   10                  15

Arg Val Thr Ile Ser Cys Ser Gly Gly Asn Ser Asn Ile Gly Ile Ser
            20                  25                  30

Tyr Val Tyr Trp Tyr Gln His Leu Pro Gly Thr Ala Pro Lys Leu Leu
        35                  40                  45

```
Ile Ser Lys Asn Asn Leu Arg Pro Ser Gly Val Pro Asp Arg Phe Ser
    50                  55                  60

Ala Ser Lys Ser Gly Thr Ser Ala Ser Leu Ala Ile Ser Gly Leu Arg
65                  70                  75                  80

Ser Glu Asp Glu Ala Glu Tyr Tyr Cys Ala Thr Leu Asp Ile Asn Met
                85                  90                  95

Thr Trp Val Phe Gly Gly Gly Thr Lys Leu Thr Val Leu
                100                 105
```

<210> SEQ ID NO 51
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 51

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Glu Tyr
                20                  25                  30

Tyr Met Ser Trp Val Arg Gln Ala Pro Gly Lys Ala Leu Glu Trp Val
            35                  40                  45

Ser Tyr Ile Thr Ser Ser Phe Ser Ser Thr Ser Tyr Ala Asp Ser Val
    50                  55                  60

Lys Gly Arg Phe Val Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Tyr Gly Ala Glu Tyr Gly Ser Arg Ser Phe Tyr Phe Leu Asp
                100                 105                 110

Trp Gly Gln Gly Thr Leu Val Thr Val Ser Ser
            115                 120
```

<210> SEQ ID NO 52
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 52

```
Gln Ser Val Leu Thr Gln Pro Pro Ser Val Ser Gly Ala Pro Glu Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Val Leu Pro Gly Ile Ala Pro Lys Leu
            35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Arg
                85                  90                  95

Leu Ser Ser Asn Val Val Phe Gly Gly Gly Thr Lys Leu Thr Val Leu
                100                 105                 110
```

<210> SEQ ID NO 53

```
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 53

Gln Val Gln Leu Val Glu Ser Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Lys Gly Leu Glu Trp Val
        35                  40                  45

Ala Val Met Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Pro Glu Asp Thr Ala Val Tyr Tyr Cys
                85                  90                  95

Ala Arg Asp Cys Arg Val Gly Trp Val Phe Thr Tyr Gly Met Asp Val
            100                 105                 110

Trp Gly Gln Gly Thr Leu Val Thr Val Ser Ser
        115                 120

<210> SEQ ID NO 54
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 54

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Met Tyr Glu Ile Ser Lys Arg Pro Ser Gly Val Pro Ile Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Thr
                85                  90                  95

Tyr Asn Cys Val Val Phe Gly Gly Gly Thr Lys Leu Thr Val Leu
            100                 105                 110

<210> SEQ ID NO 55
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 55

Glu Val Gln Leu Val Glu Ser Gly Gly Gly Leu Val Arg Pro Gly Glu
1               5                   10                  15

Ser Leu Arg Leu Ser Cys Val Ala Ser Gly Phe Ser Val Ser Asp Asn
            20                  25                  30
```

```
Tyr Met Ser Trp Val Arg Gln Ala Pro Gly Lys Gly Leu Gln Trp Val
             35                  40                  45

Ser Val Ile Tyr Ser Gly Gly Thr Thr Phe Tyr Thr Asp Ser Val Lys
 50                  55                  60

Gly Arg Phe Thr Ile Ser Arg Asp Lys Ser Lys Asn Thr Leu Phe Leu
 65                  70                  75                  80

Gln Met Asn Ser Leu Arg Ala Glu Asp Thr Ala Val Tyr Phe Cys Thr
                 85                  90                  95

Arg Asp Pro Ser Gln Tyr Tyr Asp Ser Arg Gly His Tyr Tyr Gln Thr
                100                 105                 110

Phe Thr Pro Ser Phe Asp Ser Trp Gly Gln Gly Thr Leu Val Thr Val
            115                 120                 125

Ser Ser
130

<210> SEQ ID NO 56
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 56

Asp Ile Gln Met Thr Gln Ser Pro Ser Val Met Ser Ala Ser Val Gly
 1               5                  10                  15

Asp Arg Val Thr Ile Thr Cys Arg Ala Ser Gln Asp Ile Ser Asp Tyr
             20                  25                  30

Leu Ala Trp Phe Gln Gln Lys Pro Gly Lys Val Pro Lys Arg Leu Ile
         35                  40                  45

Tyr Ala Ala Ser Ser Leu Gln Asn Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asp Thr Tyr Pro Leu
                 85                  90                  95

Thr Phe Gly Gly Gly Thr Lys Val Glu Ile Lys
            100                 105

<210> SEQ ID NO 57
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 57

Gln Val Gln Leu Val Glu Ser Gly Gly Ala Leu Val Lys Pro Gly Glu
 1               5                  10                  15

Ser Leu Arg Leu Ser Cys Ala Ala Ser Gly Phe Thr Phe Ser Asp Ser
             20                  25                  30

Tyr Met Ser Trp Ile Arg Gln Ala Pro Gly Lys Gly Leu Glu Trp Val
         35                  40                  45

Ala Tyr Ile Ser Gly Ile Met Ser Ser Thr Asn Tyr Ala Asp Ser Val
 50                  55                  60

Lys Gly Arg Phe Thr Ile Ser Arg Asp Asn Gly Lys Asn Ser Val Tyr
 65                  70                  75                  80

Leu Gln Met Asn Asn Leu Arg Ala Glu Asp Thr Ala Val Tyr Tyr Cys
                 85                  90                  95
```

Ala Arg Asp Ala Gln Tyr Cys Ser Gly Gly Arg Cys Tyr Leu Val Phe
            100                 105                 110

Asp Tyr Trp Gly Gln Gly Thr Leu Val Thr Val Ser Ser
            115                 120                 125

<210> SEQ ID NO 58
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 58

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Glu Val His Trp Tyr Gln Gln Leu Pro Gly Ala Ala Pro Lys Leu
            35                  40                  45

Ile Ile Tyr Gly Asn Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Asp Asp Glu Ala Asp Tyr Tyr Cys Gln Ser Tyr Asp Asn Arg
            85                  90                  95

Leu Arg Val Phe Gly Gly Gly Thr Lys Leu Thr Val Leu
            100                 105

<210> SEQ ID NO 59
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 59

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
            20                  25                  30

Tyr Met Ser Trp Ile Arg Gln Ala Pro Gly Lys Gly Leu Glu Trp Val
            35                  40                  45

Gly Tyr Ile Ser Ser Ile Ala Gly Ala Thr Asn Tyr Ala Asp Ser Val
50                  55                  60

Lys Gly Arg Phe Thr Ile Ser Arg Asp Ser Ser Lys Arg Ser Leu Tyr
65                  70                  75                  80

Leu Gln Met Asn Ser Leu Arg Val Glu Asp Thr Ala Val Tyr Tyr Cys
            85                  90                  95

Ala Arg Met Gly Arg Leu Glu Leu Glu Arg Pro His Tyr Tyr Tyr
            100                 105                 110

Pro Leu Asp Val Trp Gly Gln Gly Thr Leu Val Thr Val Ser Ser
            115                 120                 125

<210> SEQ ID NO 60
<211> LENGTH: 111
<212> TYPE: PRT
<213> ORGANISM: Artificial sequence
<220> FEATURE:
<223> OTHER INFORMATION: Synthetic polypeptide

```
<400> SEQUENCE: 60

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Phe Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Arg Thr Phe Gly Gln Gly Thr Lys Leu Glu Ile Lys
            100                 105                 110

<210> SEQ ID NO 61
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 61

Gln Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Thr Trp Phe Arg Gln Thr Pro Gly Arg Gly Leu Glu Trp Leu
        35                  40                  45

Ser Tyr Ile Ser Ala Ile Gly Gly Tyr Thr Glu Tyr Ala Asp Ser Val
    50                  55                  60

Lys Ser Arg Phe Ile Ile Ser Arg Asp Asn Gly Lys Lys Ser Leu Tyr
65                  70                  75                  80

Leu Gln Met Asn Ser Leu Arg Ala Glu Asp Ser Gly Val Tyr Tyr Cys
                85                  90                  95

Ala Arg Glu Asp Cys His Gly Thr Ser Cys Tyr Ser Gly Asp Trp Gly
            100                 105                 110

Gln Gly Thr Leu Val Thr Val Ser Ser
        115                 120

<210> SEQ ID NO 62
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 62

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr His Asn Thr Asn Arg Pro Ser Gly Val Pro Asp Arg Phe
    50                  55                  60
```

```
Ser Gly Ser Lys Ser Gly Thr Ser Ala Tyr Leu Thr Ile Thr Gly Leu
 65                  70                  75                  80

Gln Ala Glu Asp Glu Ala Asp Tyr Tyr Cys Gln Ser Tyr Asp Arg Ser
                 85                  90                  95

Leu Ser Lys Ser Arg Val Phe Ser Gly Gly Thr Lys Leu Thr Val Leu
            100                 105                 110

<210> SEQ ID NO 63
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 63

Gln Val Gln Leu Val Glu Ser Gly Gly Gly Leu Val Lys Pro Gly Gly
  1               5                  10                  15

Ser Leu Arg Leu Ser Cys Val Ala Ser Gly Phe Thr Phe Ser Asp Tyr
                 20                  25                  30

Tyr Ile Ser Trp Val Arg Gln Ala Pro Gly Lys Gly Leu Glu Trp Val
             35                  40                  45

Ser Tyr Ile Ser Ala Ile Asn Ser Tyr Thr Asn Tyr Ala Asp Ser Val
 50                  55                  60

Arg Gly Arg Phe Thr Val Ser Arg Asp Asn Ala Lys Lys Ser Val Phe
 65                  70                  75                  80

Leu Gln Met Asn Ser Leu Arg Val Asp Asp Thr Ala Val Tyr Tyr Cys
                 85                  90                  95

Ala Arg Asp Val Gly Ser Val Arg Tyr Ser Ser Asn Ser Asn Lys
                100                 105                 110

Lys Ser Tyr Asn Tyr Phe Asp Pro Trp Gly Gln Gly Thr Leu Val Thr
            115                 120                 125

Val Ser Ser
    130

<210> SEQ ID NO 64
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 64

Ser Tyr Glu Leu Thr Gln Pro Pro Ser Val Ser Val Ser Pro Gly Gln
  1               5                  10                  15

Thr Ala Thr Ile Thr Cys Ser Gly Asp Val Leu Ser Lys Glu Phe Ala
                 20                  25                  30

Tyr Trp Tyr Gln Gln Lys Pro Gly Gln Ala Pro Val Leu Val Ile Tyr
             35                  40                  45

Lys Asp Asn Glu Arg Pro Ser Gly Ile Pro Glu Arg Phe Ser Gly Ser
 50                  55                  60

Thr Ser Gly Thr Thr Val Thr Leu Thr Ile Ser Gly Val Leu Ala Glu
 65                  70                  75                  80

Asp Glu Ala His Tyr Tyr Cys Gln Ser Val Asp Thr Arg Gly Thr Tyr
                 85                  90                  95

Lys Val Phe Gly Gly Gly Thr Lys Leu Thr Val Leu
            100                 105
```

```
<210> SEQ ID NO 65
<211> LENGTH: 135
<212> TYPE: PRT
<213> ORGANISM: Artificial sequence
<220> FEATURE:
<223> OTHER INFORMATION: Synthetic polypeptide

<400> SEQUENCE: 65

Gln Val Gln Leu Val Gln Ser Gly Pro Glu Val Lys Pro Gly Ser
1               5                   10                  15

Ser Val Lys Val Ser Cys Lys Ala Gly Gly Thr Val Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Asp Thr Thr Asn Tyr Ala Gln Lys Phe
50                  55                  60

Gln Gly Arg Val Thr Ile Thr Ala Asp Glu Ser Thr Gly Thr Ser Asp
65                  70                  75                  80

Met Glu Leu Ser Ser Leu Arg Ser Glu Asp Thr Ala Val Tyr Tyr Cys
                85                  90                  95

Ala Arg Asp Arg Val Pro Ser Tyr Ser Pro Ser Arg Arg Phe Ser Thr
            100                 105                 110

Lys Gly Ala Met Trp Gly Lys Tyr Gly Met Asp Val Trp Gly Gln Gly
        115                 120                 125

Thr Leu Val Thr Val Ser Ser
        130                 135

<210> SEQ ID NO 66
<211> LENGTH: 112
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 66

Asp Ile Val Met Thr Gln Ser Pro Leu Ser Leu Pro Val Thr Pro Gly
1               5                   10                  15

Glu Pro Ala Ser Ile Ser Xaa Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Lys Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

<210> SEQ ID NO 67
<211> LENGTH: 122
<212> TYPE: PRT
<213> ORGANISM: Artificial sequence
<220> FEATURE:
<223> OTHER INFORMATION: Synthetic polypeptide
```

<400> SEQUENCE: 67

Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Tyr Met Ser Trp Ile Arg Gln Ala Pro Gly Lys Gly Leu Glu Trp Ile
        35                  40                  45
Ser Tyr Ile Ser Ser Ser Phe Gly Ser Thr Asp Tyr Ala Gly Ser Met
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Tyr Asn Tyr Tyr Gly Ser Gly Ser Phe Val Phe Asp Tyr Trp
            100                 105                 110
Gly Gln Gly Thr Leu Val Thr Val Ser Ser
        115                 120

<210> SEQ ID NO 68
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 68

Gln Ser Val Ala Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Thr Val Ser Trp Tyr Gln Gln Leu Pro Gly Thr Ala Pro Lys Leu Leu
        35                  40                  45
Ile Tyr Ser Asn Asp Gln Arg Pro Ser Gly Val Pro Gly Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Gly Asp Tyr Ser Cys Ala Ala Trp Asp Asp Ser Leu
                85                  90                  95
Asn Gly Trp Val Phe Gly Gly Gly Thr Lys Leu Thr Val Leu
            100                 105                 110

<210> SEQ ID NO 69
<211> LENGTH: 8
<212> TYPE: PRT
<213> ORGANISM: Artificial sequence
<220> FEATURE:
<223> OTHER INFORMATION: Synthetic peptide

<400> SEQUENCE: 69

Gly Ile Thr Ile Ser Gly Tyr Tyr
1               5

<210> SEQ ID NO 70
<211> LENGTH: 8
<212> TYPE: PRT
<213> ORGANISM: Artificial sequence
<220> FEATURE:
<223> OTHER INFORMATION: Synthetic peptide

<400> SEQUENCE: 70

```
Ile Asn Thr Ser Gly Arg Thr Ile
1               5
```

<210> SEQ ID NO 71
<211> LENGTH: 15
<212> TYPE: PRT
<213> ORGANISM: Artificial sequence
<220> FEATURE:
<223> OTHER INFORMATION: Synthetic peptide

<400> SEQUENCE: 71

```
Ala Arg Asp Arg Leu Pro Ala Ser Gly Ser His Trp Phe His Pro
1               5                   10                  15
```

<210> SEQ ID NO 72
<211> LENGTH: 8
<212> TYPE: PRT
<213> ORGANISM: Artificial sequence
<220> FEATURE:
<223> OTHER INFORMATION: Synthetic peptide

<400> SEQUENCE: 72

```
Gly Phe Thr Phe Ser Gln Tyr Pro
1               5
```

<210> SEQ ID NO 73
<211> LENGTH: 8
<212> TYPE: PRT
<213> ORGANISM: Artificial sequence
<220> FEATURE:
<223> OTHER INFORMATION: Synthetic peptide

<400> SEQUENCE: 73

```
Ile Ser Tyr Asp Gly Met Asn Lys
1               5
```

<210> SEQ ID NO 74
<211> LENGTH: 24
<212> TYPE: PRT
<213> ORGANISM: Artificial sequence
<220> FEATURE:
<223> OTHER INFORMATION: Synthetic peptide

<400> SEQUENCE: 74

```
Ala Arg Val Thr Gly Asp Cys Thr Gly Asn Arg Cys Ser Tyr Trp Ala
1               5                   10                  15

Tyr Tyr Tyr Tyr Gly Leu Asp Val
                20
```

<210> SEQ ID NO 75
<211> LENGTH: 8
<212> TYPE: PRT
<213> ORGANISM: Artificial sequence
<220> FEATURE:
<223> OTHER INFORMATION: Synthetic peptide

<400> SEQUENCE: 75

```
Glu Tyr Thr Phe Thr Gly Tyr Tyr
1               5
```

<210> SEQ ID NO 76
<211> LENGTH: 7
<212> TYPE: PRT
<213> ORGANISM: Artificial sequence
<220> FEATURE:
<223> OTHER INFORMATION: Synthetic peptide

<400> SEQUENCE: 76

Ile Asn Pro Ser Gly Gly Thr
1               5

<210> SEQ ID NO 77
<211> LENGTH: 16
<212> TYPE: PRT
<213> ORGANISM: Artificial sequence
<220> FEATURE:
<223> OTHER INFORMATION: Synthetic peptide

<400> SEQUENCE: 77

Ala Arg Asp Leu Leu Arg Asn Trp Gly Asp His Asp Ala Phe Asp Val
1               5                   10                  15

<210> SEQ ID NO 78
<211> LENGTH: 8
<212> TYPE: PRT
<213> ORGANISM: Artificial sequence
<220> FEATURE:
<223> OTHER INFORMATION: Synthetic peptide

<400> SEQUENCE: 78

Gly Phe Thr Phe Ser Asp Tyr Tyr
1               5

<210> SEQ ID NO 79
<211> LENGTH: 8
<212> TYPE: PRT
<213> ORGANISM: Artificial sequence
<220> FEATURE:
<223> OTHER INFORMATION: Synthetic peptide

<400> SEQUENCE: 79

Ile Ser Gly Ile Met Ser Ser Thr
1               5

<210> SEQ ID NO 80
<211> LENGTH: 15
<212> TYPE: PRT
<213> ORGANISM: Artificial sequence
<220> FEATURE:
<223> OTHER INFORMATION: Synthetic peptide

<400> SEQUENCE: 80

Ala Arg Ala Thr Ser Gln Gly Ala Thr Ser Tyr Tyr Phe Asp Ser
1               5                   10                  15

<210> SEQ ID NO 81
<211> LENGTH: 8
<212> TYPE: PRT
<213> ORGANISM: Artificial sequence
<220> FEATURE:
<223> OTHER INFORMATION: Synthetic peptide

<400> SEQUENCE: 81

Gly Phe Thr Phe Arg Ser Tyr Gly
1               5

<210> SEQ ID NO 82
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 82

Ile Ser Tyr Asp Gly Ser Ser Lys
1               5

<210> SEQ ID NO 83
<211> LENGTH: 17
<212> TYPE: PRT
<213> ORGANISM: Artificial sequence
<220> FEATURE:
<223> OTHER INFORMATION: Synthetic peptide

<400> SEQUENCE: 83

Ala Lys Val Arg Leu Thr Ser Tyr Ser Ile Gly Trp Phe Ser Phe Asp
1               5                   10                  15

Tyr

<210> SEQ ID NO 84
<211> LENGTH: 8
<212> TYPE: PRT
<213> ORGANISM: Artificial sequence
<220> FEATURE:
<223> OTHER INFORMATION: Synthetic peptide

<400> SEQUENCE: 84

Gly Phe Thr Phe Arg Ser Tyr Gly
1               5

<210> SEQ ID NO 85
<211> LENGTH: 8
<212> TYPE: PRT
<213> ORGANISM: Artificial sequence
<220> FEATURE:
<223> OTHER INFORMATION: Synthetic peptide

<400> SEQUENCE: 85

Ile Ser Tyr Asp Gly Gly Ser Lys
1               5

<210> SEQ ID NO 86
<211> LENGTH: 17
<212> TYPE: PRT
<213> ORGANISM: Artificial sequence
<220> FEATURE:
<223> OTHER INFORMATION: Synthetic peptide

<400> SEQUENCE: 86

Ala Lys Asp Phe Leu Arg Val Tyr Ser Tyr Gly Trp His Ser Phe Asp
1               5                   10                  15

Ile

<210> SEQ ID NO 87
<211> LENGTH: 8
<212> TYPE: PRT
<213> ORGANISM: Artificial sequence
<220> FEATURE:
<223> OTHER INFORMATION: Synthetic peptide

<400> SEQUENCE: 87

Gly Phe Thr Phe Ser Ser Tyr Gly
1               5

<210> SEQ ID NO 88
<211> LENGTH: 8
<212> TYPE: PRT
<213> ORGANISM: Artificial sequence
```

```
<220> FEATURE:
<223> OTHER INFORMATION: Synthetic peptide

<400> SEQUENCE: 88

Ile Ser Tyr Asp Gly Ser Asn Lys
1               5

<210> SEQ ID NO 89
<211> LENGTH: 14
<212> TYPE: PRT
<213> ORGANISM: Artificial sequence
<220> FEATURE:
<223> OTHER INFORMATION: Synthetic peptide

<400> SEQUENCE: 89

Ala Lys Val Thr Ile Ile Ala Ala Ala Asp Leu Leu Asp Tyr
1               5                   10

<210> SEQ ID NO 90
<211> LENGTH: 8
<212> TYPE: PRT
<213> ORGANISM: Artificial sequence
<220> FEATURE:
<223> OTHER INFORMATION: Synthetic peptide

<400> SEQUENCE: 90

Gly Phe Thr Phe Thr Lys Tyr Gly
1               5

<210> SEQ ID NO 91
<211> LENGTH: 8
<212> TYPE: PRT
<213> ORGANISM: Artificial sequence
<220> FEATURE:
<223> OTHER INFORMATION: Synthetic peptide

<400> SEQUENCE: 91

Ile Ala Tyr Asp Gly Ser Val Lys
1               5

<210> SEQ ID NO 92
<211> LENGTH: 17
<212> TYPE: PRT
<213> ORGANISM: Artificial sequence
<220> FEATURE:
<223> OTHER INFORMATION: Synthetic peptide

<400> SEQUENCE: 92

Ala Lys Val Glu Ile His Tyr Tyr Ser Asn Ser Leu Leu Gly Met Asp
1               5                   10                  15

Val

<210> SEQ ID NO 93
<211> LENGTH: 8
<212> TYPE: PRT
<213> ORGANISM: Artificial sequence
<220> FEATURE:
<223> OTHER INFORMATION: Synthetic peptide

<400> SEQUENCE: 93

Gly Phe Thr Phe Ser Glu Tyr Tyr
1               5

<210> SEQ ID NO 94
<211> LENGTH: 8
<212> TYPE: PRT
```

```
<213> ORGANISM: Artificial sequence
<220> FEATURE:
<223> OTHER INFORMATION: Synthetic peptide

<400> SEQUENCE: 94

Ile Thr Ser Ser Phe Ser Ser Thr
1               5

<210> SEQ ID NO 95
<211> LENGTH: 16
<212> TYPE: PRT
<213> ORGANISM: Artificial sequence
<220> FEATURE:
<223> OTHER INFORMATION: Synthetic peptide

<400> SEQUENCE: 95

Ala Arg Tyr Gly Ala Glu Tyr Gly Ser Arg Ser Phe Tyr Phe Leu Asp
1               5                   10                  15

<210> SEQ ID NO 96
<211> LENGTH: 8
<212> TYPE: PRT
<213> ORGANISM: Artificial sequence
<220> FEATURE:
<223> OTHER INFORMATION: Synthetic peptide

<400> SEQUENCE: 96

Gly Phe Ile Phe Ser Ser Tyr Ala
1               5

<210> SEQ ID NO 97
<211> LENGTH: 8
<212> TYPE: PRT
<213> ORGANISM: Artificial sequence
<220> FEATURE:
<223> OTHER INFORMATION: Synthetic peptide

<400> SEQUENCE: 97

Met Ser Tyr Asp Gly Asn Asn Lys
1               5

<210> SEQ ID NO 98
<211> LENGTH: 16
<212> TYPE: PRT
<213> ORGANISM: Artificial sequence
<220> FEATURE:
<223> OTHER INFORMATION: Synthetic peptide

<400> SEQUENCE: 98

Ala Arg Asp Cys Arg Val Gly Trp Val Phe Thr Tyr Gly Met Asp Val
1               5                   10                  15

<210> SEQ ID NO 99
<211> LENGTH: 8
<212> TYPE: PRT
<213> ORGANISM: Artificial sequence
<220> FEATURE:
<223> OTHER INFORMATION: Synthetic peptide

<400> SEQUENCE: 99

Gly Phe Ser Val Ser Asp Asn Tyr
1               5

<210> SEQ ID NO 100
<211> LENGTH: 7
<212> TYPE: PRT
<213> ORGANISM: Artificial sequence
```

```
<220> FEATURE:
<223> OTHER INFORMATION: Synthetic peptide

<400> SEQUENCE: 100

Ile Tyr Ser Gly Gly Thr Thr
1               5

<210> SEQ ID NO 101
<211> LENGTH: 24
<212> TYPE: PRT
<213> ORGANISM: Artificial sequence
<220> FEATURE:
<223> OTHER INFORMATION: Synthetic peptide

<400> SEQUENCE: 101

Thr Arg Asp Pro Ser Gln Tyr Tyr Asp Ser Arg Gly His Tyr Tyr Gln
1               5                   10                  15

Thr Phe Thr Pro Ser Phe Asp Ser
            20

<210> SEQ ID NO 102
<211> LENGTH: 8
<212> TYPE: PRT
<213> ORGANISM: Artificial sequence
<220> FEATURE:
<223> OTHER INFORMATION: Synthetic peptide

<400> SEQUENCE: 102

Gly Phe Thr Phe Ser Asp Ser Tyr
1               5

<210> SEQ ID NO 103
<211> LENGTH: 8
<212> TYPE: PRT
<213> ORGANISM: Artificial sequence
<220> FEATURE:
<223> OTHER INFORMATION: Synthetic peptide

<400> SEQUENCE: 103

Ile Ser Gly Ile Met Ser Ser Thr
1               5

<210> SEQ ID NO 104
<211> LENGTH: 18
<212> TYPE: PRT
<213> ORGANISM: Artificial sequence
<220> FEATURE:
<223> OTHER INFORMATION: Synthetic peptide

<400> SEQUENCE: 104

Ala Arg Asp Ala Gln Tyr Cys Ser Gly Gly Arg Cys Tyr Leu Val Phe
1               5                   10                  15

Asp Tyr

<210> SEQ ID NO 105
<211> LENGTH: 8
<212> TYPE: PRT
<213> ORGANISM: Artificial sequence
<220> FEATURE:
<223> OTHER INFORMATION: Synthetic peptide

<400> SEQUENCE: 105

Gly Phe Thr Phe Ser Asp Phe Tyr
1               5
```

```
<210> SEQ ID NO 106
<211> LENGTH: 8
<212> TYPE: PRT
<213> ORGANISM: Artificial sequence
<220> FEATURE:
<223> OTHER INFORMATION: Synthetic peptide

<400> SEQUENCE: 106

Ile Ser Ser Ile Ala Gly Ala Thr
1               5

<210> SEQ ID NO 107
<211> LENGTH: 20
<212> TYPE: PRT
<213> ORGANISM: Artificial sequence
<220> FEATURE:
<223> OTHER INFORMATION: Synthetic peptide

<400> SEQUENCE: 107

Ala Arg Met Gly Arg Leu Glu Leu Glu Arg Pro His Tyr Tyr Tyr
1               5                   10                  15

Pro Leu Asp Val
            20

<210> SEQ ID NO 108
<211> LENGTH: 8
<212> TYPE: PRT
<213> ORGANISM: Artificial sequence
<220> FEATURE:
<223> OTHER INFORMATION: Synthetic peptide

<400> SEQUENCE: 108

Gly Phe Thr Phe Ser Asp Tyr Tyr
1               5

<210> SEQ ID NO 109
<211> LENGTH: 8
<212> TYPE: PRT
<213> ORGANISM: Artificial sequence
<220> FEATURE:
<223> OTHER INFORMATION: Synthetic peptide

<400> SEQUENCE: 109

Ile Ser Ala Ile Gly Gly Tyr Thr
1               5

<210> SEQ ID NO 110
<211> LENGTH: 14
<212> TYPE: PRT
<213> ORGANISM: Artificial sequence
<220> FEATURE:
<223> OTHER INFORMATION: Synthetic peptide

<400> SEQUENCE: 110

Ala Arg Glu Asp Cys His Gly Thr Ser Cys Tyr Ser Gly Asp
1               5                   10

<210> SEQ ID NO 111
<211> LENGTH: 8
<212> TYPE: PRT
<213> ORGANISM: Artificial sequence
<220> FEATURE:
<223> OTHER INFORMATION: Synthetic peptide

<400> SEQUENCE: 111

Gly Phe Thr Phe Ser Asp Tyr Tyr
1               5
```

<210> SEQ ID NO 112
<211> LENGTH: 8
<212> TYPE: PRT
<213> ORGANISM: Artificial sequence
<220> FEATURE:
<223> OTHER INFORMATION: Synthetic peptide

<400> SEQUENCE: 112

Ile Ser Ala Ile Asn Ser Tyr Thr
1               5

<210> SEQ ID NO 113
<211> LENGTH: 24
<212> TYPE: PRT
<213> ORGANISM: Artificial sequence
<220> FEATURE:
<223> OTHER INFORMATION: Synthetic peptide

<400> SEQUENCE: 113

Ala Arg Asp Val Gly Gly Ser Val Arg Tyr Ser Ser Asn Ser Asn Lys
1               5                   10                  15

Lys Ser Tyr Asn Tyr Phe Asp Pro
            20

<210> SEQ ID NO 114
<211> LENGTH: 8
<212> TYPE: PRT
<213> ORGANISM: Artificial sequence
<220> FEATURE:
<223> OTHER INFORMATION: Synthetic peptide

<400> SEQUENCE: 114

Gly Gly Thr Val Ser Ser Tyr Ala
1               5

<210> SEQ ID NO 115
<211> LENGTH: 8
<212> TYPE: PRT
<213> ORGANISM: Artificial sequence
<220> FEATURE:
<223> OTHER INFORMATION: Synthetic peptide

<400> SEQUENCE: 115

Ile Ile Pro Ile Phe Asp Thr Thr
1               5

<210> SEQ ID NO 116
<211> LENGTH: 28
<212> TYPE: PRT
<213> ORGANISM: Artificial sequence
<220> FEATURE:
<223> OTHER INFORMATION: Synthetic peptide

<400> SEQUENCE: 116

Ala Arg Asp Arg Val Pro Ser Tyr Ser Pro Ser Arg Arg Phe Ser Thr
1               5                   10                  15

Lys Gly Ala Met Trp Gly Lys Tyr Gly Met Asp Val
            20                  25

<210> SEQ ID NO 117
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 117

Gly Phe Thr Phe Ser Asp Tyr Tyr
1               5

<210> SEQ ID NO 118
<211> LENGTH: 8
<212> TYPE: PRT
<213> ORGANISM: Artificial sequence
<220> FEATURE:
<223> OTHER INFORMATION: Synthetic peptide

<400> SEQUENCE: 118

Ile Ser Ser Ser Phe Gly Ser Thr
1               5

<210> SEQ ID NO 119
<211> LENGTH: 15
<212> TYPE: PRT
<213> ORGANISM: Artificial sequence
<220> FEATURE:
<223> OTHER INFORMATION: Synthetic peptide

<400> SEQUENCE: 119

Ala Arg Tyr Asn Tyr Tyr Gly Ser Gly Ser Phe Val Phe Asp Tyr
1               5                   10                  15

<210> SEQ ID NO 120
<211> LENGTH: 12
<212> TYPE: PRT
<213> ORGANISM: Artificial sequence
<220> FEATURE:
<223> OTHER INFORMATION: Synthetic peptide

<400> SEQUENCE: 120

Gln Ser Val Leu Tyr Thr Ser Asp Asn Lys Asn Tyr
1               5                   10

<210> SEQ ID NO 121
<211> LENGTH: 3
<212> TYPE: PRT
<213> ORGANISM: Artificial sequence
<220> FEATURE:
<223> OTHER INFORMATION: Synthetic peptide

<400> SEQUENCE: 121

Trp Ala Ser
1

<210> SEQ ID NO 122
<211> LENGTH: 9
<212> TYPE: PRT
<213> ORGANISM: Artificial sequence
<220> FEATURE:
<223> OTHER INFORMATION: Synthetic peptide

<400> SEQUENCE: 122

Gln Gln Tyr Tyr Asn Ser Pro Leu Ala
1               5

<210> SEQ ID NO 123
<211> LENGTH: 9
<212> TYPE: PRT
<213> ORGANISM: Artificial sequence
<220> FEATURE:
<223> OTHER INFORMATION: Synthetic peptide
```

```
<400> SEQUENCE: 123

Ser Ser Asp Val Gly Gly Tyr Lys Tyr
1               5

<210> SEQ ID NO 124
<211> LENGTH: 3
<212> TYPE: PRT
<213> ORGANISM: Artificial sequence
<220> FEATURE:
<223> OTHER INFORMATION: Synthetic peptide

<400> SEQUENCE: 124

Glu Val Thr
1

<210> SEQ ID NO 125
<211> LENGTH: 12
<212> TYPE: PRT
<213> ORGANISM: Artificial sequence
<220> FEATURE:
<223> OTHER INFORMATION: Synthetic peptide

<400> SEQUENCE: 125

Gly Ser Tyr Ala Gly Ser Thr Thr Ser Gly Tyr Val
1               5                   10

<210> SEQ ID NO 126
<211> LENGTH: 8
<212> TYPE: PRT
<213> ORGANISM: Artificial sequence
<220> FEATURE:
<223> OTHER INFORMATION: Synthetic peptide

<400> SEQUENCE: 126

Ser Ser Asn Ile Gly Ser Asn Phe
1               5

<210> SEQ ID NO 127
<211> LENGTH: 3
<212> TYPE: PRT
<213> ORGANISM: Artificial sequence
<220> FEATURE:
<223> OTHER INFORMATION: Synthetic peptide

<400> SEQUENCE: 127

Lys Asn Asn
1

<210> SEQ ID NO 128
<211> LENGTH: 11
<212> TYPE: PRT
<213> ORGANISM: Artificial sequence
<220> FEATURE:
<223> OTHER INFORMATION: Synthetic peptide

<400> SEQUENCE: 128

Ser Ala Trp Asp Asp Ser Leu Ser Gly Pro Val
1               5                   10

<210> SEQ ID NO 129
<211> LENGTH: 9
<212> TYPE: PRT
<213> ORGANISM: Artificial sequence
<220> FEATURE:
<223> OTHER INFORMATION: Synthetic peptide

<400> SEQUENCE: 129
```

```
Ser Ser Asn Ile Gly Ala Asp Tyr Asp
1               5

<210> SEQ ID NO 130
<211> LENGTH: 3
<212> TYPE: PRT
<213> ORGANISM: Artificial sequence
<220> FEATURE:
<223> OTHER INFORMATION: Synthetic peptide

<400> SEQUENCE: 130

Ala Asp Ile
1

<210> SEQ ID NO 131
<211> LENGTH: 12
<212> TYPE: PRT
<213> ORGANISM: Artificial sequence
<220> FEATURE:
<223> OTHER INFORMATION: Synthetic peptide

<400> SEQUENCE: 131

Gln Ser Tyr Asp Arg Ser Val Ser Gly Ser Ala Val
1               5                   10

<210> SEQ ID NO 132
<211> LENGTH: 8
<212> TYPE: PRT
<213> ORGANISM: Artificial sequence
<220> FEATURE:
<223> OTHER INFORMATION: Synthetic peptide

<400> SEQUENCE: 132

Ser Ser Asn Ile Ala Asn Tyr Tyr
1               5

<210> SEQ ID NO 133
<211> LENGTH: 3
<212> TYPE: PRT
<213> ORGANISM: Artificial sequence
<220> FEATURE:
<223> OTHER INFORMATION: Synthetic peptide

<400> SEQUENCE: 133

Asp Asn Asn
1

<210> SEQ ID NO 134
<211> LENGTH: 11
<212> TYPE: PRT
<213> ORGANISM: Artificial sequence
<220> FEATURE:
<223> OTHER INFORMATION: Synthetic peptide

<400> SEQUENCE: 134

Gly Thr Trp Asp Thr Ser Leu Ser Ala Trp Val
1               5                   10

<210> SEQ ID NO 135
<211> LENGTH: 8
<212> TYPE: PRT
<213> ORGANISM: Artificial sequence
<220> FEATURE:
<223> OTHER INFORMATION: Synthetic peptide

<400> SEQUENCE: 135
```

```
Ser Ser Asn Ile Gly Thr Tyr Tyr
1               5
```

```
<210> SEQ ID NO 136
<211> LENGTH: 3
<212> TYPE: PRT
<213> ORGANISM: Artificial sequence
<220> FEATURE:
<223> OTHER INFORMATION: Synthetic peptide

<400> SEQUENCE: 136

Asp Asn Asp
1
```

```
<210> SEQ ID NO 137
<211> LENGTH: 12
<212> TYPE: PRT
<213> ORGANISM: Artificial sequence
<220> FEATURE:
<223> OTHER INFORMATION: Synthetic peptide

<400> SEQUENCE: 137

Gly Thr Trp Asp Leu Ser Leu Thr Ala Gly Trp Val
1               5                   10
```

```
<210> SEQ ID NO 138
<211> LENGTH: 9
<212> TYPE: PRT
<213> ORGANISM: Artificial sequence
<220> FEATURE:
<223> OTHER INFORMATION: Synthetic peptide

<400> SEQUENCE: 138

Ser Ser Asn Ile Gly Ala Gly Tyr Asp
1               5
```

```
<210> SEQ ID NO 139
<211> LENGTH: 3
<212> TYPE: PRT
<213> ORGANISM: Artificial sequence
<220> FEATURE:
<223> OTHER INFORMATION: Synthetic peptide

<400> SEQUENCE: 139

Gly Asn Ser
1
```

```
<210> SEQ ID NO 140
<211> LENGTH: 12
<212> TYPE: PRT
<213> ORGANISM: Artificial sequence
<220> FEATURE:
<223> OTHER INFORMATION: Synthetic peptide

<400> SEQUENCE: 140

Gln Ser Tyr Asp Ser Ser Leu Ser Gly Pro Val Val
1               5                   10
```

```
<210> SEQ ID NO 141
<211> LENGTH: 8
<212> TYPE: PRT
<213> ORGANISM: Artificial sequence
<220> FEATURE:
<223> OTHER INFORMATION: Synthetic peptide

<400> SEQUENCE: 141

Asn Ser Asn Ile Gly Ile Ser Tyr
```

```
1               5

<210> SEQ ID NO 142
<211> LENGTH: 3
<212> TYPE: PRT
<213> ORGANISM: Artificial sequence
<220> FEATURE:
<223> OTHER INFORMATION: Synthetic peptide

<400> SEQUENCE: 142

Lys Asn Asn
1

<210> SEQ ID NO 143
<211> LENGTH: 10
<212> TYPE: PRT
<213> ORGANISM: Artificial sequence
<220> FEATURE:
<223> OTHER INFORMATION: Synthetic peptide

<400> SEQUENCE: 143

Ala Thr Leu Asp Ile Asn Met Thr Trp Val
1               5                   10

<210> SEQ ID NO 144
<211> LENGTH: 9
<212> TYPE: PRT
<213> ORGANISM: Artificial sequence
<220> FEATURE:
<223> OTHER INFORMATION: Synthetic peptide

<400> SEQUENCE: 144

Ser Ser Asn Ile Gly Ala Gly Tyr Asp
1               5

<210> SEQ ID NO 145
<211> LENGTH: 3
<212> TYPE: PRT
<213> ORGANISM: Artificial sequence
<220> FEATURE:
<223> OTHER INFORMATION: Synthetic peptide

<400> SEQUENCE: 145

Asp Asn Asn
1

<210> SEQ ID NO 146
<211> LENGTH: 12
<212> TYPE: PRT
<213> ORGANISM: Artificial sequence
<220> FEATURE:
<223> OTHER INFORMATION: Synthetic peptide

<400> SEQUENCE: 146

Gln Ser Tyr Asp Ser Arg Leu Ser Ser Asn Val Val
1               5                   10

<210> SEQ ID NO 147
<211> LENGTH: 9
<212> TYPE: PRT
<213> ORGANISM: Artificial sequence
<220> FEATURE:
<223> OTHER INFORMATION: Synthetic peptide

<400> SEQUENCE: 147

Ser Ser Asp Val Gly Gly Tyr Asn Tyr
1               5
```

```
<210> SEQ ID NO 148
<211> LENGTH: 3
<212> TYPE: PRT
<213> ORGANISM: Artificial sequence
<220> FEATURE:
<223> OTHER INFORMATION: Synthetic peptide

<400> SEQUENCE: 148

Glu Ile Ser
1

<210> SEQ ID NO 149
<211> LENGTH: 11
<212> TYPE: PRT
<213> ORGANISM: Artificial sequence
<220> FEATURE:
<223> OTHER INFORMATION: Synthetic peptide

<400> SEQUENCE: 149

Ser Ser Tyr Ala Gly Thr Tyr Asn Cys Val Val
1               5                   10

<210> SEQ ID NO 150
<211> LENGTH: 6
<212> TYPE: PRT
<213> ORGANISM: Artificial sequence
<220> FEATURE:
<223> OTHER INFORMATION: Synthetic peptide

<400> SEQUENCE: 150

Gln Asp Ile Ser Asp Tyr
1               5

<210> SEQ ID NO 151
<211> LENGTH: 3
<212> TYPE: PRT
<213> ORGANISM: Artificial sequence
<220> FEATURE:
<223> OTHER INFORMATION: Synthetic peptide

<400> SEQUENCE: 151

Ala Ala Ser
1

<210> SEQ ID NO 152
<211> LENGTH: 9
<212> TYPE: PRT
<213> ORGANISM: Artificial sequence
<220> FEATURE:
<223> OTHER INFORMATION: Synthetic peptide

<400> SEQUENCE: 152

Leu Gln His Asp Thr Tyr Pro Leu Thr
1               5

<210> SEQ ID NO 153
<211> LENGTH: 9
<212> TYPE: PRT
<213> ORGANISM: Artificial sequence
<220> FEATURE:
<223> OTHER INFORMATION: Synthetic peptide

<400> SEQUENCE: 153

Ser Ser Asn Ile Gly Ala Gly Tyr Glu
1               5
```

-continued

```
<210> SEQ ID NO 154
<211> LENGTH: 3
<212> TYPE: PRT
<213> ORGANISM: Artificial sequence
<220> FEATURE:
<223> OTHER INFORMATION: Synthetic peptide

<400> SEQUENCE: 154

Gly Asn Asn
1

<210> SEQ ID NO 155
<211> LENGTH: 9
<212> TYPE: PRT
<213> ORGANISM: Artificial sequence
<220> FEATURE:
<223> OTHER INFORMATION: Synthetic peptide

<400> SEQUENCE: 155

Gln Ser Tyr Asp Asn Arg Leu Arg Val
1               5

<210> SEQ ID NO 156
<211> LENGTH: 11
<212> TYPE: PRT
<213> ORGANISM: Artificial sequence
<220> FEATURE:
<223> OTHER INFORMATION: Synthetic peptide

<400> SEQUENCE: 156

Gln Ser Leu Leu His Ser Asn Gly Tyr Asn Tyr
1               5                   10

<210> SEQ ID NO 157
<211> LENGTH: 3
<212> TYPE: PRT
<213> ORGANISM: Artificial sequence
<220> FEATURE:
<223> OTHER INFORMATION: Synthetic peptide

<400> SEQUENCE: 157

Leu Gly Ser
1

<210> SEQ ID NO 158
<211> LENGTH: 8
<212> TYPE: PRT
<213> ORGANISM: Artificial sequence
<220> FEATURE:
<223> OTHER INFORMATION: Synthetic peptide

<400> SEQUENCE: 158

Met Gln Ala Leu Gln Thr Arg Thr
1               5

<210> SEQ ID NO 159
<211> LENGTH: 9
<212> TYPE: PRT
<213> ORGANISM: Artificial sequence
<220> FEATURE:
<223> OTHER INFORMATION: Synthetic peptide

<400> SEQUENCE: 159

Ser Ser Asn Ile Gly Ala Gly Tyr Asp
1               5
```

```
<210> SEQ ID NO 160
<211> LENGTH: 3
<212> TYPE: PRT
<213> ORGANISM: Artificial sequence
<220> FEATURE:
<223> OTHER INFORMATION: Synthetic peptide

<400> SEQUENCE: 160

His Asn Thr
1

<210> SEQ ID NO 161
<211> LENGTH: 12
<212> TYPE: PRT
<213> ORGANISM: Artificial sequence
<220> FEATURE:
<223> OTHER INFORMATION: Synthetic peptide

<400> SEQUENCE: 161

Gln Ser Tyr Asp Arg Ser Leu Ser Lys Ser Arg Val
1               5                   10

<210> SEQ ID NO 162
<211> LENGTH: 6
<212> TYPE: PRT
<213> ORGANISM: Artificial sequence
<220> FEATURE:
<223> OTHER INFORMATION: Synthetic peptide

<400> SEQUENCE: 162

Val Leu Ser Lys Glu Phe
1               5

<210> SEQ ID NO 163
<211> LENGTH: 3
<212> TYPE: PRT
<213> ORGANISM: Artificial sequence
<220> FEATURE:
<223> OTHER INFORMATION: Synthetic peptide

<400> SEQUENCE: 163

Lys Asp Asn
1

<210> SEQ ID NO 164
<211> LENGTH: 11
<212> TYPE: PRT
<213> ORGANISM: Artificial sequence
<220> FEATURE:
<223> OTHER INFORMATION: Synthetic peptide

<400> SEQUENCE: 164

Gln Ser Val Asp Thr Arg Gly Thr Tyr Lys Val
1               5                   10

<210> SEQ ID NO 165
<211> LENGTH: 11
<212> TYPE: PRT
<213> ORGANISM: Artificial sequence
<220> FEATURE:
<223> OTHER INFORMATION: Synthetic peptide

<400> SEQUENCE: 165

Gln Ser Leu Leu His Ser Asn Gly Tyr Asn Tyr
1               5                   10

<210> SEQ ID NO 166
```

```
<211> LENGTH: 3
<212> TYPE: PRT
<213> ORGANISM: Artificial sequence
<220> FEATURE:
<223> OTHER INFORMATION: Synthetic peptide

<400> SEQUENCE: 166

Leu Gly Ser
1

<210> SEQ ID NO 167
<211> LENGTH: 9
<212> TYPE: PRT
<213> ORGANISM: Artificial sequence
<220> FEATURE:
<223> OTHER INFORMATION: Synthetic peptide

<400> SEQUENCE: 167

Met Gln Ala Leu Gln Thr Pro Arg Thr
1               5

<210> SEQ ID NO 168
<211> LENGTH: 8
<212> TYPE: PRT
<213> ORGANISM: Artificial sequence
<220> FEATURE:
<223> OTHER INFORMATION: Synthetic peptide

<400> SEQUENCE: 168

Ser Ser Asn Ile Gly Ser Asn Thr
1               5

<210> SEQ ID NO 169
<211> LENGTH: 3
<212> TYPE: PRT
<213> ORGANISM: Artificial sequence
<220> FEATURE:
<223> OTHER INFORMATION: Synthetic peptide

<400> SEQUENCE: 169

Ser Asn Asp
1

<210> SEQ ID NO 170
<211> LENGTH: 11
<212> TYPE: PRT
<213> ORGANISM: Artificial sequence
<220> FEATURE:
<223> OTHER INFORMATION: Synthetic peptide

<400> SEQUENCE: 170

Ala Ala Trp Asp Asp Ser Leu Asn Gly Trp Val
1               5                   10

<210> SEQ ID NO 171
<211> LENGTH: 17
<212> TYPE: PRT
<213> ORGANISM: Artificial sequence
<220> FEATURE:
<223> OTHER INFORMATION: Synthetic peptide

<400> SEQUENCE: 171

Cys Ala Arg Asp Arg Leu Pro Ala Ser Gly Ser His Trp Phe His Pro
1               5                   10                  15

Trp
```

```
<210> SEQ ID NO 172
<211> LENGTH: 22
<212> TYPE: PRT
<213> ORGANISM: Artificial sequence
<220> FEATURE:
<223> OTHER INFORMATION: Synthetic peptide

<400> SEQUENCE: 172

Cys Ala Arg Met Gly Arg Leu Glu Leu Glu Arg Arg Pro His Tyr Tyr
1               5                   10                  15

Tyr Pro Leu Asp Val Trp
            20

<210> SEQ ID NO 173
<211> LENGTH: 17
<212> TYPE: PRT
<213> ORGANISM: Artificial sequence
<220> FEATURE:
<223> OTHER INFORMATION: Synthetic peptide

<400> SEQUENCE: 173

Cys Ala Arg Ala Thr Ser Gln Gly Ala Thr Ser Tyr Tyr Phe Asp Ser
1               5                   10                  15

Trp

<210> SEQ ID NO 174
<211> LENGTH: 19
<212> TYPE: PRT
<213> ORGANISM: Artificial sequence
<220> FEATURE:
<223> OTHER INFORMATION: Synthetic peptide

<400> SEQUENCE: 174

Cys Ala Lys Val Glu Ile His Tyr Tyr Ser Asn Ser Leu Leu Gly Met
1               5                   10                  15

Asp Val Trp

<210> SEQ ID NO 175
<211> LENGTH: 17
<212> TYPE: PRT
<213> ORGANISM: Artificial sequence
<220> FEATURE:
<223> OTHER INFORMATION: Synthetic peptide

<400> SEQUENCE: 175

Cys Ala Arg Tyr Asn Tyr Tyr Gly Ser Gly Ser Phe Val Phe Asp Tyr
1               5                   10                  15

Trp

<210> SEQ ID NO 176
<211> LENGTH: 18
<212> TYPE: PRT
<213> ORGANISM: Artificial sequence
<220> FEATURE:
<223> OTHER INFORMATION: Synthetic peptide

<400> SEQUENCE: 176

Cys Ala Arg Asp Leu Leu Arg Asn Trp Gly Asp His Asp Ala Phe Asp
1               5                   10                  15

Val Trp

<210> SEQ ID NO 177
<211> LENGTH: 20
<212> TYPE: PRT
```

<213> ORGANISM: Artificial sequence
<220> FEATURE:
<223> OTHER INFORMATION: Synthetic peptide

<400> SEQUENCE: 177

Cys Ala Arg Asp Ala Gln Tyr Cys Ser Gly Gly Arg Cys Tyr Leu Val
1               5                   10                  15

Phe Asp Tyr Trp
            20

<210> SEQ ID NO 178
<211> LENGTH: 19
<212> TYPE: PRT
<213> ORGANISM: Artificial sequence
<220> FEATURE:
<223> OTHER INFORMATION: Synthetic peptide

<400> SEQUENCE: 178

Cys Ala Arg Gly Gln Met Arg Thr Arg Gly Ala Leu Phe Arg Arg Phe
1               5                   10                  15

Asp Pro Trp

<210> SEQ ID NO 179
<211> LENGTH: 18
<212> TYPE: PRT
<213> ORGANISM: Artificial sequence
<220> FEATURE:
<223> OTHER INFORMATION: Synthetic peptide

<400> SEQUENCE: 179

Cys Ala Arg Asp Cys Arg Val Gly Trp Val Phe Thr Tyr Gly Met Asp
1               5                   10                  15

Val Trp

<210> SEQ ID NO 180
<211> LENGTH: 18
<212> TYPE: PRT
<213> ORGANISM: Artificial sequence
<220> FEATURE:
<223> OTHER INFORMATION: Synthetic peptide

<400> SEQUENCE: 180

Cys Ala Arg Tyr Gly Ala Glu Tyr Gly Ser Arg Ser Phe Tyr Phe Leu
1               5                   10                  15

Asp Trp

<210> SEQ ID NO 181
<211> LENGTH: 16
<212> TYPE: PRT
<213> ORGANISM: Artificial sequence
<220> FEATURE:
<223> OTHER INFORMATION: Synthetic peptide

<400> SEQUENCE: 181

Cys Ala Arg Glu Asp Cys His Gly Thr Ser Cys Tyr Ser Gly Asp Trp
1               5                   10                  15

<210> SEQ ID NO 182
<211> LENGTH: 19
<212> TYPE: PRT
<213> ORGANISM: Artificial sequence
<220> FEATURE:
<223> OTHER INFORMATION: Synthetic peptide

<400> SEQUENCE: 182

```
Cys Ala Lys Val Arg Leu Thr Ser Tyr Ser Ile Gly Trp Phe Ser Phe
1               5                   10                  15

Asp Tyr Trp

<210> SEQ ID NO 183
<211> LENGTH: 19
<212> TYPE: PRT
<213> ORGANISM: Artificial sequence
<220> FEATURE:
<223> OTHER INFORMATION: Synthetic peptide

<400> SEQUENCE: 183

Cys Ala Lys Asp Phe Leu Arg Val Tyr Ser Tyr Gly Trp His Ser Phe
1               5                   10                  15

Asp Ile Trp

<210> SEQ ID NO 184
<211> LENGTH: 16
<212> TYPE: PRT
<213> ORGANISM: Artificial sequence
<220> FEATURE:
<223> OTHER INFORMATION: Synthetic peptide

<400> SEQUENCE: 184

Cys Ala Lys Val Thr Ile Ile Ala Ala Ala Asp Leu Leu Asp Tyr Trp
1               5                   10                  15

<210> SEQ ID NO 185
<211> LENGTH: 26
<212> TYPE: PRT
<213> ORGANISM: Artificial sequence
<220> FEATURE:
<223> OTHER INFORMATION: Synthetic peptide

<400> SEQUENCE: 185

Cys Ala Arg Val Thr Gly Asp Cys Thr Gly Asn Arg Cys Ser Tyr Trp
1               5                   10                  15

Ala Tyr Tyr Tyr Tyr Gly Leu Asp Val Trp
            20                  25

<210> SEQ ID NO 186
<211> LENGTH: 26
<212> TYPE: PRT
<213> ORGANISM: Artificial sequence
<220> FEATURE:
<223> OTHER INFORMATION: Synthetic peptide

<400> SEQUENCE: 186

Cys Thr Arg Asp Pro Ser Gln Tyr Tyr Asp Ser Arg Gly His Tyr Tyr
1               5                   10                  15

Gln Thr Phe Thr Pro Ser Phe Asp Ser Trp
            20                  25

<210> SEQ ID NO 187
<211> LENGTH: 30
<212> TYPE: PRT
<213> ORGANISM: Artificial sequence
<220> FEATURE:
<223> OTHER INFORMATION: Synthetic peptide

<400> SEQUENCE: 187

Cys Ala Arg Asp Arg Val Pro Ser Tyr Ser Pro Ser Arg Arg Phe Ser
1               5                   10                  15
```

```
Thr Lys Gly Ala Met Trp Gly Lys Tyr Gly Met Asp Val Trp
            20                  25                  30
```

```
<210> SEQ ID NO 188
<211> LENGTH: 11
<212> TYPE: PRT
<213> ORGANISM: Artificial sequence
<220> FEATURE:
<223> OTHER INFORMATION: Synthetic peptide

<400> SEQUENCE: 188

Cys Gln Gln Tyr Tyr Asn Ser Pro Leu Ala Phe
1               5                   10
```

```
<210> SEQ ID NO 189
<211> LENGTH: 10
<212> TYPE: PRT
<213> ORGANISM: Artificial sequence
<220> FEATURE:
<223> OTHER INFORMATION: Synthetic peptide

<400> SEQUENCE: 189

Cys Met Gln Ala Leu Gln Thr Arg Thr Phe
1               5                   10
```

```
<210> SEQ ID NO 190
<211> LENGTH: 14
<212> TYPE: PRT
<213> ORGANISM: Artificial sequence
<220> FEATURE:
<223> OTHER INFORMATION: Synthetic peptide

<400> SEQUENCE: 190

Cys Gln Ser Tyr Asp Arg Ser Val Ser Gly Ser Ala Val Phe
1               5                   10
```

```
<210> SEQ ID NO 191
<211> LENGTH: 12
<212> TYPE: PRT
<213> ORGANISM: Artificial sequence
<220> FEATURE:
<223> OTHER INFORMATION: Synthetic peptide

<400> SEQUENCE: 191

Cys Ala Thr Leu Asp Ile Asn Met Thr Trp Val Phe
1               5                   10
```

```
<210> SEQ ID NO 192
<211> LENGTH: 13
<212> TYPE: PRT
<213> ORGANISM: Artificial sequence
<220> FEATURE:
<223> OTHER INFORMATION: Synthetic peptide

<400> SEQUENCE: 192

Cys Ala Ala Trp Asp Asp Ser Leu Asn Gly Trp Val Phe
1               5                   10
```

```
<210> SEQ ID NO 193
<211> LENGTH: 13
<212> TYPE: PRT
<213> ORGANISM: Artificial sequence
<220> FEATURE:
<223> OTHER INFORMATION: Synthetic peptide

<400> SEQUENCE: 193

Cys Ser Ala Trp Asp Asp Ser Leu Ser Gly Pro Val Phe
```

```
1               5                  10

<210> SEQ ID NO 194
<211> LENGTH: 11
<212> TYPE: PRT
<213> ORGANISM: Artificial sequence
<220> FEATURE:
<223> OTHER INFORMATION: Synthetic peptide

<400> SEQUENCE: 194

Cys Gln Ser Tyr Asp Asn Arg Leu Arg Val Phe
1               5                  10

<210> SEQ ID NO 195
<211> LENGTH: 13
<212> TYPE: PRT
<213> ORGANISM: Artificial sequence
<220> FEATURE:
<223> OTHER INFORMATION: Synthetic peptide

<400> SEQUENCE: 195

Cys Gln Ser Val Asp Thr Arg Gly Thr Tyr Lys Val Phe
1               5                  10

<210> SEQ ID NO 196
<211> LENGTH: 13
<212> TYPE: PRT
<213> ORGANISM: Artificial sequence
<220> FEATURE:
<223> OTHER INFORMATION: Synthetic peptide

<400> SEQUENCE: 196

Cys Ser Ser Tyr Ala Gly Thr Tyr Asn Cys Val Val Phe
1               5                  10

<210> SEQ ID NO 197
<211> LENGTH: 14
<212> TYPE: PRT
<213> ORGANISM: Artificial sequence
<220> FEATURE:
<223> OTHER INFORMATION: Synthetic peptide

<400> SEQUENCE: 197

Cys Gln Ser Tyr Asp Ser Arg Leu Ser Ser Asn Val Val Phe
1               5                  10

<210> SEQ ID NO 198
<211> LENGTH: 14
<212> TYPE: PRT
<213> ORGANISM: Artificial sequence
<220> FEATURE:
<223> OTHER INFORMATION: Synthetic peptide

<400> SEQUENCE: 198

Cys Gln Ser Tyr Asp Arg Ser Leu Ser Lys Ser Arg Val Phe
1               5                  10

<210> SEQ ID NO 199
<211> LENGTH: 13
<212> TYPE: PRT
<213> ORGANISM: Artificial sequence
<220> FEATURE:
<223> OTHER INFORMATION: Synthetic peptide

<400> SEQUENCE: 199

Cys Gly Thr Trp Asp Thr Ser Leu Arg Ala Cys Leu Phe
1               5                  10
```

```
<210> SEQ ID NO 200
<211> LENGTH: 14
<212> TYPE: PRT
<213> ORGANISM: Artificial sequence
<220> FEATURE:
<223> OTHER INFORMATION: Synthetic peptide

<400> SEQUENCE: 200

Cys Gly Thr Trp Asp Leu Ser Leu Thr Ala Gly Trp Val Phe
1               5                   10

<210> SEQ ID NO 201
<211> LENGTH: 14
<212> TYPE: PRT
<213> ORGANISM: Artificial sequence
<220> FEATURE:
<223> OTHER INFORMATION: Synthetic peptide

<400> SEQUENCE: 201

Cys Gln Ser Tyr Asp Ser Ser Leu Ser Gly Pro Val Val Phe
1               5                   10

<210> SEQ ID NO 202
<211> LENGTH: 14
<212> TYPE: PRT
<213> ORGANISM: Artificial sequence
<220> FEATURE:
<223> OTHER INFORMATION: Synthetic peptide

<400> SEQUENCE: 202

Cys Gly Ser Tyr Ala Gly Ser Thr Thr Ser Gly Tyr Val Phe
1               5                   10

<210> SEQ ID NO 203
<211> LENGTH: 11
<212> TYPE: PRT
<213> ORGANISM: Artificial sequence
<220> FEATURE:
<223> OTHER INFORMATION: Synthetic peptide

<400> SEQUENCE: 203

Cys Leu Gln His Asp Thr Tyr Pro Leu Thr Phe
1               5                   10

<210> SEQ ID NO 204
<211> LENGTH: 11
<212> TYPE: PRT
<213> ORGANISM: Artificial sequence
<220> FEATURE:
<223> OTHER INFORMATION: Synthetic peptide

<400> SEQUENCE: 204

Cys Met Gln Ala Leu Gln Thr Pro Arg Thr Phe
1               5                   10

<210> SEQ ID NO 205
<211> LENGTH: 540
<212> TYPE: PRT
<213> ORGANISM: Artificial sequence
<220> FEATURE:
<223> OTHER INFORMATION: Synthetic polypeptide

<400> SEQUENCE: 205

Met Lys Met Ala Ser Ser Asp Ala Ser Pro Ser Asp Gly Ser Thr Ala
1               5                   10                  15
```

-continued

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
    50                      55                  60

Thr Val Ser Pro Arg Asn Ala Pro Gly Glu Ile Leu Trp Ser Ala Pro
65                      70                  75                  80

Leu Gly Pro Asp Leu Asn Pro Tyr Leu Ser His Leu Ala Arg Met Tyr
                85                      90                  95

Asn Gly Tyr Ala Gly Phe Glu Val Gln Val Ile Leu Ala Gly Asn
                100                     105                 110

Ala Phe Thr Ala Gly Lys Ile Ile Phe Ala Ala Val Pro Pro Asn Phe
                115                 120                     125

Pro Thr Glu Gly Leu Ser Pro Ser Gln Val Thr Met Phe Pro His Ile
    130                     135                 140

Ile Val Asp Val Arg Gln Leu Glu Pro Val Leu Ile Pro Leu Pro Asp
145                 150                     155                 160

Val Arg Asn Asn Phe Tyr His Tyr Asn Gln Ser Asn Asp Pro Thr Ile
                165                     170                 175

Lys Leu Ile Ala Met Leu Tyr Thr Pro Leu Tyr Ala Asn Asn Ala Gly
                180                 185                     190

Asp Asp Val Phe Thr Val Ser Cys Arg Val Leu Thr Arg Pro Ser Pro
                195                 200                     205

Asp Phe Asp Phe Ile Phe Leu Val Pro Pro Thr Val Glu Ser Arg Thr
210                     215                 220

Lys Pro Phe Thr Val Pro Ile Leu Thr Val Glu Glu Met Thr Asn Ser
225                 230                     235                 240

Arg Phe Pro Ile Pro Leu Glu Lys Leu Phe Thr Gly Pro Ser Gly Ala
                245                 250                     255

Phe Val Val Gln Pro Gln Asn Gly Arg Cys Thr Thr Asp Gly Val Leu
                260                 265                     270

Leu Gly Thr Thr Gln Leu Ser Pro Val Asn Ile Cys Thr Phe Arg Gly
                275                 280                     285

Asp Val Thr His Ile Ala Gly Thr His Asp Tyr Thr Met Asn Leu Ala
                290                 295                     300

Ser Gln Asn Trp Asn Asn Tyr Asp Pro Thr Glu Glu Ile Pro Ala Pro
305                     310                 315                 320

Leu Gly Thr Pro Asp Phe Val Gly Lys Ile Gln Gly Val Leu Thr Gln
                325                 330                     335

Thr Thr Arg Gly Asp Gly Ser Thr Arg Gly His Lys Ala Thr Val Ser
                340                     345                 350

Thr Gly Ser Val His Phe Thr Pro Lys Leu Gly Ser Val Gln Phe Thr
                355                     360                 365

Thr Asp Thr Asn Asn Asp Leu Glu Thr Gly Gln Asn Thr Lys Phe Thr
                370                     375                 380

Pro Val Gly Val Val Gln Asp Gly Asn Ser Ala His Gln Asn Glu Pro
385                     390                     395                 400

Gln Gln Trp Val Leu Pro Asn Tyr Ser Gly Arg Thr Gly His Asn Val
                405                     410                 415

His Leu Ala Pro Ala Val Ala Pro Thr Phe Pro Gly Glu Gln Leu Leu
                420                     425                 430

Phe Phe Arg Ser Thr Met Pro Gly Cys Ser Gly Tyr Pro Asn Met Asn

```
            435                 440                 445
Leu Asp Cys Leu Leu Pro Gln Glu Trp Val Leu His Phe Tyr Gln Glu
450                 455                 460
Ala Ala Pro Ala Gln Ser Asp Val Ala Leu Leu Arg Phe Val Asn Pro
465                 470                 475                 480
Asp Thr Gly Arg Val Leu Phe Glu Cys Lys Leu His Lys Ser Gly Tyr
                    485                 490                 495
Val Thr Val Ala His Thr Gly Pro His Asp Leu Val Ile Pro Pro Asn
                500                 505                 510
Gly Tyr Phe Arg Phe Asp Ser Trp Val Asn Gln Phe Tyr Thr Leu Ala
                515                 520                 525
Pro Met Gly Asn Gly Ala Gly Arg Arg Arg Ala Leu
530                 535                 540

<210> SEQ ID NO 206
<211> LENGTH: 540
<212> TYPE: PRT
<213> ORGANISM: Artificial sequence
<220> FEATURE:
<223> OTHER INFORMATION: Synthetic polypeptide

<400> SEQUENCE: 206

Met Lys Met Ala Ser Ser Asp Ala Asn Pro Ser Asp Gly Ser Ala Ala
1               5                   10                  15
Asn Leu Val Pro Glu Val Asn Asn Glu Val Met Ala Leu Glu Pro Val
                20                  25                  30
Val Gly Ala Ala Ile Ala Ala Pro Val Ala Gly Gln Gln Asn Val Ile
            35                  40                  45
Asp Pro Trp Ile Arg Asn Asn Phe Val Gln Ala Pro Gly Gly Glu Phe
    50                  55                  60
Thr Val Ser Pro Arg Asn Ala Pro Gly Glu Ile Leu Trp Ser Ala Pro
65                  70                  75                  80
Leu Gly Pro Asp Leu Asn Pro Tyr Leu Ser His Leu Ala Arg Met Tyr
                85                  90                  95
Asn Gly Tyr Ala Gly Gly Phe Glu Val Gln Val Ile Leu Ala Gly Asn
                100                 105                 110
Ala Phe Thr Ala Gly Lys Val Ile Phe Ala Ala Val Pro Pro Asn Phe
            115                 120                 125
Pro Thr Glu Gly Leu Ser Pro Ser Gln Val Thr Met Phe Pro His Ile
    130                 135                 140
Val Val Asp Val Arg Gln Leu Glu Pro Val Leu Ile Pro Leu Pro Asp
145                 150                 155                 160
Val Arg Asn Asn Phe Tyr His Tyr Asn Gln Ser Asn Asp Pro Thr Ile
                165                 170                 175
Lys Leu Ile Ala Met Leu Tyr Thr Pro Leu Tyr Ala Asn Asn Ala Gly
                180                 185                 190
Asp Asp Val Phe Thr Val Ser Cys Arg Val Leu Thr Arg Pro Ser Pro
            195                 200                 205
Asp Phe Asp Phe Ile Phe Leu Val Pro Pro Thr Val Glu Ser Arg Thr
    210                 215                 220
Lys Pro Phe Ser Val Pro Val Leu Thr Val Glu Met Thr Asn Ser
225                 230                 235                 240
Arg Phe Pro Ile Pro Leu Glu Lys Leu Phe Thr Gly Pro Ser Ser Ala
                245                 250                 255
Phe Val Val Gln Pro Gln Asn Gly Arg Cys Thr Thr Asp Gly Val Leu
```

-continued

```
                260                 265                 270
Leu Gly Thr Thr Gln Leu Ser Pro Val Asn Ile Cys Thr Phe Arg Gly
            275                 280                 285

Asp Val Thr His Ile Thr Gly Ser Arg Asn Tyr Thr Met Asn Leu Ala
        290                 295                 300

Ser Gln Asn Trp Asn Asp Tyr Asp Pro Thr Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Leu Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 207
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 207

```
caggtgcagc tggtggagtc tgggggaggc gtggtccagc ctggggggtc cctgagactc      60
tcctgtacag cgtctggatt caccttcagt ggtcatggca tgcactgggt ccgccaggct     120
ccaggcaagg ggctggaatg ggtgacattt atatcatatg atggaagtaa taaattctat     180
gcggactcag tgaagggccg attcatcatc tccagagaca attccgagaa cacgttgttt     240
ctgcagatga acagcctgag accggaagac acggagtct attggtgtgc gagagatggt      300
tacagaaatt tggtcctcgt tgggtggtac ttcgatctct ggggccgtgg caccctggtc     360
accgtctcct ca                                                         372
```

<210> SEQ ID NO 208

<400> SEQUENCE: 208

000

<210> SEQ ID NO 209

<400> SEQUENCE: 209

000

<210> SEQ ID NO 210
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 210

```
gagattgtgc tgacccaaag tcccgctaca cttagcctgt ctcctggaga ttctgctaca    60
ctgagctgta gagcttctca ggctgtgtct accacctatc tggcctggta tcagcagaca   120
agaggacaag cccctagact gctgattcac ggcacctaca caagagctat cggcattcct   180
gacaagtttt ctggaaccgg ctctggcacc gattttaccc tgaccatctc tggacttgcc   240
cctgaggatt tgctgtgta ctactgccag cagtacagct ctagcccta cacctttgga   300 cagggcacca agatcgagat cacc                                          324
```

<210> SEQ ID NO 211

<400> SEQUENCE: 211

000

<210> SEQ ID NO 212
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 212

```
agcaacgaac tgacacaagc cccttctgtg tctgtgtctc ctggacaaac agccagaatc    60
acctgcttcg gagatgctct ggctaaccag tacagctact ggtaccagag aaaaccagga   120
caggctccag tgctggtgat ctacaaggac agcgagagac tagcggaat tcctcagaga   180 ttttctgcct ccaatagcgg caccacagtg acactgacca tcacaggagt gcaggctgaa   240
gatgaagccg attacttctg tcagagcgcc gattctacag gcatctacaa ggtgtttggc   300
ggcggcacaa aactgacagt tctg                                          324
```

<210> SEQ ID NO 213
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 213

```
caggtgcagc tggtggagtc tgggggaggc ttggtcaagc ctggagggtc cctgagactc    60
tcctgtgcag cctctggatt cacccttgagt gactactaca tgagttggat ccgccaggct   120
ccagggaagg ggctggagtg ggttgcatac atcagtagta gtcatacttc cacatactac   180
```

| | |
|---|---|
| agagactctg tgaagggccg attcaccatc tccagggaca gcgccaagaa gtcactgtat | 240 |
| ctgcaaatga acagcctgag agtcgaggac acggctatat attactgtgc gagagattgg | 300 |
| gtaggtggta ggagcgcgta tagtgaccac tggggccagg aaccctggt caccgtctcc | 360 |
| tca | 363 |

<210> SEQ ID NO 214
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 214

| | |
|---|---|
| tcctatgagc tgacacagcc accctcggtg tcagtgtccc caggacaaac ggccaggatc | 60 |
| acctgctctg gagatgcgtt gccaagaaga cctgcttttt ggtatcagca gaagtcaggc | 120 |
| caggcccctg tgttggtcat gtatgacgac agcaaacgac cctccgggat ccctgagaga | 180 |
| ttctctggct ccagctcagg gacagtggcc accctgacta ttagtggggc caggtggag | 240 |
| gatgaagctg actaccactg ttactcaaca gacagcagtg gtaaggaaag agttttcggc | 300 |
| ggagggacca gctgaccgt cctc | 324 |

<210> SEQ ID NO 215
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 215

| | |
|---|---|
| caggtccagc tggtgcagtc tggggctgag gtgaagaagc ctggggcctc agtgaaaatt | 60 |
| tcctgcaagg cttctggata cgacttcact agttttccta tgcattgggt gcgcctgggc | 120 |
| cccggacaaa ggcttgagtg gatgggatgg atcagcgctg ccaatggtaa cacaaaatat | 180 |
| tcacagaagt tccaggacag attcaccatt accagggaca catccgcgag tatagtccac | 240 |
| atggagttga gtagcctgag atctgaagac acggctgtat actactgtgc gaggggggg | 300 |
| tatagtagtg ggctgtacag atattccaac tactactacg gtatgaccgt ctggggccaa | 360 |
| gggaccctgg tcaccgtctc ctca | 384 |

<210> SEQ ID NO 216
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 216

| | |
|---|---|
| gatattgtga tgacccagac tccactctct ctgtccgtca cccctggaca gccggcctcc | 60 |
| atctcctgca gtctagtga gagcctcctg cataatgatc gaaaaaccta tttgttttgg | 120 |
| tacctgcaga agccaggcca gcctccacaa ctcctgatct ttcaagtctc caaccggttc | 180 |
| tctggagtgc cagataggtt cagtggcagc ggatcaggga cagacttcac actgagaatc | 240 |
| agccgtgtgg aggctgagga tgttgggatt tattactgct tgcaaactac acagcttccg | 300 |
| ctcactttcg gcggagggac caaggtggag atcaaa | 336 |

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 220

```
gatattgtga tgactcagtc tccactctcc ctgcccgtca cccctggaga gccggcctcc      60
atctcctgca ggtctagtca gagcctcctt cacagtgatg gactcaacta tttggattgg    120
tacctgctga agccagggca gcctccacag ctcctgatct atttggcttc taatcgggcc    180
tccggggccc ctgacaggtt cagtggcagt ggatcaggca cagattttac actgacaatc    240
agcagagtgg aggctgagga tgttggaatt tattactgca tggaagctct acaaactcct    300
cccactttcg gcggagggac caaggtggag atcaaa                              336
```

<210> SEQ ID NO 221

<400> SEQUENCE: 221

000

<210> SEQ ID NO 222
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 222

```
cagtctgtgc tgacgcagtc gccctcagtg tctggggccc cagggcagag ggtcaccatc      60
tcctgcactg ggaccagctc aacatcgggg gcaggttatg atgtacactg gtatcagcag    120
tttcctggaa cagcccccaa actcctcatc tctcataaca ccaatcggcc ctcaggggtc    180
cctgaccgat tctctggctc caagtctggc acctcagcct ccctggccat cactgggctc    240
caggctgagg atgaggctga ttattactgc cagtcctttg acagcagcct gcggggttcc    300
agggtgttcg gcggagggac caagctgacc gtccta                              336
```

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 226

Glu Ile Val Leu Thr Gln Ser Pro Ala Thr Leu Ser Leu Ser Pro Gly
1               5                   10                  15

Asp Ser Ala Thr Leu Ser Cys Arg Ala Ser Gln Ala Val Ser Thr Thr
            20                  25                  30

Tyr Leu Ala Trp Tyr Gln Gln Thr Arg Gly Gln Ala Pro Arg Leu Leu
        35                  40                  45

Ile His Gly Thr Tyr Thr Arg Ala Ile Gly Ile Pro Asp Lys Phe Ser
    50                  55                  60

Gly Thr Gly Ser Gly Thr Asp Phe Thr Leu Thr Ile Ser Gly Leu Ala
65                  70                  75                  80

Pro Glu Asp Phe Ala Val Tyr Tyr Cys Gln Gln Tyr Ser Ser Ser Pro
                85                  90                  95

Tyr Thr Phe Gly Gln Gly Thr Lys Ile Glu Ile Thr
            100                 105

<210> SEQ ID NO 227

<400> SEQUENCE: 227

000

<210> SEQ ID NO 228
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 228

Ser Asn Glu Leu Thr Gln Ala Pro Ser Val Ser Val Ser Pro Gly Gln
1               5                   10                  15

Thr Ala Arg Ile Thr Cys Phe Gly Asp Ala Leu Ala Asn Gln Tyr Ser
            20                  25                  30

Tyr Trp Tyr Gln Arg Lys Pro Gly Gln Ala Pro Val Leu Val Ile Tyr
        35                  40                  45

Lys Asp Ser Glu Arg Pro Ser Gly Ile Pro Gln Arg Phe Ser Ala Ser
    50                  55                  60

Asn Ser Gly Thr Thr Val Thr Leu Thr Ile Thr Gly Val Gln Ala Glu
65                  70                  75                  80

Asp Glu Ala Asp Tyr Phe Cys Gln Ser Ala Asp Ser Thr Gly Ile Tyr
                85                  90                  95

Lys Val Phe Gly Gly Gly Thr Lys Leu Thr Val Leu
            100                 105

<210> SEQ ID NO 229
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 229

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Leu Ser Asp Tyr
            20                  25                  30

Tyr Met Ser Trp Ile Arg Gln Ala Pro Gly Lys Gly Leu Glu Trp Val
        35                  40                  45

Ala Tyr Ile Ser Ser His Thr Ser Thr Tyr Tyr Arg Asp Ser Val
    50                  55                  60

Lys Gly Arg Phe Thr Ile Ser Arg Asp Ser Ala Lys Lys Ser Leu Tyr
65                  70                  75                  80

Leu Gln Met Asn Ser Leu Arg Val Glu Asp Thr Ala Ile Tyr Tyr Cys
                85                  90                  95

Ala Arg Asp Trp Val Gly Gly Arg Ser Ala Tyr Ser Asp His Trp Gly
            100                 105                 110

Gln Gly Thr Leu Val Thr Val Ser Ser
        115                 120

<210> SEQ ID NO 230
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 230

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Arg Arg Pro Ala
            20                  25                  30

Phe Trp Tyr Gln Gln Lys Ser Gly Gln Ala Pro Val Leu Val Met Tyr
        35                  40                  45

Asp Asp Ser Lys Arg Pro Ser Gly Ile Pro Glu Arg Phe Ser Gly Ser
    50                  55                  60

Ser Ser Gly Thr Val Ala Thr Leu Thr Ile Ser Gly Ala Gln Val Glu
65                  70                  75                  80

Asp Glu Ala Asp Tyr His Cys Tyr Ser Thr Asp Ser Ser Gly Lys Glu
                85                  90                  95

Arg Val Phe Gly Gly Gly Thr Lys Leu Thr Val Leu
            100                 105

<210> SEQ ID NO 231
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 231

Gln Val Gln Leu Val Gln Ser Gly Ala Glu Val Lys Lys Pro Gly Ala
1               5                   10                  15

```
Ser Val Lys Ile Ser Cys Lys Ala Ser Gly Tyr Asp Phe Thr Ser Phe
            20                  25                  30

Pro Met His Trp Val Arg Leu Gly Pro Gly Gln Arg Leu Glu Trp Met
            35                  40                  45

Gly Trp Ile Ser Ala Ala Asn Gly Asn Thr Lys Tyr Ser Gln Lys Phe
        50                  55                  60

Gln Asp Arg Phe Thr Ile Thr Arg Asp Thr Ser Ala Ser Ile Val His
65                  70                  75                  80

Met Glu Leu Ser Ser Leu Arg Ser Glu Asp Thr Ala Val Tyr Tyr Cys
                85                  90                  95

Ala Arg Gly Gly Tyr Ser Ser Gly Leu Tyr Arg Tyr Ser Asn Tyr Tyr
            100                 105                 110

Tyr Gly Met Thr Val Trp Gly Gln Gly Thr Leu Val Thr Val Ser Ser
        115                 120                 125
```

<210> SEQ ID NO 232
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 232

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Glu Ser Leu Leu His Asn
            20                  25                  30

Asp Arg Lys Thr Tyr Leu Phe Trp Tyr Leu Gln Lys Pro Gly Gln Pro
        35                  40                  45

Pro Gln Leu Leu Ile Phe Gln Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Leu Gln Thr
                85                  90                  95

Thr Gln Leu Pro Leu Thr Phe Gly Gly Gly Thr Lys Val Glu Ile Lys
            100                 105                 110
```

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236
<211> LENGTH: 112
<212> TYPE: PRT
<213> ORGANISM: Artificial sequence
<220> FEATURE:

<223> OTHER INFORMATION: Synthetic polypeptide

<400> SEQUENCE: 236

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asp Gly Leu Asn Tyr Leu Asp Trp Tyr Leu Leu Lys Pro Gly Gln Pro
        35                  40                  45
Pro Gln Leu Leu Ile Tyr Leu Ala Ser Asn Arg Ala Ser Gly Ala Pro
    50                  55                  60
Asp Arg Phe Ser Gly Ser Gly Ser Gly Thr Asp Phe Thr Leu Thr Ile
65                  70                  75                  80
Ser Arg Val Glu Ala Glu Asp Val Gly Ile Tyr Tyr Cys Met Glu Ala
                85                  90                  95
Leu Gln Thr Pro Pro Thr Phe Gly Gly Gly Thr Lys Val Glu Ile Lys
            100                 105                 110

<210> SEQ ID NO 237

<400> SEQUENCE: 237

000

<210> SEQ ID NO 238
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 238

Gln Ser Val Leu Thr Gln Ser Pro Ser Val Ser Gly Ala Pro Gly Gln
1               5                   10                  15
Arg Val Thr Ile Ser Cys Thr Gly Thr Ser Ser Asn Ile Gly Ala Gly
            20                  25                  30
Tyr Asp Val His Trp Tyr Gln Gln Phe Pro Gly Thr Ala Pro Lys Leu
        35                  40                  45
Leu Ile Ser His Asn Thr Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Phe Asp Ser Ser
                85                  90                  95
Leu Arg Gly Ser Arg Val Phe Gly Gly Gly Thr Lys Leu Thr Val Leu
            100                 105                 110

<210> SEQ ID NO 239
<211> LENGTH: 8
<212> TYPE: PRT
<213> ORGANISM: Artificial sequence
<220> FEATURE:
<223> OTHER INFORMATION: Synthetic peptide

<400> SEQUENCE: 239

Gly Phe Thr Phe Ser Gly His Gly
1               5

<210> SEQ ID NO 240
<211> LENGTH: 8

```
<212> TYPE: PRT
<213> ORGANISM: Artificial sequence
<220> FEATURE:
<223> OTHER INFORMATION: Synthetic peptide

<400> SEQUENCE: 240

Ile Ser Tyr Asp Gly Ser Asn Lys
1               5

<210> SEQ ID NO 241
<211> LENGTH: 17
<212> TYPE: PRT
<213> ORGANISM: Artificial sequence
<220> FEATURE:
<223> OTHER INFORMATION: Synthetic peptide

<400> SEQUENCE: 241

Ala Arg Asp Gly Tyr Arg Asn Leu Val Leu Val Gly Trp Tyr Phe Asp
1               5                   10                  15

Leu

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249
<211> LENGTH: 8
<212> TYPE: PRT
<213> ORGANISM: Artificial sequence
```

```
<220> FEATURE:
<223> OTHER INFORMATION: Synthetic peptide

<400> SEQUENCE: 249

Gly Phe Thr Leu Ser Asp Tyr Tyr
1               5

<210> SEQ ID NO 250
<211> LENGTH: 8
<212> TYPE: PRT
<213> ORGANISM: Artificial sequence
<220> FEATURE:
<223> OTHER INFORMATION: Synthetic peptide

<400> SEQUENCE: 250

Ile Ser Ser Ser His Thr Ser Thr
1               5

<210> SEQ ID NO 251
<211> LENGTH: 14
<212> TYPE: PRT
<213> ORGANISM: Artificial sequence
<220> FEATURE:
<223> OTHER INFORMATION: Synthetic peptide

<400> SEQUENCE: 251

Ala Arg Asp Trp Val Gly Gly Arg Ser Ala Tyr Ser Asp His
1               5                   10

<210> SEQ ID NO 252
<211> LENGTH: 8
<212> TYPE: PRT
<213> ORGANISM: Artificial sequence
<220> FEATURE:
<223> OTHER INFORMATION: Synthetic peptide

<400> SEQUENCE: 252

Gly Tyr Asp Phe Thr Ser Phe Pro
1               5

<210> SEQ ID NO 253
<211> LENGTH: 8
<212> TYPE: PRT
<213> ORGANISM: Artificial sequence
<220> FEATURE:
<223> OTHER INFORMATION: Synthetic peptide

<400> SEQUENCE: 253

Ile Ser Ala Ala Asn Gly Asn Thr
1               5

<210> SEQ ID NO 254
<211> LENGTH: 21
<212> TYPE: PRT
<213> ORGANISM: Artificial sequence
<220> FEATURE:
<223> OTHER INFORMATION: Synthetic peptide

<400> SEQUENCE: 254

Ala Arg Gly Gly Tyr Ser Ser Gly Leu Tyr Arg Tyr Ser Asn Tyr Tyr
1               5                   10                  15

Tyr Gly Met Thr Val
            20

<210> SEQ ID NO 255
```

```
<400> SEQUENCE: 255
000

<210> SEQ ID NO 256
<400> SEQUENCE: 256
000

<210> SEQ ID NO 257
<400> SEQUENCE: 257
000

<210> SEQ ID NO 258
<400> SEQUENCE: 258
000

<210> SEQ ID NO 259
<400> SEQUENCE: 259
000

<210> SEQ ID NO 260
<400> SEQUENCE: 260
000

<210> SEQ ID NO 261
<400> SEQUENCE: 261
000

<210> SEQ ID NO 262
<400> SEQUENCE: 262
000

<210> SEQ ID NO 263
<400> SEQUENCE: 263
000

<210> SEQ ID NO 264
<400> SEQUENCE: 264
000

<210> SEQ ID NO 265
<400> SEQUENCE: 265
000

<210> SEQ ID NO 266
<400> SEQUENCE: 266
```

```
<210> SEQ ID NO 267
<211> LENGTH: 7
<212> TYPE: PRT
<213> ORGANISM: Artificial sequence
<220> FEATURE:
<223> OTHER INFORMATION: Synthetic peptide

<400> SEQUENCE: 267

Gln Ala Val Ser Thr Thr Tyr
1               5

<210> SEQ ID NO 268
<211> LENGTH: 3
<212> TYPE: PRT
<213> ORGANISM: Artificial sequence
<220> FEATURE:
<223> OTHER INFORMATION: Synthetic peptide

<400> SEQUENCE: 268

Gly Thr Tyr
1

<210> SEQ ID NO 269
<211> LENGTH: 9
<212> TYPE: PRT
<213> ORGANISM: Artificial sequence
<220> FEATURE:
<223> OTHER INFORMATION: Synthetic peptide

<400> SEQUENCE: 269

Gln Gln Tyr Ser Ser Ser Pro Tyr Thr
1               5

<210> SEQ ID NO 270
<211> LENGTH: 6
<212> TYPE: PRT
<213> ORGANISM: Artificial sequence
<220> FEATURE:
<223> OTHER INFORMATION: Synthetic peptide

<400> SEQUENCE: 270

Ala Leu Ala Asn Gln Tyr
1               5

<210> SEQ ID NO 271
<211> LENGTH: 3
<212> TYPE: PRT
<213> ORGANISM: Artificial sequence
<220> FEATURE:
<223> OTHER INFORMATION: Synthetic peptide

<400> SEQUENCE: 271

Lys Asp Ser
1

<210> SEQ ID NO 272
<211> LENGTH: 11
<212> TYPE: PRT
<213> ORGANISM: Artificial sequence
<220> FEATURE:
<223> OTHER INFORMATION: Synthetic peptide

<400> SEQUENCE: 272

Gln Ser Ala Asp Ser Thr Gly Ile Tyr Lys Val
1               5                   10
```

```
<210> SEQ ID NO 273
<211> LENGTH: 6
<212> TYPE: PRT
<213> ORGANISM: Artificial sequence
<220> FEATURE:
<223> OTHER INFORMATION: Synthetic peptide

<400> SEQUENCE: 273

Ala Leu Pro Arg Arg Pro
1               5

<210> SEQ ID NO 274
<211> LENGTH: 3
<212> TYPE: PRT
<213> ORGANISM: Artificial sequence
<220> FEATURE:
<223> OTHER INFORMATION: Synthetic peptide

<400> SEQUENCE: 274

Asp Asp Ser
1

<210> SEQ ID NO 275
<211> LENGTH: 11
<212> TYPE: PRT
<213> ORGANISM: Artificial sequence
<220> FEATURE:
<223> OTHER INFORMATION: Synthetic peptide

<400> SEQUENCE: 275

Tyr Ser Thr Asp Ser Ser Gly Lys Glu Arg Val
1               5                   10

<210> SEQ ID NO 276
<211> LENGTH: 11
<212> TYPE: PRT
<213> ORGANISM: Artificial sequence
<220> FEATURE:
<223> OTHER INFORMATION: Synthetic peptide

<400> SEQUENCE: 276

Glu Ser Leu Leu His Asn Asp Arg Lys Thr Tyr
1               5                   10

<210> SEQ ID NO 277
<211> LENGTH: 3
<212> TYPE: PRT
<213> ORGANISM: Artificial sequence
<220> FEATURE:
<223> OTHER INFORMATION: Synthetic peptide

<400> SEQUENCE: 277

Gln Val Ser
1

<210> SEQ ID NO 278
<211> LENGTH: 9
<212> TYPE: PRT
<213> ORGANISM: Artificial sequence
<220> FEATURE:
<223> OTHER INFORMATION: Synthetic peptide

<400> SEQUENCE: 278

Leu Gln Thr Thr Gln Leu Pro Leu Thr
1               5
```

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282
<211> LENGTH: 11
<212> TYPE: PRT
<213> ORGANISM: Artificial sequence
<220> FEATURE:
<223> OTHER INFORMATION: Synthetic peptide

<400> SEQUENCE: 282

Gln Ser Leu Leu His Ser Asp Gly Leu Asn Tyr
1               5                   10

<210> SEQ ID NO 283
<211> LENGTH: 3
<212> TYPE: PRT
<213> ORGANISM: Artificial sequence
<220> FEATURE:
<223> OTHER INFORMATION: Synthetic peptide

<400> SEQUENCE: 283

Leu Ala Ser
1

<210> SEQ ID NO 284
<211> LENGTH: 9
<212> TYPE: PRT
<213> ORGANISM: Artificial sequence
<220> FEATURE:
<223> OTHER INFORMATION: Synthetic peptide

<400> SEQUENCE: 284

Met Glu Ala Leu Gln Thr Pro Pro Thr
1               5

<210> SEQ ID NO 285
<211> LENGTH: 9
<212> TYPE: PRT
<213> ORGANISM: Artificial sequence
<220> FEATURE:
<223> OTHER INFORMATION: Synthetic peptide

<400> SEQUENCE: 285

Ser Ser Asn Ile Gly Ala Gly Tyr Asp
1               5

<210> SEQ ID NO 286
<211> LENGTH: 3
<212> TYPE: PRT
<213> ORGANISM: Artificial sequence
<220> FEATURE:

<223> OTHER INFORMATION: Synthetic peptide

<400> SEQUENCE: 286

His Asn Thr
1

<210> SEQ ID NO 287
<211> LENGTH: 12
<212> TYPE: PRT
<213> ORGANISM: Artificial sequence
<220> FEATURE:
<223> OTHER INFORMATION: Synthetic peptide

<400> SEQUENCE: 287

Gln Ser Phe Asp Ser Ser Leu Arg Gly Ser Arg Val
1               5                   10

<210> SEQ ID NO 288
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 288
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattgggaa atcaatcata gtggaagcac caactacaac      180
ccgtccctca gagtcgagt caccatatca gtagacacgt ccaagaacca gttctccctg     240
aagctgagct ctgtgaccgc cgcggacacg gctgtgtatt actgtgcgag aggcttaatg     300
gacgtctggg gccaagggac cctggtcacc gtctcctca                            339

<210> SEQ ID NO 289
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 289
gccatccgga tgacccagtc tccatcctca ttctctgcat ctacaggaga cagagtcacc      60
atcacttgtc gggcgagtca gggtattagc agttatttag cctggtatca gcaaaaacca     120
gggaaagccc ctaagctcct gatctatgct gcatccactt tgcaaagtgg ggtcccatca     180
aggttcagcg gcagtggatc tgggacagat ttcactctca ccatcagctg cctgcagtct     240
gaagattttg caacttatta ctgtcaacag tattatagtt accctcgcac ttttggccag     300
gggaccaagc tggagatcaa ac                                               322

<210> SEQ ID NO 290
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 290
caggtgcagc tggtggagtc tgggggaggc gtggtccagc ctgggaggtc cctgagactc      60
tcctgtgcag cctctggatt caccttcagt agctatgcta tgcactgggt ccgccaggct     120
ccaggcaagg ggctagagtg ggtggcagtt atatcatatg atggaagtaa taaatactac     180

```
gcagactccg tgaagggccg attcaccatc tccagagaca attccaagaa cacgctgtat    240
ctgcaaatga acagcctgag agctgaggac acggctgtgt attactgtgc gaggtcagtt    300
attgggtact actactacgg tatggacgtc tggggccaag gaccctggt caccgtctcc    360 tca                                                                 363

<210> SEQ ID NO 291
<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 291
cagcctgtgc tgactcagcc accttctgca tcagcctccc tgggagcctc ggtcacactc     60
acctgcaccc tgagcagcgg ctacagtaat tataaagtgg actggtacca gcagagacca    120 ggaagggcc cccggtttgt gatgcgagtg ggcactggtg ggattgtggg atccaagggg    180
gatggcatcc ctgatcgctt ctcagtcttg ggctcaggcc tgaatcggta cctgaccatc    240
aagaacatcc aggaagagga tgagagtgac taccactgtg gggcagacca tggcagtggg    300
atcctattcg gcggagggac caagctgacc gtcctag                             337

<210> SEQ ID NO 292
<211> LENGTH: 367
<212> TYPE: DNA
<213> ORGANISM: Artificial sequence
<220> FEATURE:
<223> OTHER INFORMATION: Synthetic oligonucleotide

<400> SEQUENCE: 292
caggtgcagc tggtggagtc tgggggaggc gtggtccagc ctgggcggtc cctgagactc     60
tcctgtgcag cctctggatt cactttcagt acctacggca tgaactgggt ccgccaggct    120
ccaggcaggg gactggagtg ggtggcagat atatcatatg atggaagtaa tagtcgctat    180
gcagactccg tgaagggccg attcaccatc tccagagaca attccaagaa cacgctatct    240
ctgcagatga acgcctgag aactgaggac acggctgtgt attattgtgc gaaagattgg    300
tatttggcaa tggctggtgc agcttttgac tcctggggcc cggaaccct ggtcaccgtc    360 tcctcag                                                             367

<210> SEQ ID NO 293
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 293
tcttctgagc tgactcagga ccctgttgtg tctgtggcct tgggacagac agtcaggatc     60
acatgccaag agacagcct cacaaccttt tatgcaagct ggttccagca gaagccagga    120 caggccctg cacttgtcct gtatggtaac gacaaccggc cctcagggat cccagaccga    180
ttctctggct ccaggtcagg aaacacagct tccttgacca tcactggggc tcaggcggaa    240
gatgaggctg actattactg taactcccgg gacagcagtg gtaaaccctc attcggcgga    300
gggaccaagc tgaccgtcct aa                                             322

<210> SEQ ID NO 294
```

```
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 294
caggtgcagc tggtggagtc tgggggaggc gtggtccagc ctggagggtc cctgagactc    60
tcctgcgcag cctctggatt caccttcaca aaatatggca tgcactgggt ccgccaggct   120
ccaggcaagg ggctggagtg ggtggctttt atagcatatg atggaagtgt taaatattat   180
ggagactccg cgaagggccg attcgccatt tccagagaca atcccaagaa tacagtatat   240
ctgcaaatga acagcctgag agcagaagac acggctgtat attattgtgc gaaagtggag   300
atacactatt attcgaatag tctcttaggt atggacgtct ggggccaagg gaccctggtc   360
accgtctcct ca                                                       372

<210> SEQ ID NO 295
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 295
cagtctgtgc tgactcagcc accctcagcg tctgggaccc ccgggcagag ggtcaccatc    60
tcttgttctg gaggcaactc caacatcgga attagttatg tgtactggta ccagcatctc   120
ccaggaacgg ccccccaaact cctcatatct aaaaataatc gcggccctc aggggtccct   180 gaccgattct ctgcctccaa gtctggcact tcagcctccc tggccatcag tggactccgg   240
tccgaggatg aggctgaata ttactgtgca acattggata tcaatatgac ctgggtattc   300
ggcggaggga ccaagctgac cgtccta                                       327

<210> SEQ ID NO 296
<211> LENGTH: 352
<212> TYPE: DNA
<213> ORGANISM: Artificial sequence
<220> FEATURE:
<223> OTHER INFORMATION: Synthetic oligonucleotide

<400> SEQUENCE: 296
caggtgcagc tggtggagtc tgggggaggc gtggtccagc ctggagggtc cctgcgactc    60
tcctgtgcag cctctggatt caccttcagt ggctcttcac tgcactgggt ccgccaggct   120
ccaggcaagg ggctggagtg ggtggcagct atatcatatg atggaactaa tacatactat   180
gcagactccg tgaagggccg attcaccctc tccagagaca attccaagaa cacgctgtat   240
ctgcagatga acagcctgag agctgaggac acggctgtgt attactgtgc gaaaccagtc   300 cttttccccct tgactactg gggccaggga accctggtca ccgtctcctc ag           352

<210> SEQ ID NO 297
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 297
cagtctgccc tgactcagcc tgcctccgtg tctgggtctc ctggacagtc gatcaccatc    60
tcctgcactg gaaccagcag tgacgttggt ggttataatt atgtttcctg gtaccaacaa   120
```

```
cacccaggca aagcccccaa actcttgatt tatgaggtca gtaatcggcc ctcagggctt    180
tctagacgct tctctggctc caagtctggc aacacggcct ccctgaccat ctctgggctc    240
caggctgagg acgaggctga ttattactgc tgctcatata ccagcagcag cactgaggtg    300
ttcggcggag ggaccaagct gaccgtccta g                                   331
```

<210> SEQ ID NO 298
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 298

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Leu Met Asp Val Trp Gly Gln Gly Thr Leu Val Thr Val Ser
            100                 105                 110

Ser
```

<210> SEQ ID NO 299
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 299

```
Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro Arg
                85                  90                  95

Thr Phe Gly Gln Gly Thr Lys Leu Glu Ile Lys
            100                 105
```

<210> SEQ ID NO 300
<211> LENGTH: 121
<212> TYPE: PRT
<213> ORGANISM: Artificial sequence
<220> FEATURE:

<223> OTHER INFORMATION: Synthetic polypeptide

<400> SEQUENCE: 300

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Ala Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Val Ile Gly Tyr Tyr Tyr Gly Met Asp Val Trp Gly
            100                 105                 110
Gln Gly Thr Leu Val Thr Val Ser Ser
            115                 120
```

<210> SEQ ID NO 301
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 301

```
Gln Pro Val Leu Thr Gln Pro Pro Ser Ala Ser Ala Ser Leu Gly Ala
1               5                   10                  15
Ser Val Thr Leu Thr Cys Thr Leu Ser Ser Gly Tyr Ser Asn Tyr Lys
            20                  25                  30
Val Asp Trp Tyr Gln Gln Arg Pro Gly Lys Gly Pro Arg Phe Val Met
        35                  40                  45
Arg Val Gly Thr Gly Gly Ile Val Gly Ser Lys Gly Asp Gly Ile Pro
    50                  55                  60
Asp Arg Phe Ser Val Leu Gly Ser Gly Leu Asn Arg Tyr Leu Thr Ile
65                  70                  75                  80
Lys Asn Ile Gln Glu Glu Asp Glu Ser Asp Tyr His Cys Gly Ala Asp
                85                  90                  95
His Gly Ser Gly Ile Leu Phe Gly Gly Gly Thr Lys Leu Thr Val Leu
            100                 105                 110
```

<210> SEQ ID NO 302
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 302

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Thr Tyr
            20                  25                  30
Gly Met Asn Trp Val Arg Gln Ala Pro Gly Arg Gly Leu Glu Trp Val
        35                  40                  45
Ala Asp Ile Ser Tyr Asp Gly Ser Asn Ser Arg Tyr Ala Asp Ser Val
```

```
                    50                  55                  60
Lys Gly Arg Phe Thr Ile Ser Arg Asp Asn Ser Lys Asn Thr Leu Ser
 65                  70                  75                  80

Leu Gln Met Asn Gly Leu Arg Thr Glu Asp Thr Ala Val Tyr Tyr Cys
                 85                  90                  95

Ala Lys Asp Trp Tyr Leu Ala Met Ala Gly Ala Ala Phe Asp Ser Trp
            100                 105                 110

Gly Pro Gly Thr Leu Val Thr Val Ser Ser
            115                 120
```

<210> SEQ ID NO 303
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 303

```
Ser Ser Glu Leu Thr Gln Asp Pro Val Val Ser Val Ala Leu Gly Gln
  1               5                  10                  15

Thr Val Arg Ile Thr Cys Gln Gly Asp Ser Leu Thr Thr Phe Tyr Ala
                 20                  25                  30

Ser Trp Phe Gln Gln Lys Pro Gly Gln Ala Pro Ala Leu Val Leu Tyr
             35                  40                  45

Gly Asn Asp Asn Arg Pro Ser Gly Ile Pro Asp Arg Phe Ser Gly Ser
         50                  55                  60

Arg Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Lys Pro
                 85                  90                  95

Ser Phe Gly Gly Gly Thr Lys Leu Thr Val Leu
            100                 105
```

<210> SEQ ID NO 304
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 304

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Thr Lys Tyr
                 20                  25                  30

Gly Met His Trp Val Arg Gln Ala Pro Gly Lys Gly Leu Glu Trp Val
             35                  40                  45

Ala Phe Ile Ala Tyr Asp Gly Ser Val Lys Tyr Tyr Gly Asp Ser Ala
         50                  55                  60

Lys Gly Arg Phe Ala Ile Ser Arg Asp Asn Pro Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Lys Val Glu Ile His Tyr Tyr Ser Asn Ser Leu Leu Gly Met Asp
            100                 105                 110

Val Trp Gly Gln Gly Thr Leu Val Thr Val Ser Ser
            115                 120
```

<210> SEQ ID NO 305
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 305

Gln Ser Val Leu Thr Gln Pro Pro Ser Ala Ser Gly Thr Pro Gly Gln
1               5                   10                  15

Arg Val Thr Ile Ser Cys Ser Gly Gly Asn Ser Asn Ile Gly Ile Ser
            20                  25                  30

Tyr Val Tyr Trp Tyr Gln His Leu Pro Gly Thr Ala Pro Lys Leu Leu
        35                  40                  45

Ile Ser Lys Asn Asn Leu Arg Pro Ser Gly Val Pro Asp Arg Phe Ser
    50                  55                  60

Ala Ser Lys Ser Gly Thr Ser Ala Ser Leu Ala Ile Ser Gly Leu Arg
65                  70                  75                  80

Ser Glu Asp Glu Ala Glu Tyr Tyr Cys Ala Thr Leu Asp Ile Asn Met
                85                  90                  95

Thr Trp Val Phe Gly Gly Gly Thr Lys Leu Thr Val Leu
            100                 105

<210> SEQ ID NO 306
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 306

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Ser
            20                  25                  30

Ser Leu His Trp Val Arg Gln Ala Pro Gly Lys Gly Leu Glu Trp Val
        35                  40                  45

Ala Ala Ile Ser Tyr Asp Gly Thr Asn Thr Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Val Leu Ser Pro Phe Asp Tyr Trp Gly Gln Gly Thr Leu
            100                 105                 110

Val Thr Val Ser Ser
        115

<210> SEQ ID NO 307
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 307

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr

```
                20                  25                  30
Asn Tyr Val Ser Trp Tyr Gln Gln His Pro Gly Lys Ala Pro Lys Leu
            35                  40                  45

Leu Ile Tyr Glu Val Ser Asn Arg Pro Ser Gly Val Ser Arg Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Thr Ser Ser
                85                  90                  95

Ser Thr Glu Val Phe Gly Gly Gly Thr Lys Leu Thr Val Leu
            100                 105                 110
```

<210> SEQ ID NO 308
<211> LENGTH: 8
<212> TYPE: PRT
<213> ORGANISM: Artificial sequence
<220> FEATURE:
<223> OTHER INFORMATION: Synthetic peptide

<400> SEQUENCE: 308

```
Gly Gly Ser Phe Ser Gly Tyr Tyr
1               5
```

<210> SEQ ID NO 309
<211> LENGTH: 7
<212> TYPE: PRT
<213> ORGANISM: Artificial sequence
<220> FEATURE:
<223> OTHER INFORMATION: Synthetic peptide

<400> SEQUENCE: 309

```
Ile Asn His Ser Gly Ser Thr
1               5
```

<210> SEQ ID NO 310
<211> LENGTH: 7
<212> TYPE: PRT
<213> ORGANISM: Artificial sequence
<220> FEATURE:
<223> OTHER INFORMATION: Synthetic peptide

<400> SEQUENCE: 310

```
Ala Arg Gly Leu Met Asp Val
1               5
```

<210> SEQ ID NO 311
<211> LENGTH: 8
<212> TYPE: PRT
<213> ORGANISM: Artificial sequence
<220> FEATURE:
<223> OTHER INFORMATION: Synthetic peptide

<400> SEQUENCE: 311

```
Gly Phe Thr Phe Ser Ser Tyr Ala
1               5
```

<210> SEQ ID NO 312
<211> LENGTH: 8
<212> TYPE: PRT
<213> ORGANISM: Artificial sequence
<220> FEATURE:
<223> OTHER INFORMATION: Synthetic peptide

<400> SEQUENCE: 312

Ile Ser Tyr Asp Gly Ser Asn Lys
1               5

<210> SEQ ID NO 313
<211> LENGTH: 14
<212> TYPE: PRT
<213> ORGANISM: Artificial sequence
<220> FEATURE:
<223> OTHER INFORMATION: Synthetic peptide

<400> SEQUENCE: 313

Ala Arg Ser Val Ile Gly Tyr Tyr Tyr Tyr Gly Met Asp Val
1               5                   10

<210> SEQ ID NO 314
<211> LENGTH: 8
<212> TYPE: PRT
<213> ORGANISM: Artificial sequence
<220> FEATURE:
<223> OTHER INFORMATION: Synthetic peptide

<400> SEQUENCE: 314

Gly Phe Thr Phe Ser Thr Tyr Gly
1               5

<210> SEQ ID NO 315
<211> LENGTH: 8
<212> TYPE: PRT
<213> ORGANISM: Artificial sequence
<220> FEATURE:
<223> OTHER INFORMATION: Synthetic peptide

<400> SEQUENCE: 315

Ile Ser Tyr Asp Gly Ser Asn Ser
1               5

<210> SEQ ID NO 316
<211> LENGTH: 15
<212> TYPE: PRT
<213> ORGANISM: Artificial sequence
<220> FEATURE:
<223> OTHER INFORMATION: Synthetic peptide

<400> SEQUENCE: 316

Ala Lys Asp Trp Tyr Leu Ala Met Ala Gly Ala Ala Phe Asp Ser
1               5                   10                  15

<210> SEQ ID NO 317
<211> LENGTH: 8
<212> TYPE: PRT
<213> ORGANISM: Artificial sequence
<220> FEATURE:
<223> OTHER INFORMATION: Synthetic peptide

<400> SEQUENCE: 317

Gly Phe Thr Phe Thr Lys Tyr Gly
1               5

<210> SEQ ID NO 318
<211> LENGTH: 8
<212> TYPE: PRT
<213> ORGANISM: Artificial sequence
<220> FEATURE:
<223> OTHER INFORMATION: Synthetic peptide

<400> SEQUENCE: 318

Ile Ala Tyr Asp Gly Ser Val Lys

```
1               5

<210> SEQ ID NO 319
<211> LENGTH: 16
<212> TYPE: PRT
<213> ORGANISM: Artificial sequence
<220> FEATURE:
<223> OTHER INFORMATION: Synthetic peptide

<400> SEQUENCE: 319

Ala Lys Val Glu Ile His Tyr Tyr Ser Asn Ser Leu Leu Gly Met Asp
1               5                   10                  15

<210> SEQ ID NO 320
<211> LENGTH: 8
<212> TYPE: PRT
<213> ORGANISM: Artificial sequence
<220> FEATURE:
<223> OTHER INFORMATION: Synthetic peptide

<400> SEQUENCE: 320

Gly Phe Thr Phe Ser Gly Ser Ser
1               5

<210> SEQ ID NO 321
<211> LENGTH: 8
<212> TYPE: PRT
<213> ORGANISM: Artificial sequence
<220> FEATURE:
<223> OTHER INFORMATION: Synthetic peptide

<400> SEQUENCE: 321

Ile Ser Tyr Asp Gly Thr Asn Thr
1               5

<210> SEQ ID NO 322
<211> LENGTH: 10
<212> TYPE: PRT
<213> ORGANISM: Artificial sequence
<220> FEATURE:
<223> OTHER INFORMATION: Synthetic peptide

<400> SEQUENCE: 322

Ala Lys Pro Val Leu Ser Pro Phe Asp Tyr
1               5                   10

<210> SEQ ID NO 323
<211> LENGTH: 6
<212> TYPE: PRT
<213> ORGANISM: Artificial sequence
<220> FEATURE:
<223> OTHER INFORMATION: Synthetic peptide

<400> SEQUENCE: 323

Gln Gly Ile Ser Ser Tyr
1               5

<210> SEQ ID NO 324
<211> LENGTH: 3
<212> TYPE: PRT
<213> ORGANISM: Artificial sequence
<220> FEATURE:
<223> OTHER INFORMATION: Synthetic peptide

<400> SEQUENCE: 324

Ala Ala Ser
1
```

```
<210> SEQ ID NO 325
<211> LENGTH: 9
<212> TYPE: PRT
<213> ORGANISM: Artificial sequence
<220> FEATURE:
<223> OTHER INFORMATION: Synthetic peptide

<400> SEQUENCE: 325

Gln Gln Tyr Tyr Ser Tyr Pro Arg Thr
1               5

<210> SEQ ID NO 326
<211> LENGTH: 7
<212> TYPE: PRT
<213> ORGANISM: Artificial sequence
<220> FEATURE:
<223> OTHER INFORMATION: Synthetic peptide

<400> SEQUENCE: 326

Ser Gly Tyr Ser Asn Tyr Lys
1               5

<210> SEQ ID NO 327
<211> LENGTH: 8
<212> TYPE: PRT
<213> ORGANISM: Artificial sequence
<220> FEATURE:
<223> OTHER INFORMATION: Synthetic peptide

<400> SEQUENCE: 327

Val Gly Thr Gly Gly Ile Val Gly
1               5

<210> SEQ ID NO 328
<211> LENGTH: 9
<212> TYPE: PRT
<213> ORGANISM: Artificial sequence
<220> FEATURE:
<223> OTHER INFORMATION: Synthetic peptide

<400> SEQUENCE: 328

Gly Ala Asp His Gly Ser Gly Ile Leu
1               5

<210> SEQ ID NO 329
<211> LENGTH: 6
<212> TYPE: PRT
<213> ORGANISM: Artificial sequence
<220> FEATURE:
<223> OTHER INFORMATION: Synthetic peptide

<400> SEQUENCE: 329

Ser Leu Thr Thr Phe Tyr
1               5

<210> SEQ ID NO 330
<211> LENGTH: 3
<212> TYPE: PRT
<213> ORGANISM: Artificial sequence
<220> FEATURE:
<223> OTHER INFORMATION: Synthetic peptide

<400> SEQUENCE: 330

Gly Asn Asp
1
```

```
<210> SEQ ID NO 331
<211> LENGTH: 10
<212> TYPE: PRT
<213> ORGANISM: Artificial sequence
<220> FEATURE:
<223> OTHER INFORMATION: Synthetic peptide

<400> SEQUENCE: 331

Asn Ser Arg Asp Ser Ser Gly Lys Pro Ser
1               5                   10

<210> SEQ ID NO 332
<211> LENGTH: 8
<212> TYPE: PRT
<213> ORGANISM: Artificial sequence
<220> FEATURE:
<223> OTHER INFORMATION: Synthetic peptide

<400> SEQUENCE: 332

Asn Ser Asn Ile Gly Ile Ser Tyr
1               5

<210> SEQ ID NO 333
<211> LENGTH: 3
<212> TYPE: PRT
<213> ORGANISM: Artificial sequence
<220> FEATURE:
<223> OTHER INFORMATION: Synthetic peptide

<400> SEQUENCE: 333

Lys Asn Asn
1

<210> SEQ ID NO 334
<211> LENGTH: 10
<212> TYPE: PRT
<213> ORGANISM: Artificial sequence
<220> FEATURE:
<223> OTHER INFORMATION: Synthetic peptide

<400> SEQUENCE: 334

Ala Thr Leu Asp Ile Asn Met Thr Trp Val
1               5                   10

<210> SEQ ID NO 335
<211> LENGTH: 9
<212> TYPE: PRT
<213> ORGANISM: Artificial sequence
<220> FEATURE:
<223> OTHER INFORMATION: Synthetic peptide

<400> SEQUENCE: 335

Ser Ser Asp Val Gly Gly Tyr Asn Tyr
1               5

<210> SEQ ID NO 336
<211> LENGTH: 3
<212> TYPE: PRT
<213> ORGANISM: Artificial sequence
<220> FEATURE:
<223> OTHER INFORMATION: Synthetic peptide

<400> SEQUENCE: 336

Glu Val Ser
1
```

```
<210> SEQ ID NO 337
<211> LENGTH: 10
<212> TYPE: PRT
<213> ORGANISM: Artificial sequence
<220> FEATURE:
<223> OTHER INFORMATION: Synthetic peptide

<400> SEQUENCE: 337

Cys Ser Tyr Thr Ser Ser Ser Thr Glu Val
1               5                   10
```

HUMAN MONOCLONAL ANTIBODIES THAT NEUTRALIZE PANDEMIC GII.4 NOROVIRUSES

PRIORITY CLAIM

This application is a national phase application under 35 U.S.C. § 371 of International Application No. PCT/US2019/048231, filed Aug. 27, 2019, which claims benefit of priority to U.S. Provisional Application Ser. No. 62/723,155, filed Aug. 27, 2018, and U.S. Provisional Application Ser. No. 62/723,565, filed Aug. 28, 2018, the entire contents of each of which are hereby incorporated by reference.

This invention was made with government support under NIH Grants P30DK058404, P01AI057788, P30CA125123 and T32GM120011 awarded by the National Institutes of Health. The government has certain rights in the invention.

BACKGROUND

1. Field of the Disclosure

The present disclosure relates generally to the fields of medicine, infectious disease, and immunology. More particular, the disclosure relates to human antibodies binding to human norovirus.

2. Background

Since the licensure and use of rotavirus vaccines, human noroviruses (HuNoV) have become the major etiologic agent of epidemic and sporadic acute gastroenteritis (Glass et al., 2009). The persistence of HuNoVs is attributed to many factors, such as a low infectious dose, extreme environmental viral stability, high levels of shedding, and prolonged shedding even after symptoms have resolved (Fields et al., 2013). According to the Centers for Disease Control and Prevention, HuNoVs cause on average 19 to 21 million cases of infection and between 570 to 800 deaths in children under the age of five each year in the United States. HuNoVs infect people of all ages and, even though infection is characteristically acute and self-limiting, disease can become life threatening in children, the elderly, and the immunocompromised (Bok and Green, 2012). The correlates of HuNoV immunity in humans are poorly incompletely understood. There are several correlates of protection that have been described; the new capacity to perform in vitro neutralization testing described here may provide an improved correlate. Antibodies are clearly important to human immunity (Atmar et al., 2018).

One of the challenges for developing antibodies or vaccines to prevent HuNoV-associated disease is the extreme antigenic diversity of field strains. HuNoVs currently are classified phylogenetically into 7 different genogroups (GI-GVII) and at least 41 different genotypes (Vinjé, 2015). Viruses from genogroup I (GI) and the rapidly evolving genogroup II (GII) account for nearly all human infections. The HuNoV genome contains 3 open reading frames (ORF1, ORF2, and ORF3). ORF1 encodes nonstructural proteins, while ORF2 and ORF3 encode the major and minor capsid proteins, respectively. In the past, HuNoVs could not be cultivated in cell culture, but the VP1 and VP2 protein sequences could be expressed using a baculovirus expression system to produce HuNoV virus-like particles (VLPs) (Jiang et al., 1992). These VLP reagents have facilitated the study of HuNoV evolution, antigenicity and the emergence of new virus strains (Richardson et al., 2013; Erdman et al., 1989).

Since the mid-1990s, viruses from genogroup II genotype 4 (GII.4) have caused the majority of outbreaks, with new strains emerging every 2-3 years (Vinjé, 2015). In 2012, the GII.4 Sydney strain emerged and since then has continued to predominate among circulating strains. The molecular basis for antibody-mediated recognition of these strains and their mechanisms of action are not well characterized.

SUMMARY

Thus, in accordance with the present disclosure, there is provided a method of detecting a norovirus infection in a subject comprising (a) contacting a sample from the subject with an antibody or antibody fragment having clone-paired heavy and light chain CDR sequences from Tables 3 and 4, respectively; and (b) detecting norovirus in the sample by binding of the antibody or antibody fragment to a norovirus antigen in the sample. The sample may be a body fluid, such as blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or Western blot. The method may further comprise performing steps (a) and (b) a second time and determining a change in norovirus antigen levels as compared to the first assay.

The antibody or antibody fragment may be encoded by clone-paired variable sequences as set forth in Table 1, may be encoded light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. Alternatively, the antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment.

In another embodiment, there is provided a method of treating a subject infected with norovirus or reducing the likelihood of infection of a subject at risk of contracting norovirus, comprising delivering to the subject an antibody or antibody fragment having clone-paired heavy and light chain CDR sequences from Tables 3 and 4, respectively. The antibody or antibody fragment may be encoded by clone-paired variable sequences as set forth in Table 1, may be encoded light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. Alternatively, the antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment.

The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. Alternatively, the antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment.

The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

In yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. Alternatively, the antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment.

The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

In still yet another embodiment, there is provided a vaccine formulation comprising one or more antibodies or antibody fragments characterized by clone-paired heavy and light chain CDR sequences from Tables 3 and 4, respectively. The antibody or antibody fragment may be encoded by clone-paired variable sequences as set forth in Table 1, may be encoded light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. Alternatively, the antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment.

The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

Also provided is vaccine formulation comprising one or more expression vectors encoding a first antibody or antibody fragment as defined above. The expression vector(s) may be Sindbis virus or VEE vector(s). The vaccine formulation may be formulated for delivery by needle injection, jet injection, or electroporation. The vaccine formulation may further comprise one or more expression vectors encoding for a second antibody or antibody fragment as defined above.

An additional embodiment includes a method of protecting the health of a placenta and/or fetus of a pregnant a subject infected with or at risk of infection with norovirus comprising delivering to the subject an antibody or antibody fragment having clone-paired heavy and light chain CDR sequences from Tables 3 and 4, respectively. The antibody or antibody fragment may be encoded by clone-paired variable sequences as set forth in Table 1, may be encoded light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. Alternatively, the antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment.

The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

The antibody or antibody fragment may be administered prior to infection or after infection. The subject may be a pregnant female, a sexually active female, or a female undergoing fertility treatments. Delivering comprises antibody or antibody fragment administration, or genetic delivery with an RNA or DNA sequence or vector encoding the antibody or antibody fragment. The antibody or antibody fragment may increase the size of the placenta as compared to an untreated control and/or may reduce viral load and/or pathology of the fetus as compared to an untreated control.

Yet another embodiment involves a method of determining the antigenic integrity, correct conformation and/or correct sequence of a norovirus antigen comprising (a) contacting a sample comprising the antigen with a first antibody or antibody fragment having clone-paired heavy and light chain CDR sequences from Tables 3 and 4, respectively; and (b) determining antigenic integrity, correct conformation and/or correct sequence of the antigen by detectable binding of the first antibody or antibody fragment to the antigen. The sample may comprise recombinantly produced antigen. The sample may comprise a vaccine formulation or vaccine production batch. Detection may comprise ELISA, RIA, western blot, a biosensor using surface plasmon resonance or biolayer interferometry, or flow cytometric staining.

The first antibody or antibody fragment may be encoded by clone-paired variable sequences as set forth in Table 1, may be encoded light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. Alternatively, the first antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The first antibody fragment may be a recombinant scFv (single chain fragment variable) antibody, Fab fragment, F(ab')$_2$ fragment, or Fv fragment. The method may further comprise performing steps (a) and (b) a second time to determine the antigenic stability of the antigen over time.

The method may further comprise (c) contacting a sample comprising the antigen with a second antibody or antibody fragment having clone-paired heavy and light chain CDR sequences from Tables 3 and 4, respectively; and (d) determining antigenic integrity of the antigen by detectable binding of the second antibody or antibody fragment to the antigen. The second antibody or antibody fragment may be encoded by clone-paired variable sequences as set forth in Table 1, may be encoded light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. Alternatively, the second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant scFv (single chain fragment variable) antibody, Fab fragment, F(ab')$_2$ fragment, or Fv fragment. The method may further comprise performing steps (c) and (d) a second time to determine the antigenic stability of the antigen over time.

Also provided is a human monoclonal antibody or antibody fragment, or hybridoma or engineered cell producing the same, wherein the antibody or antibody fragment binds to norovirus capsid protein P domain and/or S domain. The human monoclonal antibody or antibody fragment may bind to norovirus capsid protein P domain P1 or P2 subdomain. The antibody or antibody fragment may cross-react with multiple norovirus GI and/or GII strains.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-C. Neutralization of GII.4 Sydney 2012 using virus-like particles (VLPs) or live virus. (FIG. 1A) Half-maximal effective concentrations (EC$_{50}$) for all isolated IgGs and IgAs using a VLP blockade assay, and the antibody concentration at which hemagglutination was inhibited when using VLPs and O+ red blood cells. > symbols indicate blockade $EC_{50}$ values >100 µg/mL for IgGs or >113 µg/mL for IgAs, or HAI titers >15 µg/mL. (FIG. 1B) Plotted are the absorbance values when plates were read at optical density (O.D.) 450 nm for selected IgGs and IgAs when antibodies were diluted serially, combined with GII.4 Sydney 2012 VLPs and added to porcine gastric mucin (PGM). (FIG. 1C) Inhibition of replication of GII.4 Sydney 2012 virus using selected IgGs, IgAs and a non-specific human monoclonal antibody (mAb) were tested in a human intestinal enteroid system. An additional control for each experiment was virus incubated without a mAb. The half-maximal inhibitory concentration ($IC_{50}$) for each mAb is indicated in each individual graph. The data presented is an average of two independent experiments for NORO-263, -250B, -320, -273A, -318 and a dengue virus-specific control antibody 2D22. The number of genome equivalents for each concentration tested for each mAb including the no antibody control was the average of 6 replicates tested.

(FIG. 5A) $EC_{50}$ value indicates the concentration at which half-maximal binding was obtained when tested by ELISA using either recombinantly expressed P domain or shell domain as antigen. mAbs are organized by isotype, IgG or IgA, and arranged in order from lowest to highest $EC_{50}$ value when binding to GII.4 VLPs. > symbol for IgGs indicates $EC_{50}$ binding value >150 µg/ml for IgAs. Grey boxes indicate mAbs that exclusively bind to the GII.4 Sydney 2012 shell domain. (FIG. 5B) Binding of mAbs to P or S domain. Graphs are separated by antigen and mAb isotype.

FIG. 6. Competition binding of GII.4 specific mAbs on GST-GII.4 P domain using OctetR HTX System. Epitope binning was performed used biolayer interferometry. GST-tagged GII.4 Sydney 2012 P domain was loaded onto anti-GST tips, then the first antibody was loaded followed by loading of the second antibody. The numerical data has been normalized to a no-antibody buffer control and indicates percent binding of the second antibody in the presence of the first antibody. Boxes indicate potential competition binding groups.

(FIG. 8A) Listed are the $EC_{50}$ of each mAb for binding or blockade activity using GII.4 Houston VLPs. > symbols indicate blockade $EC_{50}$ values >100 µg/mL. (FIG. 8B) Serial dilutions of each mAb and a no-antibody control were used to measure blockade activity.

(FIG. 9A Half-maximal effective concentration ($EC_{50}$) for binding to VLPs of indicated genotype. Listed are the isotype, light chain and $EC_{50}$ value to GI.1, GI.2, GI.3, GII.3, GII.4, GII.6, GII.13 or GII.17 VLPs. The > symbol indicates binding was not detected at the highest concentration tested, 500 nm. Greater $EC_{50}$ values are in the lightest shade and lowest $EC_{50}$ values are in the darkest shade. (FIG. 9B) Representative ELISA binding curves are shown for indicated genotype.

(FIG. 10A) Half-maximal effective concentrations ($EC_{50}$) for cross-reactive mAbs when blocking GI or GII VLPs from binding to PGM. The > symbol indicates the blocking $EC_{50}$ value was greater than 1,000 nm. (FIG. 10B) Blockade activity was tested using serial dilutions of each mAb.

FIG. 11. Half-maximal effective concentrations ($EC_{50}$) for binding of 12 cross-reactive human mAbs to protruding or shell domain. GI.3, GII.4, GII.6 or GII.17 NoV strain protruding or shell domain proteins were used as antigen in an indirect ELISA. The > symbol indicates binding was not detected at the highest concentration tested, 500 nm. ND, not determined; P, protruding domain; S, shell domain; P/S, protruding and shell domain.

FIGS. 12A-D. NORO-320 Fab in complex with GII.4 P domain. (FIG. 12A) X-ray crystal structure of NORO-320-GII.4 P domain complex. NORO-320 Fab along with two molecules of H-type 1 pentasaccharide (stick model) modeled to indicate the glycan binding sites for reference. Depicted are side and top views of the complex. (FIG. 12B) Side view of NORO-320 in complex with GII.4 P domain showing the interacting Fab residues (stick model) interacting. (FIG. 12C) Close-up view of the Fab binding site (black-box in B) showing the P domain residues (stick models) which interact with the Fab. Residues in the two-fold related subunit is hyphenated. (FIG. 12D) Close up view of the Fab residues that interact with the GII.4 P domain (shown in surface representation).

FIGS. 13A-C. Molecular interactions between NORO-320 and GII.4 P domain. (FIG. 13A) Antibody plot analysis using the program LigPlot+v.2.1 (Laskowski et al., 2011). The P2 subdomain residues in the 2-fold related subunit are hyphenated. The hydrogen bonds are shown as green dashed lines, and the hydrophobic contacts are short spokes radiating from each atom or residue. (FIGS. 13B-C) The interactions of P1 or P2 subdomains with NORO-320. The side chains of mAb and P domain are represented with ball-and-stick and stick models, respectively, and colored as in FIG. 4. The hydrogen bonds are shown as black dashed lines.

FIG. 14. Amino acid sequence alignment of the protruding domain of GI.1, GII.3, GII.4, GII.13 and GII.17 strains of human NoV. The protruding domain amino acid sequences of GII.3, GII.4, GII.13 and GII.17, the GII strains tested for which NORO-320 exhibited reactivity, and GI.1 are aligned. Boxed are the 18 residues identified on GII.4 that interact with the highly cross-reactive mAb NORO-320 or residues previously reported to be involved in GII.4 HBGA binding (Shanker et al., 2011).

FIGS. 17A-D. Modeling of NORO-320 Fab bound to GII.4 particle. (FIG. 17A) Superimposition of GII.4 P domain/NORO-320 Fab complex onto Norwalk virus capsid (PDB ID: 1IHM). NORO-320 Fab is shown in surface representation with light chain and heavy chain. (FIG. 17B-C) Close-up views of a VP1 dimer with two molecules of NORO-320 Fab. (FIG. 17D) A schematic of proposed model for the neutralization of GII strains by NORO-320 IgA.

TABLE A

Figure 2:
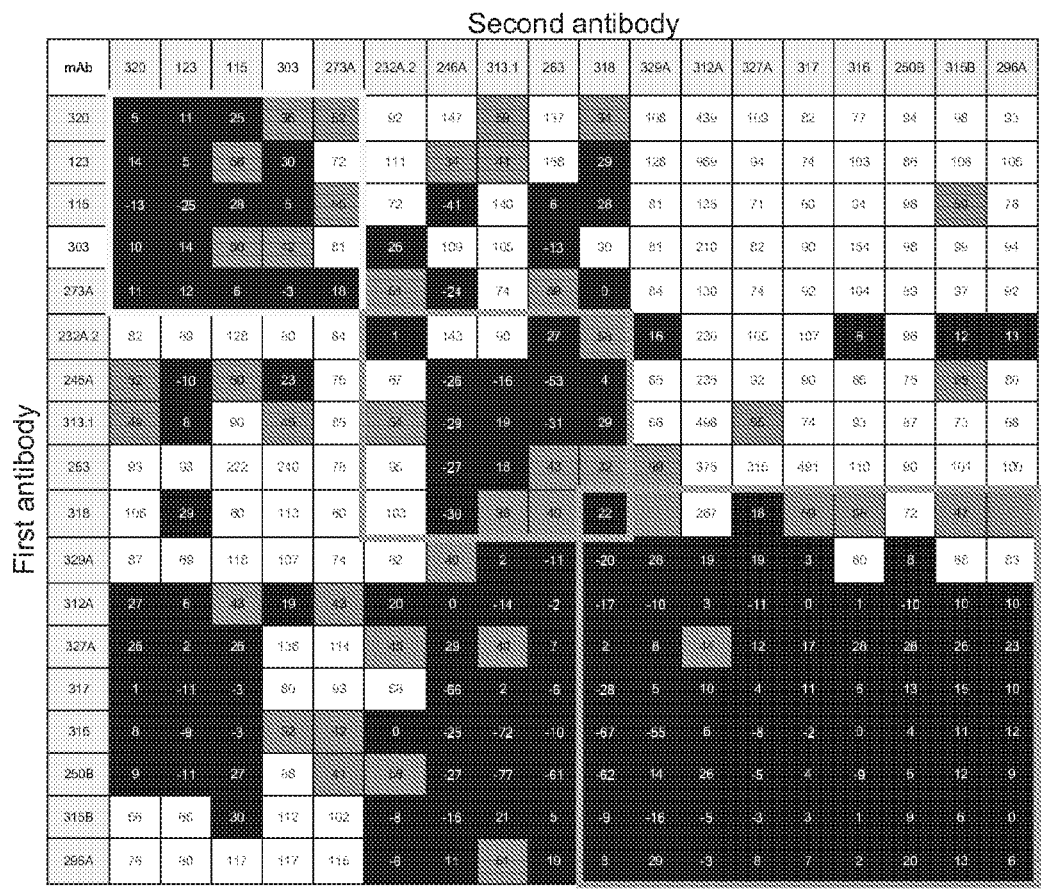
FIG. 2. Competition binding of GII.4 specific mAbs on GII.4 Sydney 2012 P domain with the Octet® Red96 system. Epitope binning was performed using biolayer interferometry. GST-tagged GII.4 Sydney 2012 P domain was loaded onto anti-GST tips, then the first antibody was loaded followed by loading of the second antibody. The numerical data indicate percent binding of the second antibody in the presence of the first antibody. Boxes indicate potential binding groups.
Figure 3:
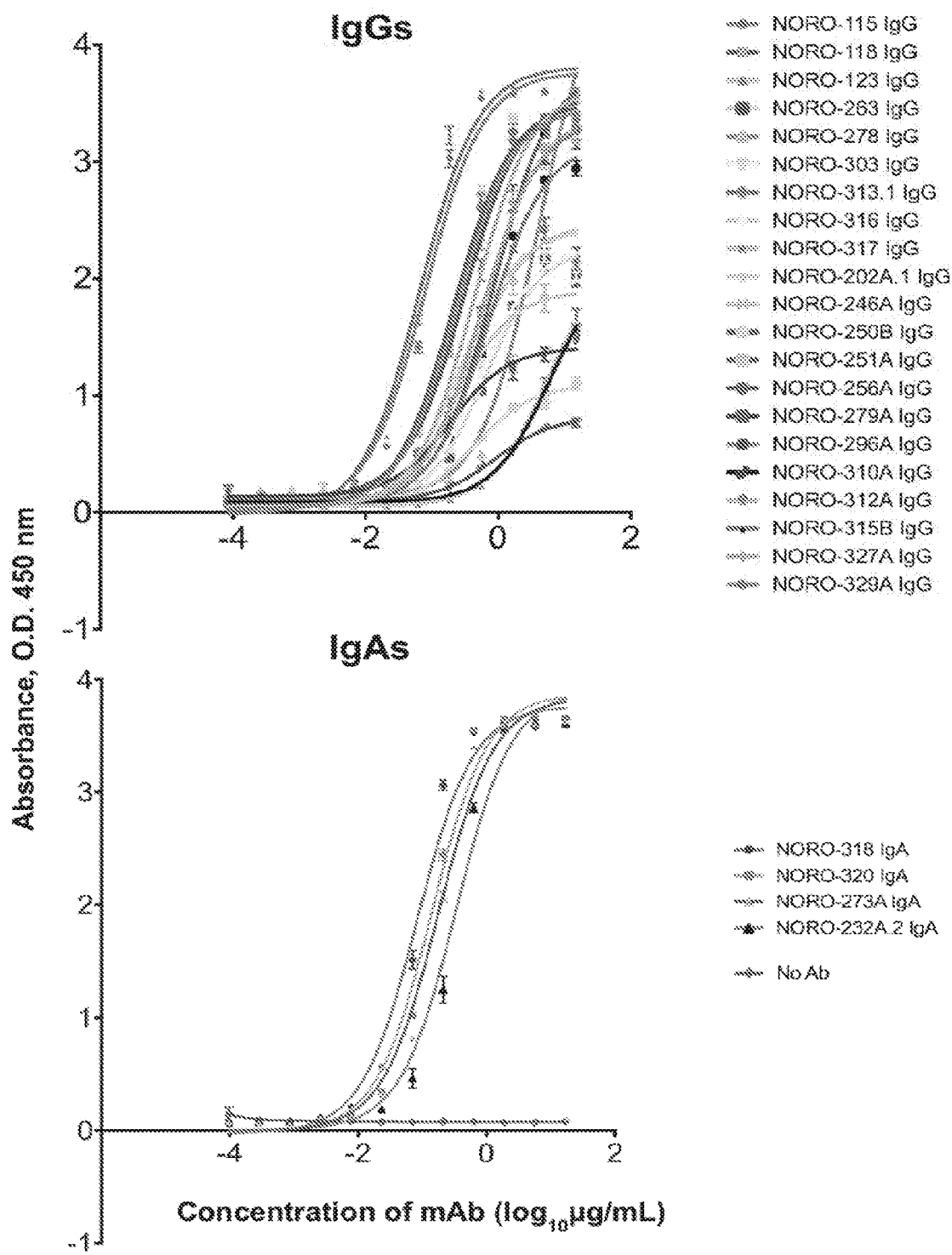
FIG. 3. Characterization of human mAb binding to GII.4 Syndey VLPs. Reactivity of serially diluted mAbs or a no-antibody control for GII.4 Sydney 2012 test by ELISA.

Isotype, light chain and ELISA binding characterization of GII.4 P VLP-specific human mAbs.

| Isotype | mAb clone NORO- | Light chain | $EC_{50}$ (μg/mL) |
|---|---|---|---|
| IgG | 115 | κ | 0.1 |
| | 313.1 | κ | 0.1 |
| | 246A | λ | 0.2 |
| | 250B | λ | 0.2 |
| | 279A | λ | 0.2 |
| | 329A | λ | 0.2 |
| | 118 | λ | 0.3 |
| | 316 | λ | 0.3 |
| | 202A.1 | λ | 0.4 |
| | 312A | λ | 0.4 |
| | 317 | λ | 0.4 |
| | 303 | λ | 0.5 |
| | 263 | λ | 0.6 |
| | 296A | λ | 0.6 |
| | 327A | λ | 0.6 |
| | 315B | λ | 0.7 |
| | 251A | λ | 0.9 |
| | 256A | λ | 0.9 |
| | 278 | λ | 4.0 |
| | 123 | λ | 5.4 |
| | 310A | κ | 6.2 |
| IgA | 318 | κ | 0.1 |
| | 320 | κ | 0.1 |
| | 273A | κ | 0.2 |
| | 232A.2 | κ | 0.3 |

Isotype, light chain and ELISA binding characterization of GII.4 P VLP-specific human mAbs. Listed are the half-maximal concentrations (EC50) at which half-maximal binding was obtained when tested by ELISA using VLPs as the antigen. MAbs are organized by isotype (IgG or IgA) and arranged in order from lowest to highest EC50 value when binding to GII.4 VLPs.

Supplementary Table 1.
Antibody variable gene usage for GII.4 Sydney 2012 VLP-binding mAbs; Heavy Chain.

| | | | | Heavy Chain | | | | | |
|---|---|---|---|---|---|---|---|---|---|
| Donor | NORO mAb clone | isotype/ Light chain | V gene | V gene % identity | J gene | J gene % identity | D gene | Junction (SEQ ID NO:) | HCDR length |
| HD329 | 115 | IgG/K | V3-11*01 F | 89.2 | J5*02 F | 94.1 | D6-13*01 F | CARDRLPASGSHWFHPW (171) | 8.8.15 |
| HD331 | 313.1 | IgG/K | V3-11*06 F | 92.7 | J6*02 F | 80.7 | D1-1*01 F | CARMGRLELERRPHYYYPLDVW (172) | 8.8.20 |
| HD334 | 250B | IgG/A | V3-11*06 F | 95.5 | J4*02 F | 97.9 | D1-26*01 F | CARATSQGATSYYFDSW (173) | 8.8.15 |
| HD337 | 279A | IgG/A | V3-30*03 F | 91.7 | J6*02 F | 79.0 | D2-8*01 F | CAKVEIHYYSNSLLGMDVW (174) | 8.8.17 |
| HD331 | 329A | IgG/A | V3-11*06 F | 96.2 | J4*02 F | 91.7 | D3-10*01 F | CARYNYYGSGSFVFDYW (175) | 8.8.15 |
| 990 | 202A.1 | IgG/A | V1-2*02 F | 93.3 | J3*01 F | 92.0 | D7-27*01 F | CARDLLRNWGDHDAFDVW (176) | 8.7.16 |
| HD331 | 312A | IgG/A | V3-11*06 F | 94.1 | J4*02 F | 89.6 | D2-15*01 F | CARDAQYCSGGRCYLVFDYW (177) | 8.8.18 |
| HD331 | 317 | IgG/A | V4-34*01 F | 91.2 | J5*02 F | 90.0 | D3-16*02 F | CARGOMRTRGALFRRFDPW (178) | 8.7.17 |
| HD333 | 303 | IgG/K | V3-30*01 F | 97.6 | J6*02 F | 80.7 | D3-10*01 F | CARDCRVGWVFTYGMDVW (179) | 8.8.16 |
| HD333 | 296A | IgG/A | V3-11*05 F | 95.1 | J1*01 F | 86.3 | D3-10*01 F | CARYGAEYGSRSFYFLDW (180) | 8.8.16 |
| HD331 | 315B | IgG/A | V3-11*06 F | 90.3 | J4*02 F | 89.6 | D2-15*01 F | CAREDCHGTSCYSGDW (181) | 8.8.14 |
| HD334 | 251A | IgG/A | V3-30*03 F | 97.2 | J4*02 F | 91.7 | D6-19*01 F | CAKVRLTSYSIGWFSFDYW (182) | 8.8.17 |
| HD334 | 256A | IgG/A | V3-30*03 F | 96.2 | J3*02 F | 82.0 | D5-18*01 F | CAKDFLRVYSYGWHSFDIW (183) | 8.8.17 |
| HD337 | 278 | IgG/A | V3-30*03 F | 100 | J4*02 F | 93.8 | D6-13*01 F | CAKVTIIAAADLLDYW (184) | 8.8.14 |
| HD335 | 123 | IgG/A | V3-30*04 F | 94.1 | J6*02 F | 82.6 | D2-15*01 F | CARVTGDCTGNRCSYWAYYYYGLD VW(185) | 8.8.24 |
| HD331 | 310A | IgG/K | V3-66*01 F | 94.4 | J4*02 F | 93.8 | D3-22*01 F | CTRDPSQYYDSRGHYYQTFTPSFDSW (186) | 8.7.24 |
| HD331 | 320 | IgA/K | V1-69*01 F | 95.5 | J6*02 F | 77.4 | D3-10*01 F | CARDRVPSYSPSRRFSTKGAMWGKYGM DVW (187) | 8.8.28 |

| | | | Light Chain | | | | | |
|---|---|---|---|---|---|---|---|---|
| Donor | NORO mAb clone | isotype/ Light chain | V gene | V gene % length | J gene | J Gene % identity | Junction ID (SEQ ID NO:) | LCDR length |
| HD329 | 115 | IgG/K | V4-1*01 F | 95.8 | J4*01 F | 97.2 | CQQYYNSPLAF (188) | 12.3.9 |
| HD331 | 313.1 | IgG/K | V2-28*01 F | 97.6 | J2*02 F | 97.2 | CMQALQTRTF (189) | 11.3.8 |
| HD334 | 250B | IgG/A | V1-40*01 F | 95.8 | J2*01 F | 89.5 | CQSYDRSVSGSAVF (190) | 9.3.12 |
| HD337 | 279A | IgG/A | V1-47*01 F | 92.6 | J3*02 F | 94.6 | CATLDINMTWVF (191) | 8.3.10 |

Supplementary Table 1.
Antibody variable gene usage for GII.4 Sydney 2012 VLP-binding mAbs; Heavy Chain.

| HD331 | 329A | IgG/A | V1-44*01 F | 96.5 | J3*02 F | 100 | CAAWDDSLNGWVF (192) | 8.3.11 |
| --- | --- | --- | --- | --- | --- | --- | --- | --- |
| 990 | 202A.1 | IgG/A | V1-47*01 F | 97.4 | J2*01 F | 100 | CSAWDDSLSGPVF (193) | 1.3.11 |
| HD331 | 312A | IgG/A | V1-40*01 F | 96.2 | J2*01 F | 97.1 | CQSYDNRLRVF (194) | 9.3.9 |
| HD331 | 317 | IgG/A | V3-25*03 F | 93.6 | J3*02 F | 89.5 | CQSVDTRGTYKVF (195) | 6.3.11 |
| HD333 | 303 | IgG/K | V2-8*01 F | 98.3 | J2*01 F | 100 | CSSYAGTYNCVVF (196) | 9.3.11 |
| HD333 | 296A | IgG/A | V1-40*01 F | 96.9 | J2*01 F | 92.1 | CQSYDSRLSSNVVF (197) | 9.3.12 |
| HD331 | 315B | IgG/A | V1-40*01 F | 97.2 | J3*02 F | 92.1 | CQSYDRSLSKSRVF (198) | 9.3.12 |
| HD334 | 251A | IgG/A | V1-51*01 F | 97.9 | J3*02 F | 91.9 | CGTWDTSLRACLF (199) | 8.3.11 |
| HD334 | 256A | IgG/A | V1-51*01 F | 95.8 | J3*02 F | 91.1 | CGTWDLSLTAGWVF (200) | 8.3.11 |
| HD337 | 278 | IgG/A | V1-40*01 F | 100 | J2*01 F | 97.4 | CQSYDSSLSGPVVF (201) | 9.3.12 |
| HD335 | 123 | IgG/A | V2-8*01 F | 97.6 | J1*01 F | 94.7 | CGSYAGSTTSGYVF (202) | 9.3.12 |
| HD331 | 310A | IgG/K | V1-17*03 F | 97.5 | J4*01 F | 100 | CLQHDTYPLTF (203) | 6.3.9 |
| HD331 | 320 | IgA/K | V2-28*01 F | 99.3 | J1*01 F | 100 | CMQALQTPRTF (204) | 11.3.9 |

Heavy and light chain variable gene regions were sequenced.
All of the mAbs had unique heavy and light complementarity-determining region 3 (CDR3) sequences.

SUPPLEMENTARY TABLE 1

Antibody variable gene usage for GII.4 Sydney 2012 VLP-binding mAbs.

Heavy Chain

| Donor | NORO mAb clone | Isotype/ Light chain | V gene | V gene % Identity | J gene | J gene % Identity | D gene | Junction (SEQ ID NO:) | HCDR length |
| --- | --- | --- | --- | --- | --- | --- | --- | --- | --- |
| HD329 | 115 | IgG/K | V3-11*01 F | 89.2 | J6*02 F | 94.1 | D8-13*01 F | CARDRLPASGSHWFPHW (171) | 8.8.15 |
| HD331 | 313.1 | IgG/K | V3-11*08 F | 92.7 | J6*02 F | 80.7 | D1-1*01 F | CARMGRLELERRPHYYYPLDVW (172) | 8.8.20 |
| HD334 | 250B | IgG/λ | V3-11*08 F | 85.6 | J4*02 F | 97.0 | D1-26*01 F | CARATSQGATSYYFDSW (173) | 8.8.15 |
| HD337 | 279A | IgG/λ | V3-30*03 F | 91.7 | J6*02 F | 79.0 | D2-8*01 F | CAKVEIHYYSNSLLGMDVW (174) | 8.8.17 |
| HD331 | 329A | IgG/λ | V3-11*08 F | 86.2 | J4*02 F | 91.7 | D3-10*01 F | CARYNYYGSGSFVFDYW (175) | 8.8.15 |
| 980 | 202A.1 | IgG/λ | V1-2*02 F | 93.3 | J3*01 F | 92.0 | D7-27*01 F | CARDLLRNWGDHDAFDVW (176) | 8.7.16 |
| HD331 | 312A | IgG/λ | V3-11*08 F | 94.1 | J4*02 F | 89.6 | D2-15*01 F | CARDAQYCSGGRCYLVFDYW (177) | 8.8.18 |
| HD331 | 317 | IgG/λ | V4-34*01 F | 91.2 | J5*02 F | 90.0 | D3-16*02 F | CARDQMRTRGALFRRFDPW (178) | 8.7.17 |
| HD333 | 303 | IgG/K | V3-30*01 F | 97.8 | J6*02 F | 80.7 | D3-10*01 F | CARDCRVGWVFTYGMDVW (179) | 8.8.16 |
| HD333 | 296A | IgG/λ | V3-11*05 F | 85.1 | J1*01 F | 86.3 | D3-10*01 F | CARYGAEYGSRSFYFLDW (180) | 8.8.16 |
| HD331 | 315B | IgG/λ | V3-11*06 F | 90.3 | J4*02 F | 89.8 | D2-15*01 F | CAREDCHQTSGYSGDW (181) | 8.8.14 |
| HD334 | 251A | IgG/λ | V3-30*03 F | 87.2 | J4*02 F | 91.7 | D8-19*01 F | CAKYRLTSYSIGWFSFDYW (182) | 8.8.17 |
| HD334 | 258A | IgG/λ | V3-30*03 F | 96.2 | J3*02 F | 82.0 | D5-18*01 F | CAKDFLRYYSYGWHSFDIW (183) | 8.8.17 |
| HD337 | 278 | IgG/λ | V3-30*03 F | 100 | J4*02 F | 93.8 | D8-13*01 F | CAKVTIIAAADLLDYW (184) | 8.8.14 |
| HD336 | 123 | IgG/λ | V3-30*04 F | 94.1 | J6*02 F | 82.6 | D2-15*01 F | CARVTGDCTGNRCSYWAYYYYGLDVW (185) | 8.8.24 |
| HD331 | 310A | IgG/K | V3-66*01 F | 94.4 | J4*02 F | 93.8 | D3-22*01 F | CTRDPSQYYDSRGHYYQTFTPSFDSW (186) | 8.7.24 |
| HD331 | 320 | IgG/K | V1-69-01 F | 85.6 | J6*02 F | 77.4 | D3-10*01 F | CARDRVPSYSFSRRFSTKGAMWGKYGMDVW (187) | 8.8.28 |

Light Chain

| Donor | V gene | V gene length | J Gene | J Gene % Identity | Junction (SEQ ID NO:) | LCDR length |
| --- | --- | --- | --- | --- | --- | --- |
| HD329 | V4-1*01 F | 95.8 | J4*01 F | 97.2 | CQQYYNSPLAF (188) | 12.3.9 |
| HD331 | V2-28*01 F | 97.8 | J2*02 F | 97.2 | CMQALQTRTF (189) | 11.3.8 |
| HD334 | V1-40*01 F | 85.8 | J2*02 F | 89.5 | CQSYDRSVSGSAVF (190) | 8.3.12 |
| HD337 | V1-47*01 F | 92.6 | J3*02 F | 84.8 | CATLDINMTWVF (191) | 8.3.10 |
| HD331 | V1-44*01 F | 86.5 | J3*02 F | 100 | CAAWDDSLNGWVF (192) | 8.3.11 |
| 980 | V1-47*01 F | 97.4 | J2*01 F | 100 | CSAWDDSLSGPVF (193) | 1.3.11 |
| HD331 | V1-40*01 F | 96.2 | J2*01 F | 97.1 | CQSYDNRLRVF (194) | 9.3.9 |
| HD331 | V3-25*03 F | 93.6 | J3*02 F | 89.5 | CQSVDTRGTYKVF (195) | 6.3.11 |
| HD333 | V2-8*01 F | 98.3 | J2*01 F | 100 | CSSYAGTYNCVVF (196) | 9.3.11 |
| HD333 | V1-40*01 F | 86.9 | J2*01 F | 92.1 | CQSYDSRLSSNVVF (197) | 8.3.12 |
| HD331 | V1-40*01 F | 97.2 | J3*02 F | 82.1 | CQSYDRSLSKSRVF (198) | 9.3.12 |
| HD334 | V1-61*01 F | 87.9 | J3*02 F | 91.9 | CQTWDTSLRACLF (199) | 8.3.11 |
| HD334 | V1-51*01 F | 96.8 | J3*02 F | 91.1 | CGTWDLSLTAGWVF (200) | 8.3.12 |
| HD337 | V1-40*01 F | 100 | J2*01 F | 97.4 | CQSYDSSLSGPVVF (201) | 8.3.12 |
| HD336 | V2-8*01 F | 97.6 | J1*01 F | 94.7 | CGSYAGSTTSGYVF (202) | 9.3.12 |
| HD331 | V1-17*03 F | 97.5 | J4*61 | 100 | CLQHDTYPLTF (203) | 6.3.9 |
| HD331 | V2-28*01 F | 89.3 | J1*01 F | 100 | CMQALQTPRTF (204) | 11.3.8 |

SUPPLEMENTARY TABLE 1-continued

Antibody variable gene usage for GII.4 Sydney 2012 VLP-binding mAbs.

Heavy and light chain variable gene regions were sequenced.
All of the mAbs had unique heavy and light complementarity-determining region 3 (CDR3) sequences.
Antibody sequence analysis for 13 cross-reactive human mAbs.

| NORO mAb clone | Isotype | V gene | V gene % Identity | J gene | J gene % Identity | D gene | JUNCTION | HCDR length |
|---|---|---|---|---|---|---|---|---|
| 155.5 | IgM | V4-34*01 F | 100 | J6*02 F | 96.8 | D3-10*01 F | CARGLNTMVRGVLNYYYYYGMDVW | 8.7.22 |
| 158.3 | IgM | V4-34*01 F | 100 | J6*02 F | 89.1 | D3-16*01 F | CARGLMDVW | 8.7.7 |
| 161.2 | IgM | V3-74*01 F | 100 | J3*02 F | 92.0 | D1-1*01 F | CRATGTSPRASKDAFDIW | 8.8.16 |
| 168.2 | IgM | V3-30*01 F | 100 | J6*02 F | 90.3 | D3-10*01 F | CARSVIGYYYYGMDVW | 8.8.14 |
| 170.5 | IgM | V1-18*01 F | 100 | J1*01 F | 90.4 | D4-23*01 ORF | CARDQYGGNMYFQHW | 8.8.13 |
| 167.3 | IgG | V5-51*01 F | 100 | J4*02 F | 87.5 | D2-15*01 F | CARSGRGHRGGSPDYW | 8.8.14 |
| 178.6 | IgG | V3-30*03 F | 100 | J4*02 F | 85.2 | D6-19*01 F | CAKDWYLAMAGAAFDSW | 8.8.16 |
| 202A.2 | IgG | V1-2*02 F | 93.3 | J3*01 F | 92.0 | D7-27*01 F | CARDLLRNWGDHDAFDVW | 8.7.16 |
| 279A | IgSG | V3-30*03 F | 91.7 | J6*02 F | 79.0 | D2-8*01 F | CAKVEIHYYSNSLLGMDVW | 8.8.17 |
| 310A | IgG | V3-66*01 F | 94.4 | J4*02 F | 93.8 | D3-22*01 F | CTRDPSQYYDSRGHYYQTFTPSFDSW | 8.7.24 |
| 323A | IgG | V3-30*03 F | 95.8 | J4*02 F | 93.8 | D1-14*01 ORF | CAKPVLSPFDYW | 8.8.10 |
| 232A.2 | IgA | V4-34*02 F | 83.6 | J6*02 F | 79.0 | D3-10*01 F | CARGRPHDYSPGSYSRPRRYYGLDVW | 8.7.24 |
| 320 | IgA | V1-69*01 F | 95.6 | J6*02 F | 77.4 | D3-10*01 F | CARDRVPSYSPSRRFSTKGAMWGKYGMDVW | 8.8.28 |

| NORO mAb clone | V gene | V gene % identity | J gene | J gene % identity | AA JUNCTION | LCDR length |
|---|---|---|---|---|---|---|
| 155.5 | V1-6*01 F | 100 | J1*01 F | 97.3 | CLQDYNYPRTF | 6.3.9 |
| 158.3 | V1-8*01 F | 100 | J2*02 F | 100 | CQQYYSYPRTF | 6.3.9 |
| 161.2 | V3-27*01 F | 100 | J2*01 F | 100 | CYSAADNIVVF | 6.3.9 |
| 168.2 | V9-49*01 F | 100 | J2*01 F | 89.5 | CGADHGSGILF | 7.8.9 |
| 170.5 | V1-8*01 F | 100 | J5*01 F | 100 | CQOYYSYPITF | 6.3.9 |
| 167.3 | V3-11*01 F | 100 | J3*01 F | 97.4 | CQQRSNWPFTF | 6.3.9 |
| 178.6 | V3-19*01 F | 96.1 | J2*01 F | 81.6 | CNSRDSSGKPSF | 6.3.10 |
| 202A.2 | V1-47*01 F | 97.5 | J2*01 F | 100 | CSAWDDSLSGPV | 1.3.11 |
| 279A | V1-47*01 F | 92.6 | J3*02 F | 94.6 | CATLDINMTWVF | 8.3.10 |
| 310A | V1-17*03 F | 98.0 | J4*01 F | 100 | CLQHDTYPLTF | 6.3.9 |
| 323A | V2-14*01 F | 97.2 | J2*01 F | 94.6 | CCSYTSSSTEVF | 9.3.10 |
| 232A.2 | V3-20*01 F | 91.8 | J2*01 F | 89.5 | CQQYSSSPYTF | 7.3.9 |
| 320 | V2-28*01 F | 99.3 | J1*01 F | 100 | CMQALQTPRTF | 11.3.9 |

Heavy and variable gene regions were sequenced.
All of the mAbs had unique heavy and light complementarity-determining region 3 (CDR3) sequences.

TABLE B

Data processing and refinement statistics for GII.4 P domain-Fab 320 complex.

| Data Collection | |
|---|---|
| Beamline | ALS Beamline 5.0.1 |
| Wavelength, Å | 0.97741 |
| Space group | P21 21 2 |
| Cell dimensions, Å | 119.25, 186.27, 73.44 |
| α,β,γ,° | 90, 90, 90 |
| Resolution, Å | 50-2.25 (2.29-2.25)[a] |
| Total Reflections | 1716311 |
| Unique Reflections | 78053 (3854)[a] |
| Redundancy | 6.5 (6.2)[a] |
| Completeness (%) | 99.82 |
| <I/sigma> | 15.6875 (2.375)[a] |
| $R_{meas}$[b] | 0.129 (0.846)[a] |
| $R_{pim}$[b] | 0.050 (0.340)[a] |
| Refinement Statistics | |
| Resolution, Å | 50-2.25 (2.29-2.25)[a] |
| Reflections (work) | 73965 |
| Reflections (Test) | 3926 |
| $R_{work}$[c]/$R_{free}$[d] (%) | 18.08/22.55 |
| No. of Atoms | |
| Protein | |
| P-domain Dimer | 4798 |
| Noro-320 Fab | 6674 |
| Water | 1059 |

TABLE B-continued

Data processing and refinement statistics for GII.4 P domain-Fab 320 complex.

| Average B Value (Å$^2$) | |
| --- | --- |
| P-domain Dimer | 34.2505 |
| Noro-320 Fab | 31.67 |
| Water | 36.085 |
| RMSD from Ideal Geometry | |
| Bond length (Å) | 0.003 |
| Bond angle (°) | 0.614 |
| Ramachandran Statistics [e] | |
| Favored | 98.38% |
| Outliers | 0.20% |

[a] Numbers in parentheses refer to the highest resolution shell
[b] $R_{meas} = \Sigma_{hkl} \{N(hkl)/[N(hkl) - 1]\}^{1/2} \times \Sigma_i |I_i(hkl) - \{I(hkl)\}| / \Sigma_{hkl} \Sigma_i I_i(hkl)$ and $R_{pim} = \Sigma_{hkl} (1/(n-1))^{1/2} \Sigma_i |I_{hkl,i} - I| / \Sigma_{hkl} \Sigma_i I_{hkl,i}$, where $I_{hkl}$ i is the scaled intensity of the $i^{th}$ measurement of reflection h, k, l, is the average intensity for that reflection, and n is the redundancy.
[c] Rwork = $\Sigma_{hkl} |Fo - Fc| / \Sigma_{hkl} |Fo| \times 100$, where Fo and Fc are the observed and calculated structure factors, respectively.
[d] Rfree was calculated as for $R_{work}$, but on a test set comprising 5% of the data excluded from refinement.
[e] Calculated with MolProbity (Chen et al., 2010).

DESCRIPTION OF ILLUSTRATIVE EMBODIMENTS

As discussed above, development of norovirus vaccines has proven challenging. In this study, the inventors describe the isolation and characterization of a panel of human monoclonal antibodies (mAbs) that bind to GII.4 Sydney 2012 VLPs. The majority of these antibodies also block receptor binding, as inferred by their ability to inhibit hemagglutination of human O+ red blood cells (RBCs) or the interaction between GII.4 Sydney 2012 VLPs and porcine gastric mucin (PGM). Both of these assays are surrogate systems for testing HuNoV neutralization (Czako et al., 2012; Reeck et al., 2010). For over 40 years there have been numerous documented attempts to cultivate HuNoVs in vitro, but previously none of them resulted in the establishment of a robust reproducible system of viral growth (Jones et al., 2014; Duizer et al., 2004; Herbst-Kralovetz et al., 2013). Recent breakthroughs in the development of an in vitro replication system using human intestinal organoid technology have now made it possible to cultivate HuNoV and to test inhibition of growth, or neutralization, using antibodies (Ettayebi et al., 2016; Constantini et al., 2018).

Here, the inventors used a human jejunal monolayer culture system to identify antibodies that neutralize live GII.4 Sydney 2012 HuNoV. They identified the first neutralizing human mAbs against norovirus, as well as a panel of human anti-GII.4 Sydney 2012 VLP binding IgGs and the first anti-GII.4 human IgA molecules. Almost 70% of the mAbs that the inventors isolated exhibited a high level of potency, inhibiting GII.4 Sydney 2012 VLPs from binding to PGM at half-maximal effective concentrations ($EC_{50}$) below 24 μg/mL. They also used this panel of mAbs to identify major antigenic sites on the GII.4 Sydney 2012 major capsid protein.

The broadly cross-reactive naturally-occurring human monoclonal included IgMs, IgAs and IgGs reactive with NoV genogroup I or II (GI or GII). Among the panel the inventors noticed three different binding patterns and identified monoclonal antibodies (mAbs) that neutralized at least one GI or GII NoV strain when using a receptor blocking assay. X-ray crystallography studies of a GII-specific neutralizing mAb revealed the antibody neutralizes not by directly inhibiting receptor binding, but instead through steric hindrance. These data will be useful when designing and evaluating new vaccine candidates. Some of the human mAbs described here also could be used as biologics for the prevention or treatment of chronic NoV infections or severe NoV disease during outbreaks.

These studies contribute new insights into natural human humoral immunity to HuNoVs and provide mAbs that have the potential to be used for diagnostic and therapeutic purposes. These and other aspects of the disclosure are described in detail below.

I. Norovirus Virus

Norovirus is the most common cause of gastroenteritis. Infection is characterized by diarrhea, vomiting, and stomach pain. Blood is not usually present. Fever or headaches may also occur. This usually develops 12 to 48 hours after being exposed. Recovery typically occurs within 1 to 3 days. Complications may include dehydration.

The virus is usually spread by the fecal-oral route. This may be by contaminated food or water or person-to-person contact. It may also spread via contaminated surfaces or through the air. Risk factors include unsanitary food preparation. Diagnosis is generally based on symptoms. Confirmatory testing may be done for public health purposes.

Prevention involves proper hand washing and disinfection of contaminated surfaces. Alcohol-based hand sanitizers are less effective. A vaccine does not exist. There is no specific treatment. Efforts involve supportive care such as drinking sufficient fluids or intravenous fluids. Oral rehydration solutions are the preferred fluids to drink.

Norovirus results in about 685 million cases of disease and 200,000 deaths globally a year. It is common both in the developed and developing world. Those under the age of five are most often affected and in this group it results in about 50,000 deaths in the developing world. Disease more commonly occurs in winter months. It often occurs in outbreaks, especially among those living in close quarters. In the United States it is the cause of about half of food-borne disease outbreaks. The disease is named after Norwalk, Ohio, where an outbreak occurred in 1968.

Indeed, Norovirus causes about 18% of all cases of acute gastroenteritis worldwide. It is relatively common in developed countries and in low-mortality developing countries (20% and 19% respectively) compared to high-mortality developing countries (14%). Proportionately it causes more illness in people in the community or in hospital outpatients (24% and 20% respectively) as compared with hospital inpatients (17%) in whom other causes are more common.

Norovirus is a common cause of epidemics of gastroenteritis on cruise ships. The US Centers for Disease Control and Prevention through its Vessel Sanitation Program record and investigate outbreaks of gastrointestinal illness—mostly caused by norovirus—on cruise ships with both a U.S. and foreign itinerary; there were 12 in 2015, and 10 from 1 Jan. to 9 May 2016. An outbreak may affect over 25% of passengers, and a smaller proportion of crew members.

Norovirus infection is characterized by nausea, vomiting, watery diarrhea, abdominal pain, and in some cases, loss of taste. A person usually develops symptoms of gastroenteritis 12 to 48 hours after being exposed to norovirus. General lethargy, weakness, muscle aches, headaches, and low-grade fevers may occur. The disease is usually self-limiting, and severe illness is rare. Although having norovirus can be unpleasant, it is not usually dangerous and most who contract it make a full recovery within two to three days.

A. Transmission

Noroviruses are transmitted directly from person to person (62-84% of all reported outbreaks) and indirectly via contaminated water and food. They are extremely contagious, and fewer than twenty virus particles can cause an infection (some research suggests as few as five). Transmission can be aerosolized when those stricken with the illness vomit, and can be aerosolized by a toilet flush when vomit or diarrhea is present; infection can follow eating food or breathing air near an episode of vomiting, even if cleaned up. The viruses continue to be shed after symptoms have subsided and shedding can still be detected many weeks after infection.

Vomiting, in particular, transmits infection effectively, and appears to allow airborne transmission. In one incident, a person who vomited spread infection across a restaurant, suggesting that many unexplained cases of food poisoning may have their source in vomit. In December 1998, 126 people were dining at six tables; one woman vomited onto the floor. Staff quickly cleaned up, and people continued eating. Three days later others started falling ill; 52 people reported a range of symptoms, from fever and nausea to vomiting and diarrhea. The cause was not immediately identified. Researchers plotted the seating arrangement: more than 90% of the people at the same table as the sick woman later reported becoming ill. There was a direct correlation between the risk of infection of people at other tables and how close they were to the sick woman. More than 70% of the diners at an adjacent table fell ill; at a table on the other side of the restaurant, the attack rate was still 25%. The outbreak was attributed to a Norwalk-like virus (norovirus). Other cases of transmission by vomit were later identified.

In one outbreak at an international scout jamboree in the Netherlands, each person with gastroenteritis infected an average of 14 people before increased hygiene measures were put in place. Even after these new measures were enacted, an ill person still infected an average of 2.1 other people. A US CDC study of 11 outbreaks in New York State lists the suspected mode of transmission as person-to-person in seven outbreaks, foodborne in two, waterborne in one, and one unknown. The source of waterborne outbreaks may include water from municipal supplies, wells, recreational lakes, swimming pools and ice machines.

Shellfish and salad ingredients are the foods most often implicated in norovirus outbreaks. Ingestion of shellfish that have not been sufficiently heated—under 75° C. (167° F.)—poses a high risk for norovirus infection. Foods other than shellfish may be contaminated by infected food handlers. Many norovirus outbreaks have been traced to food that was handled by one infected person.

B. Classification

Noroviruses (NoV) are a genetically diverse group of single-stranded positive-sense RNA, non-enveloped viruses belonging to the family Caliciviridae. According to the International Committee on Taxonomy of Viruses, the genus Norovirus has one species, which is called Norwalk virus. Serotypes, strains and isolates include Norwalk virus, Hawaii virus, Snow Mountain virus, Mexico virus, Desert Shield virus, Southampton virus, Lordsdale virus and Wilkinson virus.

Noroviruses commonly isolated in cases of acute gastroenteritis belong to two genogroups: genogroup I (GI) includes Norwalk virus, Desert Shield virus and Southampton virus; and II (GII), which includes Bristol virus, Lordsdale virus, Toronto virus, Mexico virus, Hawaii virus and Snow Mountain virus.

Noroviruses can genetically be classified into seven different genogroups (GI, GII, GIII, GIV, GV, GVI, and GVII), which can be further divided into different genetic clusters or genotypes. For example, genogroup II, the most prevalent human genogroup, presently contains 19 genotypes. Genogroups I, II and IV infect humans, whereas genogroup III infects bovine species, and genogroup V has recently been isolated in mice.

Most noroviruses that infect humans belong to genogroups GI and GII. Noroviruses from Genogroup II, genotype 4 (abbreviated as GII.4) account for the majority of adult outbreaks of gastroenteritis and often sweep across the globe. Recent examples include US95/96-US strain, associated with global outbreaks in the mid- to late-1990s; Farmington Hills virus associated with outbreaks in Europe and the United States in 2002 and in 2004; and Hunter virus which was associated with outbreaks in Europe, Japan and Australasia. In 2006, there was another large increase in NoV infection around the globe. GII.17 emerged and became predominant in many areas in Asia and was detected in other countries in 2014-2016. Since then a GII.2 strains has emerged in a number of countries. Reports have shown a link between the expression of human histo-blood group antigens (HBGAs) and the susceptibility to norovirus infection. Studies have suggested the viral capsid of noroviruses may have evolved from selective pressure of human HBGAs.

One study suggests the protein MDA-5 may be the primary immune sensor that detects the presence of noroviruses in the body. Some people have common variations of the MDA-5 gene that could make them more susceptible to norovirus infection. Another study suggested a specific genetic version of norovirus (which would not be distinguishable from other types of the virus using standard viral antibody tests) interacts with a specific mutation in the ATG16L1 gene to help trigger symptomatic Crohn's disease in mice that have been subjected to a chemical that causes intestinal injury similar to the process in humans. (There are other similar ways for such diseases to happen like this, and this study in itself does not prove norovirus causes Crohn's disease in humans).

C. Structure

Viruses in Norovirus are non-enveloped, with icosahedral geometries. Capsid diameters vary widely, from 23-40 nm in diameter. The larger capsids (38-40 nm) exhibit T=3 symmetry and are composed of 180 VP1 proteins. Small capsids (23 nm) show T=1 symmetry and are composed of 60 VP1 proteins. The virus particles demonstrate an amorphous surface structure when visualized using electron microscopy.

Noroviruses contain a linear, non-segmented, positive-sense RNA genome of approximately 7.5 kbp, encoding a large polyprotein which is cleaved into six smaller nonstructural proteins (NS1/2 to NS7) by the viral 3C-like protease (NS6), a major structural protein (VP1) of about 58~60 kDa and a minor capsid protein (VP2).

The most variable region of the viral capsid is the P2 domain, which contains antigen-presenting sites and carbohydrate-receptor binding regions. The estimated mutation rate ($1.21 \times 10^{-2}$ to $1.41 \times 10^{-2}$ substitutions per site per year) in this virus is high even compared with other RNA viruses. In addition, a recombination hotspot exists at the ORF1-ORF2 (VP1) junction.

D. Lifecycle and Persistence

Viral replication is cytoplasmic. Entry into the host cell is achieved by attachment to host receptors, which mediates endocytosis. Replication follows the positive stranded RNA virus replication model. Positive stranded RNA virus transcription is the method of replication. Translation takes place by leaky scanning and RNA termination-reinitiation. Humans and other mammals serve as the natural host. Transmission routes are fecal-oral and contamination.

The norovirus can survive for long periods outside a human host depending on the surface and temperature conditions: it can stay for weeks on hard surfaces, and up to twelve days on contaminated fabrics, and it can survive for months, maybe even years in contaminated still water. A 2006 study found the virus remained on surfaces used for food preparation seven days after contamination.

E. Pathophysiology

When a person becomes infected with norovirus, the virus is replicated within the small intestine. After approximately one to two days, norovirus infection symptoms can appear. The principal symptom is acute gastroenteritis that develops between 12 and 48 hours after exposure, and lasts for 24-72 hours. The disease is usually self-limiting, and characterized by nausea, forceful vomiting, watery diarrhea, and abdominal pain, and in some cases, loss of taste. General lethargy, weakness, muscle aches, headache, coughs, and low-grade fever may occur.

Severe illness is rare; although people are frequently treated at the emergency ward, they are rarely admitted to the hospital. The number of deaths from norovirus in the United States is estimated to be around 300 each year, with most of these occurring in the very young, the elderly, and persons with weakened immune systems. Symptoms may become life-threatening in these groups if dehydration or electrolyte imbalance is ignored or not treated.

F. Diagnosis and Detection

Specific diagnosis of norovirus is routinely made by polymerase chain reaction (PCR) assays or quantitative PCR assays, which give results within a few hours. These assays are very sensitive and can detect as few as 10 virus particles. Tests such as ELISA that use antibodies against a mixture of norovirus strains are available commercially, but lack specificity and sensitivity. Due to a lack of specific therapy, the need for expensive stool diagnostics is being questioned by experts if gastroenteritis by noroviruses has already been detected in the environment.

Routine protocols to detect norovirus in clams and oysters by reverse transcription polymerase chain reaction are being employed by governmental laboratories such as the Food and Drug Administration (FDA) in the USA.

G. Prevention

After infection, immunity to the same strain of the virus—the genotype—protects against reinfection for between 6 months to 2 years. This immunity does not fully protect against infection with the other diverse genotypes of the virus.

Hand washing with soap and water is an effective method for reducing the transmission of norovirus pathogens. Alcohol rubs (≥62% ethanol) may be used as an adjunct, but are less effective than hand-washing, as norovirus lacks a lipid viral envelope. Surfaces where norovirus particles may be present can be sanitized with a solution of 1.5% to 7.5% of household bleach in water, or other disinfectants effective against norovirus.

In health-care environments, the prevention of nosocomial infections involves routine and terminal cleaning. Non-flammable alcohol vapor in $CO_2$ systems is used in health care environments where medical electronics would be adversely affected by aerosolized chlorine or other caustic compounds.

In 2011, the Centers for Disease Control and Prevention (CDC) published a clinical practice guideline addressing strategies for the prevention and control of norovirus gastroenteritis outbreaks in health-care settings. Based on a systematic review of published scientific studies, the guideline presents 51 specific evidence-based recommendations, which were organized into 12 categories: 1) patient cohorting and isolation precautions, 2) hand hygiene, 3) patient transfer and ward closure, 4) food handlers in healthcare, 5) diagnostics, 6) personal protective equipment, 7) environmental cleaning, 8) staff leave and policy, 9) visitors, 10) education, 11) active case-finding, and 12) communication and notification. The guideline also identifies eight high-priority recommendations, and suggests several areas in need of future research.

Ligocyte announced in 2007 that it was working on a vaccine and had started phase 1 trials. The company has since been acquired by Takeda Vaccines. As of 2011, a monovalent nasal vaccine had completed phase I/II trials, while bivalent intramuscular and nasal vaccines were at earlier stages of development. The two vaccines rely on using a virus-like particle that is made of the norovirus capsid proteins in order to mimic the external structure of the virus. Since there is no RNA in this particle, it is incapable of reproducing and cannot cause an infection.

H. Treatment

There is no specific medicine to treat people with norovirus illness. Norovirus infection cannot be treated with antibiotics because it is not a bacterial infection. Treatments aim to avoid complications by measures such as the management of dehydration caused by fluid loss in vomiting and diarrhea, and to mitigate symptoms using antiemetics and antidiarrheals.

II. Monoclonal Antibodies and Production Thereof

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies binding to norovirus will have several applications. These include the production of diagnostic kits for use in detecting and diagnosing norovirus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce norovirus-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g. a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke (2004) Methods Mol. Biol. 248: 443-463), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling, the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A. When the antibody neutralizes norovirus, antibody escape mutant variant organisms can be isolated by propagating norovirus in vitro or in animal models in the presence of high concentrations of the antibody. Sequence analysis of the norovirus gene encoding the antigen targeted by the antibody reveals the mutation(s) conferring antibody escape, indicating residues in the epitope or that affect the structure of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen. Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to by hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-norovirus antibody, the above-described binding methodology is performed in two orientations: In a first orientation, the reference antibody is allowed to bind to the norovirus antigen under saturating conditions followed by assessment of binding of the test antibody to the norovirus antigen. In a second orientation, the test antibody is allowed to bind to the norovirus antigen molecule under saturating conditions followed by assessment of binding of the reference antibody to the norovirus molecule. If, in both orientations, only the first (saturating) antibody is capable of binding to the norovirus, then it is concluded that the test antibody and the reference antibody compete for binding to the norovirus. As will be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, MA, surface plasmon resonance, flow cytometry or any other quantitative or qualitative antibody binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity,*" J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma RIII*" Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha* (1-6) *Dextran Increases Its Affinity For Antigen,*" J. Exp. Med. 168(3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region,*" J. Immunol. 143(8): 2595-2601; Routledge, E. G. et al. (1995) "*The Effect Of Aglycosylation On The Immunogenicity Of A Humanized Therapeutic CD3 Monoclonal Antibody,*" Transplantation 60(8):847-53; Elliott, S. et al. (2003) "*Enhancement Of Therapeutic Protein In Vivo Activities Through Glycoengineering,*" Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity,*" J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as *E. coli*, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. F(ab') antibody derivatives are monovalent, while F(ab')$_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAb, but were completely devoid of enhancing activity. LALA mutations of this nature are therefore contemplated in the context of the presently disclosed antibodies.

Altered Glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1 \times 10^{-8}$ M or less and from Fc gamma RIII with a Kd of $1 \times 10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline.

Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:
1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.*, 22 (10), 1302-1306, 2004; Chennamsetty et al., *PNAS*, 106 (29), 11937-11942, 2009; Voynov et al., *Biocon. Chem.*, 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 μg/mL.

Solubility. One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol*, 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection; however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab').sub.2 bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from *E. coli*, which can be chemically coupled to form bispecific antibodies. Shalaby et al., J. Exp. Med., 175: 217-225 (1992) describe the production of a humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., Nat. Biotechnol., 16, 677-681 (1998). doi:10.1038/nbt0798-677pmid.9661204). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., *FEBS Letters.* 2005; 579: 3264; Wong and Scott, *Nat. Rev. Mol. Cell Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tuft et al., J. Immunol. 147: 60, 1991; Xu et al., Science, 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1).sub.n-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises
- (a) a first Fab molecule which specifically binds to a first antigen
- (b) a second Fab molecule which specifically binds to a second antigen, and wherein the variable domains VL and VH of the Fab light chain and the Fab heavy chain are replaced by each other, wherein the first antigen is an activating T cell antigen and the second antigen is a target cell antigen, or the first antigen is a target cell antigen and the second antigen is an activating T cell antigen; and wherein
- i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or
- ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are anew class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/anti-viral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/antiviral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTEs

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/antiviral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies may have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. Active/Passive Immunization and Treatment/Prevention of Norovirus Infection A. Formulation and Administration The present disclosure provides pharmaceutical compositions comprising anti-norovirus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of norovirus infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, by nebulizer, or via intrarectal or vaginal delivery. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

C. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNC12, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, the present disclosure concerns immunodetection methods for binding, purifying, removing, quantifying and otherwise generally detecting norovirus and its associated antigens. While such methods can be applied in a traditional sense, another use will be in quality control and monitoring of vaccine and other virus stocks, where antibodies according to the present disclosure can be used to assess the amount or integrity (i.e., long term stability) of antigens in viruses. Alternatively, the methods may be used to screen various antibodies for appropriate/desired reactivity profiles.

Other immunodetection methods include specific assays for determining the presence of norovirus in a subject. A wide variety of assay formats are contemplated, but specifically those that would be used to detect norovirus in a fluid obtained from a subject, such as saliva, blood, plasma, sputum, semen or urine. In particular, semen has been demonstrated as a viable sample for detecting norovirus (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of norovirus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing norovirus, and contacting the sample with a first antibody in accordance with the present disclosure, as the case may be, under conditions effective to allow the formation of immunocomplexes.

These methods include methods for purifying norovirus or related antigens from a sample. The antibody will preferably be linked to a solid support, such as in the form of a column matrix, and the sample suspected of containing the norovirus or antigenic component will be applied to the immobilized antibody. The unwanted components will be washed from the column, leaving the norovirus antigen immunocomplexed to the immobilized antibody, which is then collected by removing the organism or antigen from the column.

The immunobinding methods also include methods for detecting and quantifying the amount of norovirus or related components in a sample and the detection and quantification of any immune complexes formed during the binding process. Here, one would obtain a sample suspected of containing norovirus or its antigens and contact the sample with an antibody that binds norovirus or components thereof, followed by detecting and quantifying the amount of immune complexes formed under the specific conditions. In terms of antigen detection, the biological sample analyzed may be any sample that is suspected of containing norovirus or norovirus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to norovirus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the norovirus or norovirus antigen is added to the wells. After binding and washing to remove non-specifically bound immune complexes, the bound antigen may be detected. Detection may be achieved by the addition of another anti-norovirus antibody that is linked to a detectable label. This type of ELISA is a simple "sandwich ELISA." Detection may also be achieved by the addition of a second anti-norovirus antibody, followed by the addition of a third antibody that has binding affinity for the second antibody, with the third antibody being linked to a detectable label.

In another exemplary ELISA, the samples suspected of containing the norovirus or norovirus antigen are immobilized onto the well surface and then contacted with the anti-norovirus antibodies of the disclosure. After binding and washing to remove non-specifically bound immune complexes, the bound anti-norovirus antibodies are detected. Where the initial anti-norovirus antibodies are linked to a detectable label, the immune complexes may be detected directly. Again, the immune complexes may be detected using a second antibody that has binding affinity for the first anti-norovirus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of norovirus antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled norovirus monoclonal antibodies to determine the amount of norovirus antibodies in a sample. The basic format would include contacting a known amount of norovirus monoclonal antibody (linked to a detectable label) with norovirus antigen or particle. The norovirus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect norovirus or norovirus antigens, the antibodies may be included in the kit. The immunodetection kits will thus comprise, in suitable container means, a first antibody that binds to norovirus or norovirus antigen, and optionally an immunodetection reagent.

In certain embodiments, the norovirus antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the norovirus or norovirus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically correct and intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

Antibodies and fragments thereof as described in the present disclosure may also be used in a kit for monitoring the efficacy of vaccination procedures by detecting the presence of protective norovirus antibodies. Antibodies, antibody fragment, or variants and derivatives thereof, as described in the present disclosure may also be used in a kit for monitoring vaccine manufacture with the desired immunogenicity.

VI. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Virus-like particles. GII.4 Sydney 2012 virus-like particles (VLPs), based on strain AFV08795.1, were produced and purified, as previously described (Sapparapu et al., 2016). Briefly, VP1 and VP2 capsid protein sequences were cloned into the transfer vector pVL1392 (Epoch Life Sciences, Inc.). The vector was co-transfected with a bacmid vector into Sf9 insect cells. Recombinant virus then was used to inoculate Sf9 cells. VLPs were purified from the culture supernatant using a cesium chloride cushion gradient. GII.4 VLP assembly was verified visually using electron microscopy, and antigenicity was tested by western blot.

VLP binding assay. Antibody reactivity to GII.4 VLPs was tested using an indirect enzyme-linked immunosorbent assay (ELISA). Microtiter plates were coated with 1 µg/mL of GII.4 VLPs in PBS at 4° C. overnight. Wells then were blocked with 5% nonfat dry milk in PBS with 0.05% Tween-20 for 1 hour at room temperature. Purified antibodies were diluted serially in PBS and added to VLP-coated plates for 1 hour at room temperature. Microtiter plates were washed 3 times with PBS-0.05% Tween-20 in between each step. Antibodies that bound to VLPs were detected using horseradish peroxidase tagged anti-κ or -λ chain secondary antibodies (Southern Biotech) for 1 hour at room temperature. Plates were developed using the ultra-TMB reagent (Pierce ThermoFisher) and stopped using sulfuric acid. Absorbance was measured at 450 nm using a BioTek Synergy HT Microplate Reader.

VLP-carbohydrate binding antibody blockade assay. Microtiter plates were coated with 10 µg/mL of pig gastric mucin (PGM) Type III (Sigma) in PBS for 4 hours at room temperature, and then were blocked overnight at 4° C. in 5% nonfat dry milk in PBS with 0.05% Tween-20. GII.4 Sydney 2012 VLPs (0.5 µg/mL) were pretreated with each mAb applied in serial 3-fold dilutions with decreasing concentrations. Complexes then were applied to PGM-coated plates for 1 hour at room temperature. Microtiter plates were washed 3 times with PBS-0.05% Tween-20 in between each step. Bound VLPs were detected using guinea pig serum containing anti-GII.4 Sydney 2012 polyclonal antibodies, followed by an alkaline phosphatase-conjugated anti-guinea pig IgG. Optical density was measured at 405 nm using a Synergy HT Microplate Reader (BioTek).

Hemagglutination inhibition assay. Human type O+ red blood cells were purchased from Rockland Immunochemicals, Inc. Cells were pelleted at 500×g for 10 minutes at 4° C. and washed twice with PBS without $Ca^{2+}$ or $Mg^{2+}$. GII.4 Sydney 2012 VLPs (3.5 µg/mL) were pretreated with decreasing concentrations of each mAb, from 15 to 0.007 µg/mL, in PBS pH 5.5 and incubated at room temperature for 30 minutes. VLP-mAb complexes were added to an equal volume of 0.5% washed red blood cells in PBS pH 6.2 and incubated for 2 hours at 4° C. in a 96-well V-bottom microtiter plate. The HAI titer was determined as the lowest concentration of antibody that completely inhibited hemagglutination.

Human subjects. The inventors studied otherwise healthy adult subjects with a history of acute gastroenteritis contracted during a HuNoV outbreak in North Carolina between Feb. 27 and Mar. 1, 2013. The cause of the outbreak was determined by the Orange County, NC health department to be a GII.4 Sydney 2012 norovirus strain. Subjects were recruited after recovery to donate a one-time peripheral blood sample. The research study was approved by the Vanderbilt University Medical Center Institutional Review Board; all subjects provided written informed consent prior to participation.

Peripheral blood mononuclear cell (PBMC) isolation and hybridoma generation. The inventors obtained PBMCs from heparinized blood by density gradient centrifugation using Ficoll-Histopaque from 7 donors who had recovered recently from natural infection with HuNoV. B cells were transformed with Epstein Barr virus substrain B95.8 in the presence of 2.5 µg/mL of CpG10103, 10 µg/mL of cyclosporine A, and 10 µM Chk2 inhibitor. Approximately $10^7$ PBMCs were plated into a 384-well plate in transformation medium, and a week later were expanded into four 96-well plates containing irradiated human PBMCs as a feeder layer. After an additional 7 days of culture, the supernatants were screened by indirect ELISA for the presence of antibodies that bound to GII.4 Sydney 2012 VLPs. Antibodies that bound to GII.4 Sydney 2012 VLPs were detected using horseradish peroxidase tagged anti-human IgA or IgG secondary antibodies (Southern Biotech). Wells containing transformed B cells secreting anti-GII.4 Sydney 2012 VLP antibodies were fused with HMMA2.5 myeloma cells using a CytoPulse Sciences Generator. After fusion, hybridomas were plated in selection medium containing 100 µM hypoxanthine, 0.4 µM aminopterin, 16 µM thymidine and 7 µg/mL ouabain. After two weeks, hybridomas were screened for production of human antibodies reacting with GII.4 Sydney 2012 VLPs and then cloned biologically using single cell sorting on a FACSAria III flow cytometer in the Vanderbilt Flow Cytometry Shared Resource.

Competition-binding assay. To identify groups of antibodies binding to similar antigenic sites on norovirus GII.4 Sydney 2012, the inventors performed biolayer interferometry using an Octet® Red96 or Octet® HTX biosensor system (FortéBio). The Octet® HTX is a high-throughput biosensor system that was used to validate results obtained from the Octet® Red96 system. With both biosensor systems, antibodies and antigen were diluted in 1× kinetic buffer (FortéBio 18-5032). Glutathione S-transferase (GST)-tagged GII.4 Sydney 2012 P domain dimers were immobilized onto anti-GST biosensor tips (FortéBio 18-5096). The P domain dimers were coated onto the biosensor tip by immersing the tip in a solution containing dimers at a concentration of 5 µg/mL. The biosensor tip with the bound P domains was washed and then submerged into a well containing 50 µg/mL of the first antibody and then dipped into another well containing 50 µg/mL of the second antibody. If binding of the first antibody still resulted in greater than 66% of binding of the second antibody, the result was interpreted to be no competition. If binding of the second antibody was between 34 and 66% in the presence of the first antibody, there is believed to be partial competition. If 33% or less binding of the second antibody was noted in the presence of the first, both antibodies are believed to be in competition with each other. Antibodies then were clustered based on their binding patterns.

Stool filtrates. To prepare 10% stool filtrates, 4.5 mL of sterile PBS was added to 0.5 g of GII.4 Sydney 2012 positive stool sample. The stool suspension was sonicated using a cup horn sonicator and centrifuged at 1,500×g for 10 minutes at 4° C. Supernatant was collected and transferred to a new tube and centrifuged once again at 1,500×g, for 10 minutes at 4° C. The resulting supernatant then was passed serially through 5 µm, 1.2 µm, 0.8 µm, 0.45 µm and 0.22 µm filters, and aliquoted and frozen at −80° C.

Expression and purification of GST-GII.4 Sydney 2012 P domain. P1 and P2 domain sequences of GII.4 Sydney 2012, AFV08795.1, VP1 were cloned into the pGEX-4T-1 expression vector with a glutathione S-transferase (GST) tag and thrombin cleavage site. The P domain was expressed in $Escherichia\ coli$ BL-21 cells and purified using standard column chromatography techniques with a prepacked Glutathione Sepharose Fast Flow column (GE Healthcare). GST-tagged proteins were eluted using 50 mM Tris-HCl, 10 mM reduced glutathione, pH 8.0 and stored at 4° C.

GII.4 Sydney 2012 virus neutralization assay. Human intestinal enteroids (HIEs) were generated and cultured as described previously (Ettayebi et al., 2016). Briefly, HIEs were grown as three-dimensional cultures in Matrigel (Corning) for 5 days and then plated as cell monolayer cultures in 96-well plates. Before plating, 96-well plates were pre-coated with collagen IV (Sigma) at 33 µg/mL in sterile cold water for 1.5 hours at 37° C. Three-dimensional HIEs were collected in 0.5 mM ethylenediaminetetraacetic acid diluted in ice-cold Dulbecco's PBS, no calcium, no magnesium (Life Technologies, Cat #14190-144) and spun down at 200×g for 5 minutes at 4° C. in a swinging bucket rotor. The pellet then was suspended in 0.05% trypsin/0.5 mL ethylenediaminetetraacetic acid and incubated at 37° C. for 4 minutes. Trypsin then was inactivated with complete medium without growth factors [CMGF(−)] supplemented with 10% fetal bovine serum (FBS). The resulting pellet was suspended and passed through a 0.4 µm cell strainer and spun down at 400×g at room temperature for 5 minutes. The pellet then was suspended in complete medium with growth factors [CMGF(+)] containing 10 µM Y-27632 (Sigma-Aldrich; Y0503) and seeded into a 96-well plate. After 24 hours, the culture medium was removed and replaced with differentiation medium. Cells were differentiated for 5 days. HuNoV GII.4 Sydney 2012 (TCH12-580) (Ettayebi et al., 2016) stool filtrate ($2\times10^7$ genome equivalents/4) was used to test neutralization. Serial dilutions of the mAbs were prepared in CMGF(−) medium and each dilution was pre-incubated with $2.5\times10^5$ genome equivalents of GII.4 Sydney 2012 at 37° C. for 1 hour. Samples were diluted with equal volume of CMGF(−) medium supplemented with 1000 µM sodium glycochenodeoxycholate. Monolayers then were inoculated with pre-incubated samples. At 1-hour post-infection (HPI), monolayers were washed twice and incubated with differentiation medium supplemented with 500 µM glycochenodeoxycholate. After 1 and 24 HPI, cells and medium were collected and RNA was extracted using King-Fisher Flex Purification System and MagMax Viral RNA Isolation kit. For RT-qPCR, a primer pair (COG2R/QNIF2d) and probe (QNIFS) (Loisy et al., 2005; Kageyama et al., 2003) were used with qScript XLT One-Step RT-qPCR ToughMix reagent with ROX (Quanta Biosciences). Reactions were performed on an Applied Biosystem StepOne Plus thermocycler. A recombinant HuNoV RNA transcript was used to create a standard curve to quantitate viral genome equivalents in new RNA samples.

Example 2—Results

Isolation of GII.4 VLP-reactive human mAbs. The first step here was to isolate naturally occurring human mAbs to GII.4 Sydney 2012 virus capsid protein from human subjects with prior GII.4 Sydney 2012 virus infection. The inventors used PBMCs collected from subjects with previous history of laboratory-confirmed GII.4 Sydney 2012 virus infection to generate human hybridoma cell lines secreting GII.4 VLP-reactive human mAbs. PBMCs were transformed with EBV and supernatants then were collected from lymphoblastoid cell lines and screened by ELISA for binding to GII.4 Sydney 2012 VLPs. Recombinant expression of norovirus genome ORF2 and ORF3 in a baculovirus expression system were used to generate VLPs that are antigenically and morphologically indistinguishable from native virions (Jiang et al., 1992). Antibodies that bound to VLPs were detected using horseradish peroxidase conjugated anti-λ or -κ (light chain secondary antibodies. The inventors used an anti-light chain secondary antibody for detection in order to isolate antibodies of varying Ig heavy chain isotypes. Previous studies have noted the presence of diverse isotypes in the human polyclonal antibody response to infection, including an increase in IgA, IgG, and IgM antibodies in serum (Iritani et al., 2007; Gray et al., 1994), and the inventors have shown previously that human IgAs can be more potent than IgGs in blocking GI.1 VLPs from binding to histo-blood group antigens (HBGAs) (Sapparapu et al., 2016). Transformed B cell lines corresponding to supernatants that contained antibodies that bound to GII.4 VLPs were fused with myeloma cells to create human mAb-secreting hybridoma cells. They isolated a panel of 25 hybridomas secreting VLP-reactive antibodies (21 IgGs and 4 IgAs) from 7 different donors (Table A and Supplementary Table 1).

Figure 4:
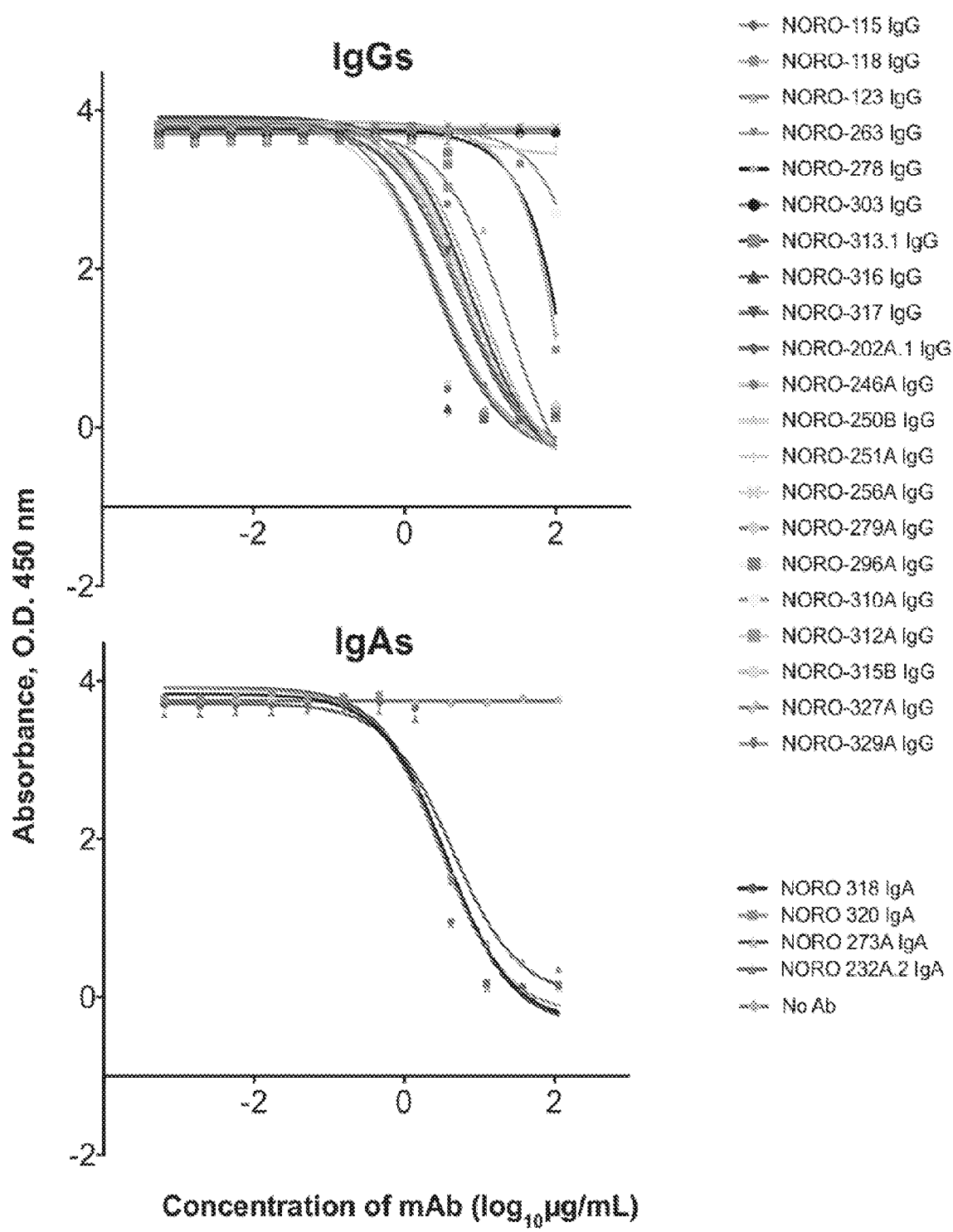
FIG. 4. Characterization of blockade activity of GII.4 Sydney VLPs using isolated mAbs. Blockade potential of serially diluted mAbs or a no-antibody control for GII.4 Sydney 2012 VLP binding to porcine gastric mucin was measured.

MAb binding and blockade of GII.4 VLPs. Next, the inventors sought to determine how well the antibodies bound to GII.4 Sydney 2012 antigens, and to identify if any blocked attachment of VLPs to surrogate receptor molecules. Half-maximal effective concentrations ($EC_{50}$) were determined for the panel of GII.4 Sydney 2012 VLPs reactive mAbs using indirect ELISA. For the 21 isolated IgGs, $EC_{50}$ values ranged from 0.1 to 6.2 µg/mL (Table A and Supplementary FIGS. 1A-C). For the 4 isolated IgAs, $EC_{50}$ values ranged from 0.1 to 0.4 µg/mL. They initially used a surrogate system to assess the neutralizing capacity of all 25 mAbs. The presence of antibodies that block VLPs from binding to HBGAs in vitro correlates with protection against clinical NoV gastroenteritis (Atmar et al., 2015; Czako et al., 2015). To test blockade potential, serial dilutions of isolated mAbs were pre-incubated with GII.4 VLPs, and then VLP-antibody complexes were added to microtiter plates that had been coated previously with porcine gastric mucin type III (PGM) (Reeck et al., 2012). Previous studies have validated PGM as a reliable substrate to be used in VLP blockade assays (Lindesmith et al., 2012a). The inventors then determined $EC_{50}$ values for the 4 IgAs and 13 IgGs, which ranged between 2.4 to 23.9 μg/mL (FIGS. 1A-B, and FIG. 4). Blockade activity was not detected for 8 of the IgGs when using antibody concentrations as high as 100 μg/mL. The inventors determined the antibody variable gene heavy and light chain sequences for 17 of the 25 isolated mAbs (Supplementary Table 1). All 17 mAbs, both mAbs that did and did not inhibit GII.4 VLP binding to PGM, had distinct variable gene sequences, suggesting that blockade response is not restricted to a specific genetic sequence motif in antibody repertoires.

Hemagglutination inhibition (HAI) assay confirms mAb blockade activity. The inventors used a second functional assay to confirm the activity they observed in the blockade assay above. Previous studies have shown that an additional surrogate system to determine mAb neutralization is HAI, and that HAI serum antibody levels correlate with protection from symptomatic infection (Czako et al., 2012; Lindesmith et al., 2012a). They inventors used serial dilutions of the isolated mAbs and pre-incubated them with GII.4 Sydney 2012 VLPs. VLP-antibody complexes were then added to human type O+ RBCs. HAI activity was assessed visually, and HAI titers were determined (FIG. 1A). The majority of the mAbs, about 84%, had HAI activity similar to that of the measured blockade activity. Four mAbs differed in these measures, having either a greater than 2-fold difference in activities or exhibiting only HAI activity or only blockade activity.

Neutralization assay using stem-cell derived enteroids. Inhibition of replication of GII.4 Sydney 2012 virus by mAbs NORO-250B, -263, -320, -273A, -318 and a non-GII.4 VLP binding control antibody, 2D22, were tested using an intestinal epithelial stem-cell derived in vitro cultivation system. The inventors selected two IgGs, NORO-263 and -250B and three IgAs, NORO-320, -273A and -318. These five mAbs were chosen so that they could test neutralization by representative mAbs belonging to the three major antigenic sites they identified on the GII.4 Sydney 2012 P domain and to test at least two mAbs belonging to each isotype (FIG. 2). Neutralization was measured by comparing the percent reduction of genome equivalents when compared to a no-antibody control within each assay using RT-qPCR (FIG. 1C). A no-antibody control was used in each assay to normalize for any variability between experiments. Variability was noted due to the high sensitivity when using genome equivalents to measure replication. To account for these differences, the inventors used six replicates for each mAb concentration tested within each assay and for the no-antibody control. They then averaged the genome equivalents from two separate assays for each antibody to obtain an $IC_{50}$ value. To verify that equal amounts of virus were added to each monolayer, each assay was performed in duplicate and RNA was collected from one assay at 1 HPI and from the other at 24 HPI. Four of the five antibodies tested, NORO-250B, -263, -273A and -318, had approximately 5 to 883-fold lower $IC_{50}$ values compared to blockade $EC_{50}$ values, or between 17 and 1,227-fold lower than HAI titers (FIGS. 1A and 1C). NORO-320 had a higher $IC_{50}$ in comparison to its blockade $EC_{50}$ or HAI titer. The dengue virus mAb 2D22 used as a similarly prepared negative control did not exhibit concentration-dependent inhibit of replication of GII.4 Sydney 2012 virus. Previous studies with polyclonal serum have shown that neutralization $IC_{50}$ values of GII.4 and GII.3 noroviruses are lower in comparison to blockade $EC_{50}$ values (Ettayebi et al., 2016). These studies as well as these data suggests that the HIE neutralization assay is likely more sensitive than the HBGA blockade or HAI assays.

Figure 5:
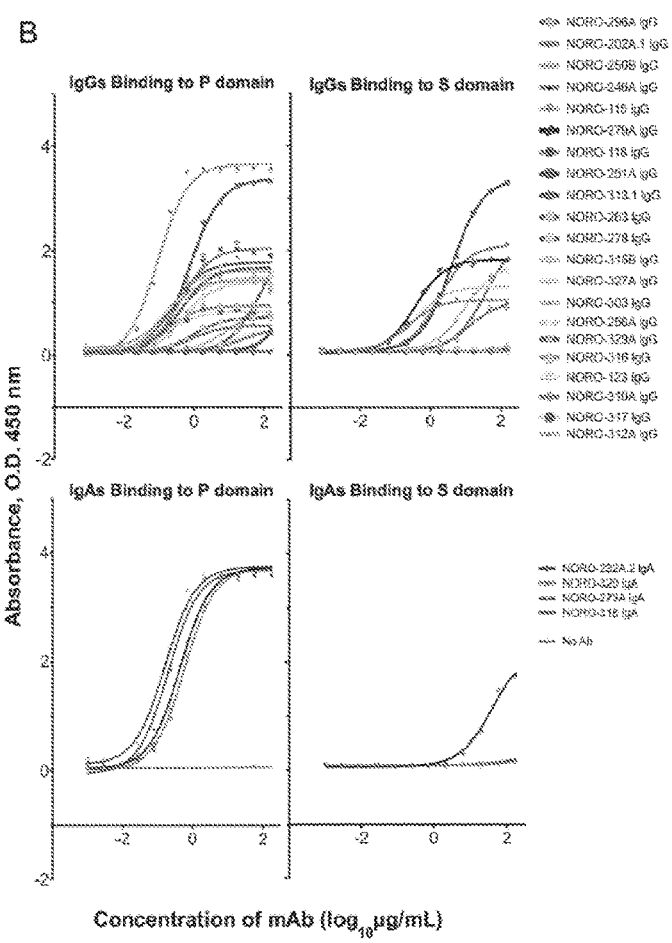
FIGS. 5A-B. Half-maximal binding concentrations (EGO of purified mAbs to GII.4 Sydney 2012 protruding (P) or shell (S) domain.
Figure 6:
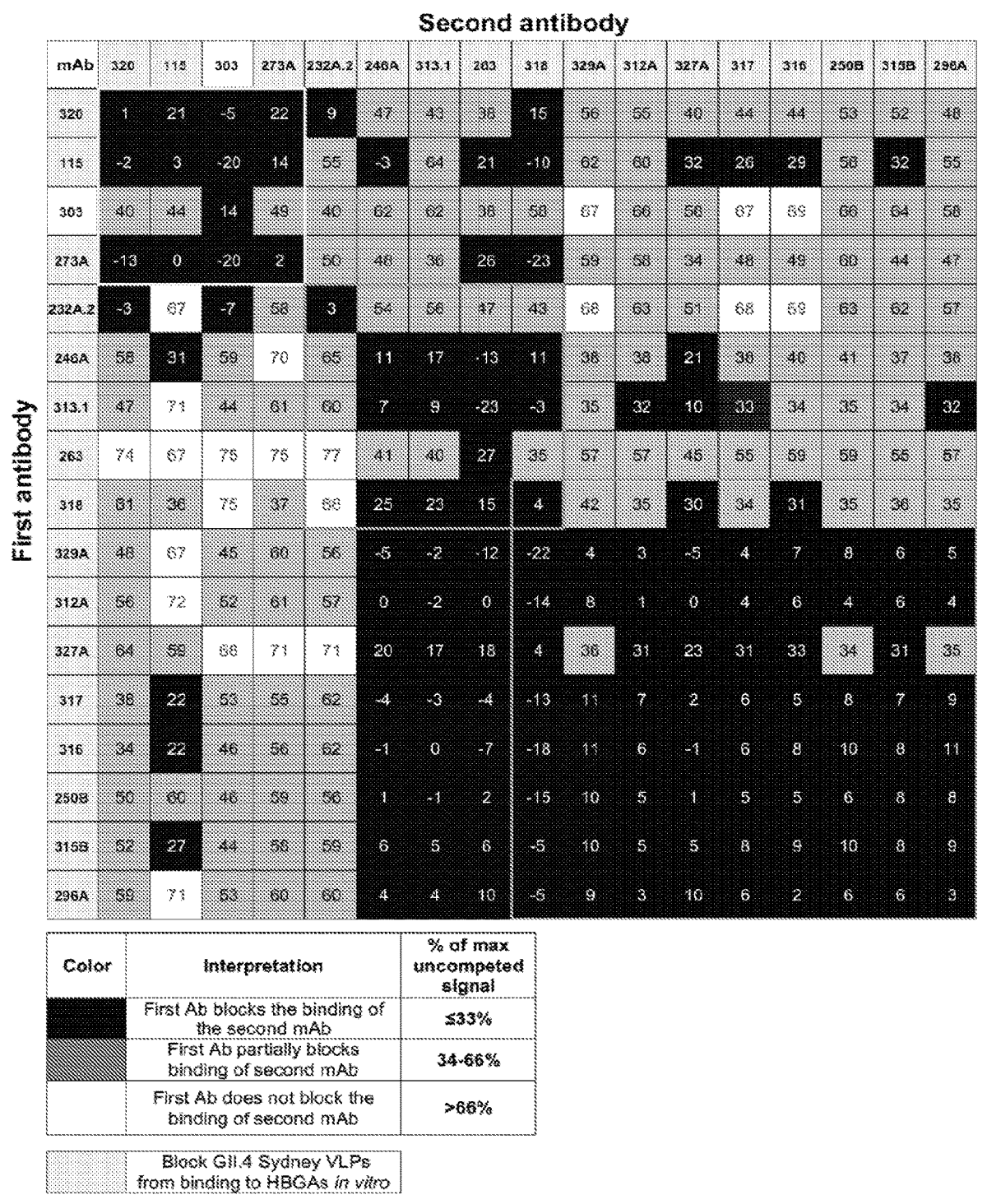

Binding studies using GII.4 Sydney 2012 protruding (P) domain dimers and shell (S) domain. The inventors next sought to determine if the antibodies were binding to the P or S domains of the major capsid protein VP1. Glutathione S-transferase (GST)-tagged recombinant GII.4 Sydney 2012 P domain dimers were expressed and purified using affinity column chromatography, as previously described (Choi et al., 2008). P domain dimers or recombinantly expressed S domains then were used as antigen for an indirect ELISA assay with serial dilutions of each mAb to determine if the 25 isolated mAbs were specific to the P or S domain of the GII.4 major capsid protein VP1. The VP1 region is divided into the S domain, which is not expressed on the recombinant GST-GII.4 P domain dimers, and the P1 and P2 subdomains that are expressed in the dimers. The P domain is the surface-exposed protruding region of the norovirus virion and also believed to include determinants for host cell attachment and antibody binding epitopes (Debbink et al., 2012; (Lindesmith et al., 2012b; Lochridge et al., 2005). The S domain is connected to the P domain by a flexible hinge region and forms the interior core of the viral capsid. The S domain has the highest degree of genetic sequence conservation of any protein domain in diverse norovirus strains (Parra et al., 2013). When binding was tested by ELISA, 20 of the 25 isolated mAbs bound to the GST-GII.4 P domain (FIGS. 5A-B). The five mAbs that did not bind to the P domain did bind to the S domain. NORO-329A, -312A, -296A and -232A.2, bound to both the P and S domain proteins, indicating that these antibodies likely bind to a quaternary epitope on the GII.4 Sydney 2012 major capsid protein. Isolated mAbs and GII.4 P domain dimers also were used for competition-binding studies. The inventors used a real-time biolayer interferometry biosensor system to identify potential major antigenic sites recognized by the GII.4 Sydney 2012 P domain binding mAbs. Neutralizing mAbs and mAbs that did or did not block GII.4 Sydney 2012 VLPs from binding to PGM were classified into three major competition-binding groups, with some overlap between two groups (FIG. 2). Despite multiple attempts, they were not able to detect binding using biolayer interferometry for 2 of the 20 mAbs that bound to the GII.4 Sydney 2012 P domain by ELISA. Competition-binding studies were performed using the Octet® RED96 and Octet® HTX systems, which are both instruments that can measure biomolecular interactions. The HTX system is a high-throughput system that has the ability to compete all 18 P domain binding mAbs within the same experiment. The RED96 system was only able to compete mAbs in groups of 8. Using data from the RED or HTX experiments, the inventors noted three major competition-binding groups on the GST-GII.4 Sydney 2012 P domain (FIG. 2 and FIG. 6). By using both instruments, in two independent laboratories, they were able to validate the reproducibility of the results.

Figure 7:
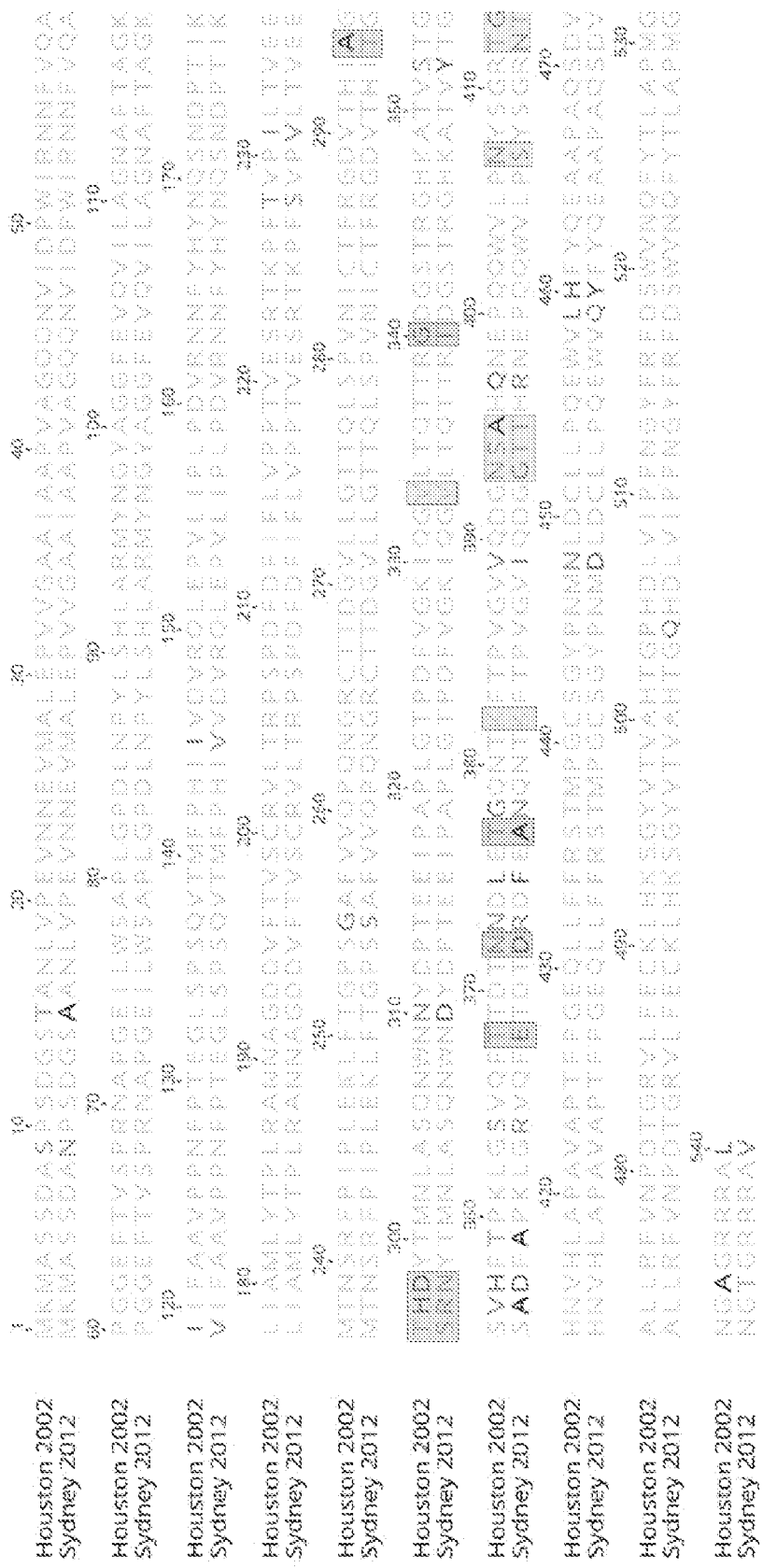
FIG. 7. Predicted blockade epitopes on amino acid sequence alignment of GII.4 Houston 2002 and Sydney 2012. Amino acid sequence alignment of the major capsid protein of GII.4 Houston 2002 (SEQ ID NO: 205) and Sydney 2012 (SEQ ID NO: 206) noroviruses. Boxes indicate predicted blockade epitopes described in (Lindesmith et al., 2012a). Epitope A is amino acids 294, 296-298, 368 and 372. Epitope B is amino acids 333 and 382. Epitope C is amino acids 340 and 376. Epitope D is amino acids 393 and 395. Epitope E is amino acids 407, 412 and 413.
Figure 8:
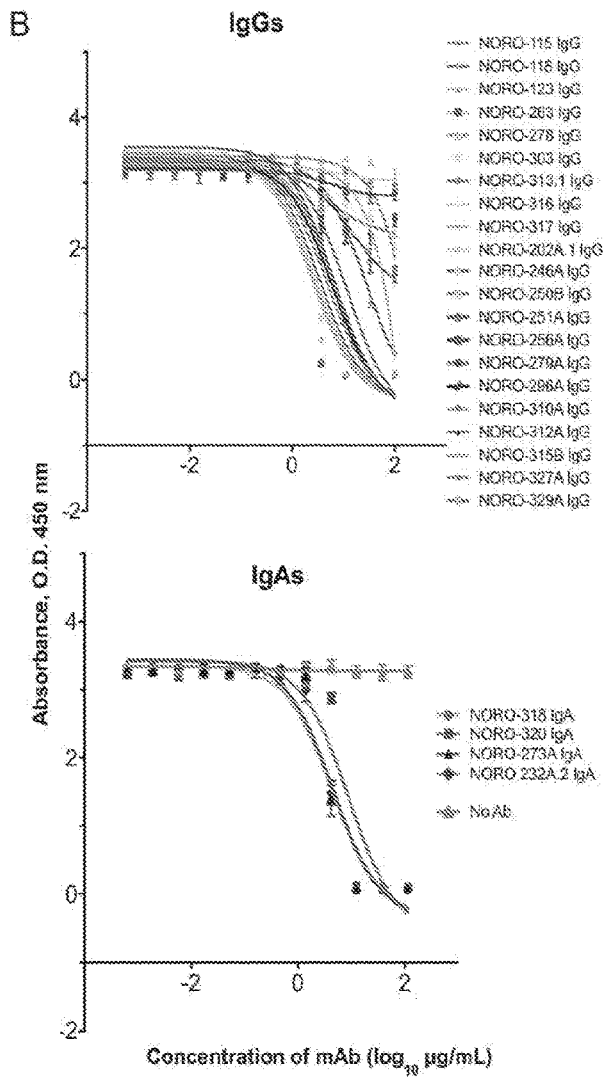
FIGS. 8A-B. Half-maximal binding and blockade concentrations (EGO of purified mAbs to GII.4 Houston 2002 VLPs.

The emergence of new GII.4 strains has been associated with the evolution of the GII.4 major capsid protein and antigenic variation (Karst et al., 2015). To measure the reactivity of the inventors' panel of mAbs for another GII.4 strain, the inventors tested binding reactivity and blockade activity to a GII.4 Houston 2002 (ABY27560.1) variant. About 93% of the amino acid sequence of the major capsid protein is conserved between GII.4 Houston 2002 and Sydney 2012, but there are remarkable differences among predicted GII.4 blockade epitopes (FIG. 7). All 25 mAbs exhibited binding reactivity to GII.4 Houston 2002 antigen (FIGS. 8A-B). Only 3 mAbs, NORO-115, -329A, and -318 had a greater than 10-fold higher binding $EC_{50}$ value when compared to GII.4 Sydney 2012 VLPs (Table A). The 18 mAbs that either blocked with $EC_{50}$ values <100 µg/mL or had HAI titers <15 µg/mL all blocked GII.4 Houston 2002 VLPs from binding to PGM. GII.4 Houston 2002 and Sydney 2012 had different amino acid sequences in four of the five predicted blockade epitopes, these results suggest the potential existence of additional blockade epitopes or the use of Epitope B, which was conserved among both strains (FIG. 7).

Example 3—Discussion

Here the inventors report the first instance of neutralization of HuNoV by mAbs and describe a large panel of human mAbs that neutralize the pandemic GII.4 Sydney 2012 strain. Previously it was not possible to test norovirus neutralization directly because of the lack of a reliable in vitro culture system for norovirus replication. A surrogate system to predict neutralization was devised and used to study inhibition of the interaction between VLPs and HBGAs. The presence of blocking antibodies in serum correlates with protection from clinical gastroenteritis induced by HuNoV infections, and therefore the HBGA blocking assay has been considered a surrogate system for HuNoV neutralization (Reeck et al., 2010). Recently, the inventors developed an in vitro system using human enteroids to replicate multiple HuNoV strains[13]. Here, they used that system to identify the first norovirus human mAbs with demonstrated virus neutralizing activity. Of the 25 human mAbs isolated in this study, 17 of them blocked GII.4 Sydney 2012 VLPs from binding to PGM at concentrations as low as 2.4 µg/mL. The 18 mAbs that blocked GII.4 Houston 2002 from binding to PGM at concentrations as low as 2 µg/mL, also either blocked GII.4 Sydney 2012 VLPs from binding to PGM or inhibited hemagglutination at the concentrations tested. Interestingly, 13 of the 14 IgGs that blocked GII.4 Houston 2002 VLPs from binding to PGM did so at a lower $EC_{50}$ value in comparison to blockade $EC_{50}$ values for GII.4 Sydney 2012. This finding could indicate that donors had prior exposure to an earlier norovirus variant similar to GII.4 Houston 2002. This panel also contains the first reported human IgA mAbs that bind to GII.4 Sydney 2012 VLPs and also inhibit receptor binding. The inventors tested neutralization of live GII.4 Sydney 2012 HuNoV using the mAbs NORO-263, -320, -250B, -273A and -318. These antibodies were selected for testing so that they could investigate differences in neutralizing activity between mAbs of differing isotypes, those which belong to different competition-binding groups, and those with different binding and blockade $EC_{50}$ values. NORO-250B, -263, -273A and -318, had lower neutralization $IC_{50}$ values in comparison to blockade $EC_{50}$ values and HAI titers. Surprisingly, NORO-320 had an $IC_{50}$ value about 2-fold higher than its HAI titer and about 3-fold higher than its blockade $EC_{50}$ value. Previous studies have noted differences in blockade potency of GI.1 VLPs among human IgG and IgA mAbs with blockade potency being enhanced for IgAs (Sapparapu et al., 2016). To draw a similar conclusion for GII.4 Sydney 2012 neutralizing human antibodies, it would be essential to test mAbs binding to different epitopes with identical variable domain sequences and distinct isotypes. Such studies could determine if isotype plays a critical role in neutralization of GII.4 Sydney 2012 by human mAbs.

HuNoV-specific antibodies have been described previously, but these were antibody fragments derived from phage display libraries (Huang et al., 2014), murine mAbs from infected mice (Crawford et al., 2015), nanobodies from alpacas immunized with VLPs (Koromyslova and Hansman, 2017), or mAbs isolated from patient PBMCs with an unknown norovirus history of exposure (Lindesmith et al., 2012a). Such antibodies do not provide direct information about the physiologic human humoral immune response to HuNoV infection. The therapeutic potential of mouse mAbs is limited, since they have been shown to induce human anti-mouse antibody responses. There has been little progress in understanding individual HuNoV-specific antibodies in the past because of the difficulty in generating human mAbs with functional activity. Here the inventors used a hybridoma technology (Smith and Crowe, 2015) and circulating B cells from convalescent patients to produce human mAbs. This approach generates hybridoma cell lines from circulating B cells that express naturally occurring and matched heavy and light chain genes. An additional benefit of using this approach is that it does not involve the use of any laboratory animals to produce antibodies. Using this method, they isolated 25 GII.4 Sydney 2012 VLP-reactive mAbs. The majority of these antibodies were neutralizing when tested in a surrogate system for neutralization and all five of the mAbs tested also inhibited replication of live GII.4 Sydney 2012 virus by direct neutralization in vitro. Neutralizing human mAbs have potential for use in prophylactic, therapeutic or diagnostic applications. The inventors currently do not have any drugs available to treat or prevent HuNoV infection, so the inventors' panel of neutralizing mAbs now have the high potential to impact the design of improved diagnostic and therapeutic measures for HuNoV s.

Since the mid-1990s, new antigenically diverse GII.4 pandemic viral strains have emerged continuously every 2 to 5 years, and today these strains continue to be the predominant cause of norovirus outbreaks. In 2012, the epidemic GII.4 Sydney variant emerged in Australia and began spreading globally. Even though blockade epitopes among some contemporary GII.4 strains have been predicted or identified, the inventors have limited information about the neutralization determinants on GII.4 Sydney 2012 viruses (Debbink et al., 2013; Lindesmith et al., 2012a). Here, they determined that there are at least three major antigenic and neutralizing sites on the P domain of GII.4 Sydney 2012 viruses. In the future, defining neutralization epitopes in high resolution with neutralizing antibodies could contribute valuable insights for rational structure-based vaccine design efforts.

HuNoV is one of the leading causes of severe acute gastroenteritis, therefore the global burden of norovirus infection is extremely high in both developed and developing countries. Unfortunately, there is currently no licensed vaccine to prevent norovirus infection. Efforts to design a vaccine have been hindered by the lack of a small animal model or tissue culture model to test neutralization or infection, the antigenic heterogeneity among noroviruses, and uncertainty about the durability of protective immunity (Debbink et al., 2014). Vaccine efforts have focused on the use of monovalent GI.1 or bivalent GI.1/GII.4 virus-like particles or P particle subunits (El-Kamary et al., 2010; Bernstein et al., 2015; Tan et al., 2011). Clinical trials have shown that norovirus VLP vaccines are immunogenic and without frequent serious adverse events (Ramirez et al., 2012; Leroux-Roels et al., 2018). The inventors now have developed a reliable in vitro system to test the replication or inhibition of replication of live noroviruses. Mapping the neutralization or blockade epitopes using the panel of mAbs they isolated against this circulating pandemic strain of norovirus will provide critical information that can be used for the design of future VLP vaccines that can elicit a protective immune response.

Example 4—Materials and Methods

Generation of virus-like particles. Virus-like particles (VLPs) based on norovirus strains GI.1 (M87661), GI.2 (AF435807), GI.3 (AF439267), GII.3 (TCH02-104), GII.4 (AFV08795.1), GII.6 (AF414410), GII.13 (JN899242) and GII.17 (AB983218) were expressed recombinantly and purified as previously described (Jiang et al., 1992). The inventors used a baculovirus recombinant protein expression system for VLP production. The inventors cloned the VP1 and VP2, major and minor, protein capsid sequences from each strain into the transfer vector pVL1392 (Epoch Life Science, Inc). Sf9 insect cells were co-transfected with a transfer vector corresponding to a specific strain and with a bacmid vector. Recombinant baculovirus was isolated and expanded. VLPs were purified from cell culture supernatants using a sucrose and cesium chloride gradient. VLP formation was verified using electron microscopy.

Reactivity to VLPs by ELISA. An ELISA was used to testing binding of human mAbs to VLPs, as was previously described (Alvarado et al., 2018). Each VLP was coated individually at 1 µg/mL on 384-well microtiter plates at 4° C. overnight. Plates then were blocked for one hour at room temperature using 5% nonfat dry milk in PBS with 0.05% Tween-20. For screening and $EC_{50}$ analysis, antibody reactivity to VLPs was detected using horseradish peroxidase (HRP) tagged anti-κ or -λ chain secondary antibodies (Southern Biotech). 1-Step™ Ultra-TMB Substrate Solution (Pierce ThermoFisher) was used to detect HRP activity.

Human subjects. The Vanderbilt University Medical Center Institutional Review Board approved of the participation of the 6 adult subjects used in this study. All participants provided written informed consent before the inventors obtained blood samples. The subjects were healthy with a previous history of acute gastroenteritis.

Human hybridoma generation. Human hybridomas secreting human mAbs were generated as previously described (Alvarado et al., 2018). Briefly, PBMCs were isolated from human subject blood samples using Ficoll-Histopaque and density gradient centrifugation and then cryopreserved. Later, cells were thawed, transformed using Epstein-Barr virus, CpG10103, cyclosporine A and a Chk2 inhibitor and plated in a 384-well plate. Transformed cells were incubated at 37° C. for 7 days, and then expanded into 96-well plates containing irradiated human PBMCs. Four days later, cell supernatants were screened by indirect ELISA for the presence of anti-norovirus VLP cross-reactive mAbs. B cells secreting cross-reactive mAbs were electrofused to HMMA2.5 myeloma cells and plated in medium containing hypoxanthine, aminopterin, thymidine and ouabain. Hybridoma cell lines were incubated at 37° C. for 14 days, and then supernatants were screened by indirect ELISA for productions of cross-reactive mAbs. Cell lines expressing cross-reactive mAbs then were cloned biologically using single-cell fluorescence-activated cell sorting.

Purification of cross-reactive mAbs. After cloning, hybridoma cell lines producing cross-reactive mAbs were expanded gradually from 48-well plates to 12-well plates, T-25, T-75 and eventually to four T-225 flasks for each cell line. Supernatant from each cell line also was screened by ELISA to determine the corresponding light chain for each clone. Following 4-weeks of incubation at 37° C., supernatant from the four T-225 flasks was harvested and filtered through a 0.4-µm filter. The supernatant was filtered using column chromatography, specifically HiTrap KappaSelect and Lambda FabSelect affinity resins (GE Healthcare Life Sciences).

VLP-carbohydrate mAb blockade assay. To test the ability of each mAb to inhibit the interaction between the selected VLPs and glycans in vitro, the inventors used a blockade assay. As previously described, the inventors coated microtiter plates with 10 µg/mL of pig gastric mucin Type III (Sigma) for 4 hours at room temperature. Plates then were blocked overnight at 4° C. in 5% nonfat dry milk. VLPs at 0.5 µg/mL were pretreated with serially diluted concentrations of each mAb for 1 hour at room temperature. VLP-mAb complexes were added to the PGM-coated and blocked microtiter plates. After 1 hour of incubation, the plates were washed 3 times with PBST and the same was done in between each step. Bound VLPs were tested using murine serum containing anti-GI.3, GII.4, GII.6 or GII.17 polyclonal antibodies, followed by an HRP conjugated goat anti-mouse IgG human adsorbed antibody. Optical density was measured at 450 nm using a Synergy HT Microplate Reader (BioTek).

Expression and purification of protruding and shell domain for selected NoV strains to be used in Ab binding studies. In order to map the epitope of cross-reactive mAbs, the inventors first recombinantly expressed P1 and P2 domain sequences or shell domain of GI.3 (AF439267), GII.4 (AFV08795.1), GII.6 (AF414410), GII.13 or GII.17 (AB983218). P domain sequences were cloned into the pGEX-4T-1 expression vector with a GST tag and thrombin cleavage site. The P domain then was expressed in *Escherichia coli* BL-21 cells and purified using a Glutathione Sepharose Fast Flow Column (GE Healthcare) and column chromatography. The S domain sequences were cloned into pVL1392 and co-transfected with a bacmid vector into Sf9 insect cells. Recombinant baculovirus particles then were harvested and used to inoculate Sf9 cells. S domain particles were then purified from the inoculated Sf9 cell culture supernatant using a sucrose and a cesium chloride cushion gradient.

Expression, purification and crystallization of GII.4 P domain and NORO-320 Fab. The sequence for the GII.4 protruding domain was cloned into the expression vector pMal-C2E (New England BioLabs). The expression vector includes a N-terminal $His_6$-maltose binding protein (MBP) tag and a tobacco etch virus (TEV) protease cleavage site between the MBP and P domain sequence. The P domain was expressed in *E. coli* BL21(DE3) and purified using an AffiPure Ni-NTA agarose bead column (GenDepot). The His-MBP tag was then removed using TEV protease and separated from the P domain by purifying it once again using His-Trap (GE Healthcare), MBPTrap (GE Healthcare) affinity columns and size exclusion chromatography. Finally, the purified P domain was concentrated and stored in 20 mM Tris-HCl buffer (pH 7.2) containing 150 mM NaCl, and 2.5 mM $MgCl_2$.

The nucleotide sequences of the variable domain of mAb NORO-320 was optimized for mammalian expression and synthesized (Genscript) for expression and purification of recombinant Fab. The heavy chain fragment was cloned into a vector for expression of recombinant human Fabs (McLean et al., 2000). The light chain was cloned into a vector for light chain. Each vector was transformed independently into *E. coli* cells, and DNA was then purified. Both the heavy and light chain encoding vectors were transfected into CHO cells using an ExpiCHO™ expression system. Cell supernatant was collected, centrifuged and filtered using a 0.45 μm filter. NORO-320 Fab was purified by affinity chromatography using a KappaSelect (GE Healthcare).

Purified GII.4 P domain and NORO-320 Fab were combined in a 1:1.5 molar ration and incubated for 1 hour at 4° C. The mixture was passed through an S75pg 16/60 gel filtration column, and the peak corresponding to the complex was collected. The size of the complex and presence of both proteins was validated on an SDS-PAGE gel. The peak fractions were then pooled and concentrated to 10 mg/mL for crystallization trials. Crystallization screening using hanging-drop vapor diffusion method at 20° C. was set up using a Mosquito nanoliter handling system (TTP LabTech) with commercially available crystal screens, and crystals were visualized by using a Rock Imager (Formulatrix). The GII.4 P domain-NORO-320 Fab complex crystallized in a buffer containing 0.1 M BIS-TRIS prop 8.5 pH, 0.2 M KSCN, 20% w/v PEG 3350. Crystals diffracted to 2.25 Å resolution.

Diffraction, data collection, and structure determination. X-ray diffraction data for the GII.4 Sydney 2012 P domain-Fab NORO-320 crystals were collected on the beamline 5.0.1 at Advanced Light Source (Berkeley, CA). Diffraction data were processed using HKL2000 (Z. Otwinowski and W. Minor, 1997). The previously published GII.4 (strain TCH05) P domain structure (PDB ID 3SJP) and the neutralizing Fab 5I2 (PDB ID 5KW9) were used as the search models by molecular replacement using program PHASER (McCory et al., 2007). Iterative cycles of refinement and further model building were carried out using PHENIX (Adams et al., 2010) and COOT programs (Emsley, P., and K. Cowtan, 2004). During the course of the refinement, and following the final refinement, the stereochemistry of the structures was checked using Molprobity (molprobity.biochem.duke.edu/). Data refinement and statistics are given in Table B. The interactions between P domain and the Fab for NORO-320 were analyzed using LigPlot+v.2.1 (Laskowski et al., 2011). Figures were prepared using Chimera (Pettersen et al., 2004).

Example 5—Results

Isolation of broadly binding anti-NoV human mAbs. To isolate cross-reactive NoV human mAbs, the inventors used EBV and additional B cell stimuli to transform memory B cells in PBMCs obtained from patients who were overall healthy but with a previous history of acute gastroenteritis, as previously described (Sapparapu et al., 2016). A week later, transformed PBMCs supernatants were tested by ELISA to screen for the expression of mAbs that bound to more than one representative strain NoV VLP. The VLPs used to screen were NoV GI.1, GI.2, GI.3, GII.3, GII.4, GII.6, GII.13 or GII.17. Each VLP was coated individually and blocked on a microtiter plate before the screening. The bound antibodies were detected using alkaline phosphatase conjugated goat anti-human κ or λ chain secondary antibodies to capture binding activity by any antibody isotype. Wells that contained transformed B cells expressing mAbs that recognized more than one VLP then were expanded. B cells secreting anti-NoV mAbs were rescued by hybridoma formation. Binding reactivity to pandemic GII.4 Sydney 2012 was previously characterized for 5 of the mAbs included in the inventors' panel (Alvarado et al., 2018). The heavy and light variable gene regions were sequenced for all 12 mAbs and the V, D, J and other variable gene sequence features were analyzed (Supplemental Table 2) (Brochet et al., 2008). Each of the mAbs had unique variable gene sequences, suggesting that cross-reactivity was not limited to one antibody clonotype.

Figure 9:
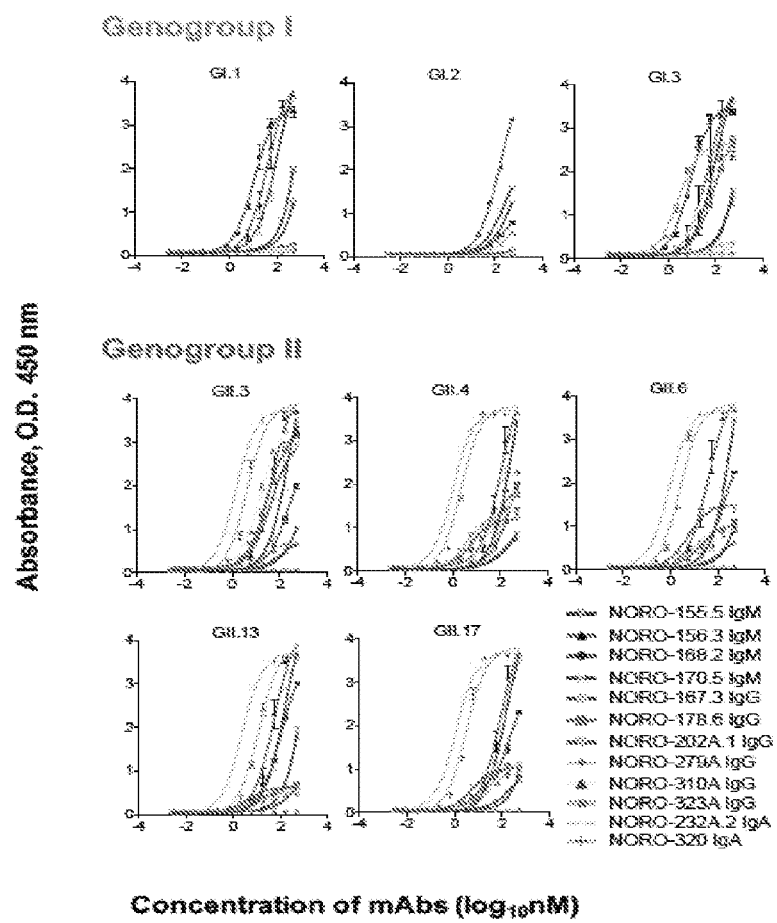
FIGS. 9A-B. Binding activity of cross-reactive human mAbs to GI and GII VLPs. An indirect ELISA was used to assess binding activity of 12 human mAbs to GI.1, GI.2, GI.3, GII.3, GII.4, GII.6, GII.13 or GII.17 VLPs.

Binding and blockade activity of cross-reactive mAbs to NoV GI and GII VLPs. To assess binding reactivity and blockade function of the 12 mAbs, the inventors used indirect ELISA and a VLP blockade assay. The concentration of each mAb was normalized first for the number of antigen binding sites. The inventors then tested binding starting at a concentration of 500 nM, followed by 11 serial dilutions. Each concentration was tested in duplicate, and the complete experiment was repeated 3 times. They used these data to determine the $EC_{50}$ value of each mAb when binding to NoV GI.1, GI.2, GI.3, GII.3, GII.4, GII.6, GII.13 or GII.17 VLPs (FIGS. 9A-B). The inventors noticed 3 distinct binding patterns. NORO-168.2, -156.3 and -170.5, all IgMs, each exhibited wide breadth by binding to all VLPs tested. Both IgAs, NORO-232A.2 and -320, as well as NORO-167.3 and -202A.1, both IgGs, exhibited specificity of binding only for GII variants. The remaining mAbs, NORO-155.5, -178.6, -279A, -310A and -323A reacted with at least one GI and GII strain.

Figure 10:
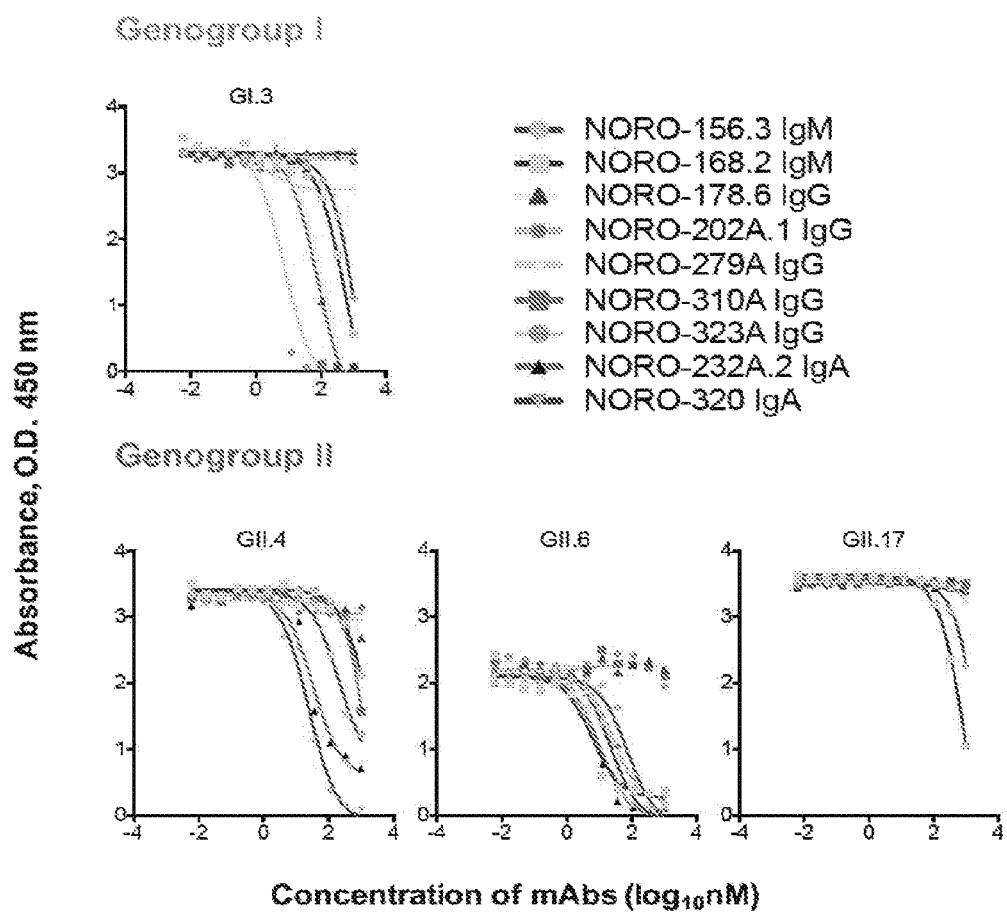
FIGS. 10A-B. Blockade activity of cross-reactive human mAbs for GI or GII VLPs. Blocking of VLP binding to PGM was used as a surrogate system to test neutralization of GI.3, GII.4, GII.6, or GII.17 VLPs using the indicated human mAbs.

To determine if any of the isolated cross-reactive mAbs had functional activity, the inventors used a surrogate system to analyze neutralization. PGM purified from porcine stomach mucosa contains both H and Lewis antigens, α-1,2-fucose and α-1,4-fucose (Lindesmith et al. 2008; Lindesmith et al. 2012; Tian et al., 2010). The use of PGM in blockade assays has been validated previously (Lindesmith et al., 2012). They first tested if GI.1, GI.2, GI.3, GII.3, GII.4, GII.6, GII.13 or GII.17 VLPs could bind to the glycans present in PGM. The optimal concentrations of mAbs were normalized before testing blockade ability and tested at concentrations beginning at 1,000 nM and then diluted serially (FIGS. 10A-B). Blockade studies also were repeated three times. Only GI.3, GII.4, GII.6 and GII.17 bound to PGM. NORO-155.5 and -170.5, both IgMs, and -167.3, an IgG, did not inhibit GI.3, GII.4, GII.6 or GII.17 VLPs from binding to PGM in vitro. 9 of the 12 mAbs blocked at least 1 of the 4 VLPs tested. None of the 8 mAbs with binding reactivity to GII.17 VLPs had any GII.17 blockade activity. The absence of GII.17 blockade could be due to the broad binding HBGA spectrum of GII.17 NoVs and the glycan heterogeneity present in PGM.

Binding to GI.3, GII.4, GII.6 or GII.17 variant protruding (P) vs shell (S) domains. The major capsid protein, VP1, which forms the icosahedral capsid, is divided into the protruding (P) and shell (S) domains (Prasad et al., 1996). To map where the cross-reactive mAbs bind, the inventors first recombinantly expressed and purified the S and P domains of GI.3, GII1.4, GII.6 and GII.17 NoV strains. Antibody binding to S, P and VLPs, containing both S and P, was tested and compared. $His_6$-MBP (maltose binding protein)-tagged recombinant P domains were expressed in *E. coli* and purified using affinity column chromatography, as previously described (Choi et al., 2008). S domain sequences were cloned into pVL1392, expressed using a baculovirus expression system and purified using a sucrose and cesium chloride cushion gradient. P and S domain recombinant proteins were coated at equal concentrations of 2 µg/mL on microtiter plates and blocked with 5% nonfat dry milk in 1×PBS with 0.05% Tween-20. Before adding the mAbs to plates, each mAb was normalized according to the number of antigen binding sites. The inventors tested binding starting at a concentration of 500 nM followed by 11 serial dilutions of each mAb to obtain the half-maximal binding concentrations. Both IgAs, NORO-232A.2 and -320, appeared to bind specifically to the GII.4, GII.6 and GII.17 P domains (FIG. 11). Cross-reactive murine mAbs also have been mapped to the NoV P domain (Parker et al., 2005). NORO-168.2 bound to both the P and S domains of GI.3, GII.4, GII.6 and GII.17, but in all instances had a lower $EC_{50}$ value when bound to the S domain. Some mAbs like NORO-155.5 and -156.3 did not bind to any of the P or S domains tested. Loss of binding may suggest that these mAbs require both the S and P domain to be present for Ab binding.

Structure of NORO-320 Fab in complex with GII.4 P domain. In previous studies, the inventors determined that NORO-320 not only neutralizes GII.4 Sydney 2012 using a surrogate neutralization assay, but also inhibits replication of infectious GII.4 Sydney 2012 virus when using a human intestinal enteroid culture (Alvarado et al., 2018). Here, the inventors discovered that NORO-320 binds broadly across selected GII strains and also blocks GII.6 from binding to PGM. To determine how NORO-320 binds so broadly and neutralizes diverse GII NoV strains, the inventors used X-ray crystallography to identify the structural basis for molecular recognition. They obtained a 2.3 Å resolution structure of NORO-320 Fab in complex with the GII.4 P domain (FIGS. 12A-B). According to the structure, NORO-320 Fab binds perpendicular to the 2-fold axis of the P domain dimer near a region close to the shell domain. This finding shows that NORO-320 Fab does not bind directly or close to the HBGA binding site to inhibit GII.4 VLP-carbohydrate binding or replication of GII.4 Sydney 2012 virus. The inventors considered the possibility that NORO-320 Fab binding allosterically could inhibit HBGA binding by causing a conformational change in the glycan binding site. However, the structural superposition of the GII.4 P domain in complex with NORO-320 and that with the bound HBGA revealed that the P domain dimer structure remains invariant with an r.m.s.d of ~1.1 Å for the matching Cα atoms. The inventors then hypothesized that neutralization of GII.4 by NORO-320 could be a result of steric hindrance since full-length NORO-320 is originally a dimeric IgA (see below).

Figure 14:
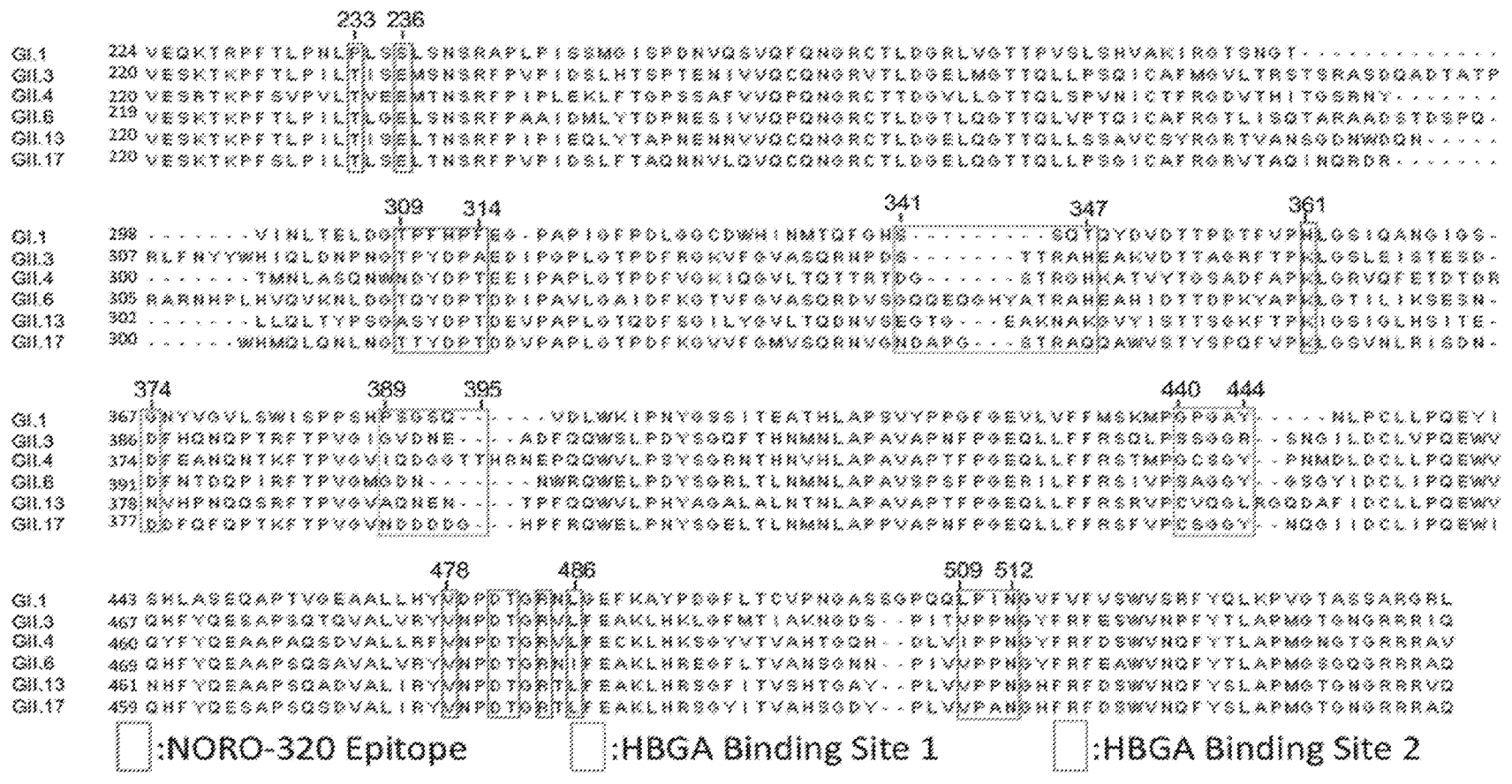

Molecular details of recognition of GII.4 P domain by NORO-320. The crystal structure of NORO-320 Fab-GII.4 P domain complex shows that the antibody makes extensive interactions with the P domain. The Fab binding site on the P domain is formed by residues from the P1 subdomain of one subunit and the P2' subdomain of its dimeric partner (FIGS. 12C-D). The paratope in NORO-320 includes residues from the CDRs of both light and heavy chains. The Fab binding is stabilized by both hydrogen bond and hydrophobic interactions (FIG. 13A). For instance, the sidechain of N479 in the P1 subdomain hydrogen bonds with I54 from CDRH2 and E74 of a non-CDR loop, whereas residues L486, V508, P510, P511, and N512 are involved in hydrophobic interactions with residues from CDRH2 and CDRH3 (FIG. 13B). Residue D312 of the P2' subdomain interact with K119 and Y120 of CDRH3, involving both direct hydrogen bond and hydrophobic interactions (FIG. 13C). In addition to CDRHs, three light chain residues Y35 and Y37 of CDRL1 and L55 of CDRL2 form hydrophobic interactions with P313' and T314' of the P1' subdomain. To understand how NORO-320 can bind to VLPs of various GII strains, the inventors aligned the P domain amino acid sequences of GI.1, GII.3, GII.4, GII.6, GII.13 and GII.17 (FIG. 14). Sequence alignment revealed a 78 to 89% conservation at these sites among the GII strains. In contrast, the P domain sequence in the GI genogroup show significant changes in this region. The high level of sequence conservation could explain why NORO-320 binds broadly among GII.3, GII.4, GII.6, GII.13 and GII.17 strains.

Figure 15:
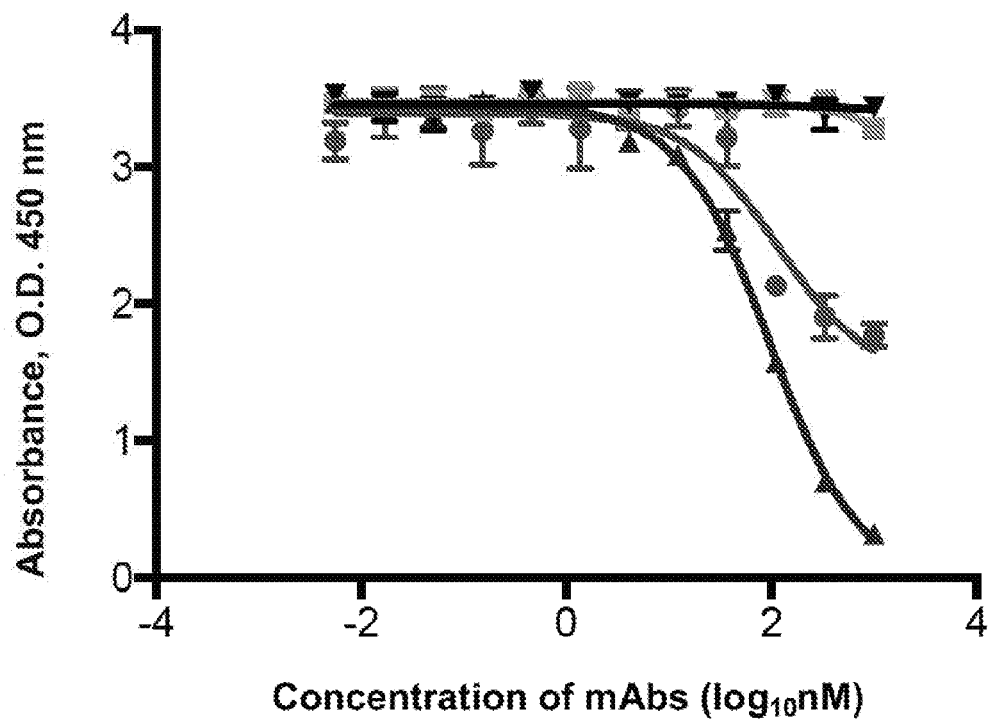
FIG. 15. Blockade of GII.4 VLPs by NORO-320 is a result of steric hindrance. NORO-320 was expressed recombinantly as Fab or IgG forms and purified. GII.4 VLPs were pre-incubated with either NORO-320 Fab, IgG or the original hybridoma-secreted dimeric IgA and added to wells that had been coated previously with PGM. Half-maximal concentrations ($EC_{50}$) for the three antibodies tested are listed. The > symbol indicates blockade $EC_{50}$ value was greater than 1,000 nm.
Figure 16:
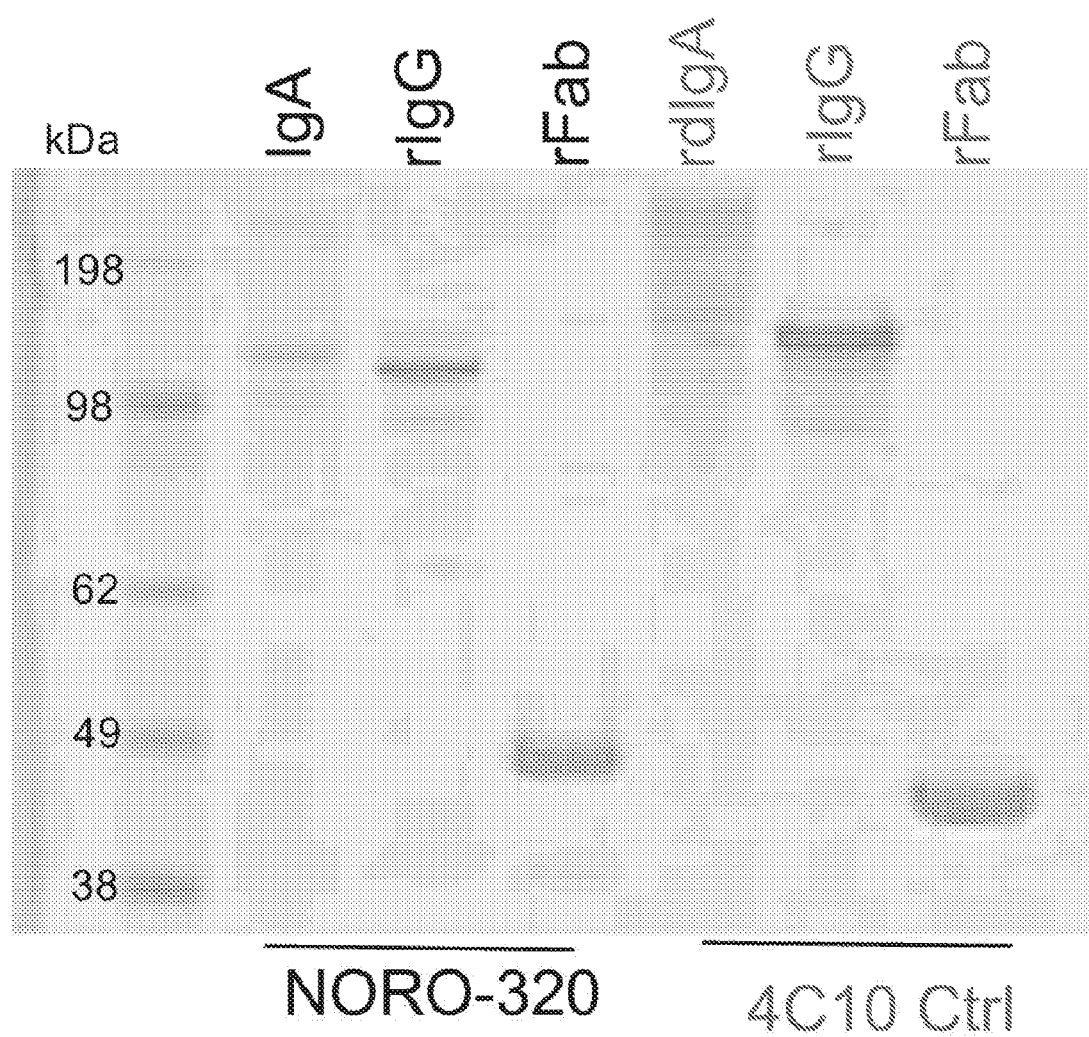
FIG. 16. Verification of molecular assembly of recombinantly expressed NORO-320 variants. NORO-320 was expressed recombinantly and purified in Fab or IgG forms. Fab, IgG and hybridoma dimeric IgA variants were resolved on a SDS-PAGE gel under non-reducing conditions. Recombinant dimeric IgA, IgG and Fab 4C10 was used as a control.

Mechanism of neutralization of NoV by broad human mAbs. To determine if NORO-320 neutralizes GII.4 because it sterically hinders NoV binding to glycans, the inventors tested if blockade activity was influenced by the molecular weight or size of NORO-320. In order to obtain varying forms of NORO-320, they recombinantly expressed the sequence of the variable domain in Fab or IgG heavy chain recombinant expression vectors. The light chain variable sequence also was cloned into a kappa light chain recombinant expression vector. Corresponding heavy and light chains were transfected using Chinese hamster ovary (CHO) cells in an ExpiCHO™ expression system. To verify the molecular weight of the original hybridoma-expressed IgG and each of the recombinantly expressed mAbs, 4 µg of each mAb, along with a set of control mAbs of known molecular weight, were resolved on an SDS-PAGE gel under non-reducing conditions (FIGS. 17A-D). All the mAbs were of the expected apparent molecular weight, dIgA ~350 kDa, IgG ~150 kDa and Fab ~50 kDa. The inventors then tested NORO-320 IgA, recombinant IgG, recombinant Fab or a no mAb control for their ability to inhibit GII.4 Sydney 2012 VLPs from binding to PGM in vitro. As hypothesized based on size, the large NORO-320 IgA had the lowest $EC_{50}$ value followed by NORO-320 recombinant IgG (FIG. 15). Recombinant NORO-320 Fab did not block GII.4 Sydney 2012 VLPs from binding to PGM at concentrations as high as 1,000 nM. This finding indicates that the dimeric NORO-320 likely neutralizes GII strains broadly because of the capacity of this large molecule to mediate steric hindrance to receptor binding (FIGS. 17A-D). The IgMs and IgGs that bind to the S domain of VP1 could potentially neutralize NoVs by disrupting the structural integrity of the virus particles. For example, the IgM NORO-168.2 broadly cross-reacts with GI and GII NoVs by binding to the P and S domains of GI.3, GII.4, GII.6 and GII.17 (FIG. 11). Further understanding of the diverse neutralization mechanisms for circulating human NoVs warrants future structural studies of these human mAbs (FIGS. 17A-D).

Example 6—Discussion

Isolation of naturally occurring broad-spectrum human mAbs to NoV holds great promise for the discovery of new candidate therapeutics, as well as identifying critical epitopes for the rational design of new structure-based broadly protective NoV vaccines. In the past, the genetic and antigenic diversity across circulating strains of NoV has made the generation of a broadly immunogenic vaccine extremely difficult. The primary goal of this study was to define the molecular and structural determinants of cross-reactivity and blockade, or neutralization, using human mAbs to circulating strains of HuNoV. Previous studies have characterized the antigenic landscape of specific HuNoV strains, but with the rapid emergence of new genetically diverse strains, there is a need to map new immunogenic epitopes. This new information also can build upon previous studies to help track the evolution of HuNoVs (Lindesmith et al., 2013). Identification of antigenic epitopes using human mAbs also will provide insight into the immunogenicity of NoVs in humans.

Here, the inventors described the isolation of 12 anti-NoV cross-reactive human mAbs, 4 IgMs, 6 IgGs, and 2 IgAs, from subjects with a previous history of acute gastroenteritis. To determine the functional activity of the isolated mAbs, they used a previously validated surrogate blockade assay that measures the inhibition of VLPs from binding to glycans in vitro (Reeck et al., 2010). Not all of the strains tested bind to the same glycan, so the inventors were only able to test the inhibition of binding for NoV VLPs GI.3, GII.4, GII.6, and GII.17. Of the 12 mAbs isolated, 9 mAbs blocked at least 1 of VLPs tested from binding to PGM with $EC_{50}$ values less than 1 μM.

Prior to these studies, the inventors expected that cross-reactive and neutralizing human mAbs would bind predominantly to the P subdomain of the circulating strains, similar to the findings for cross-reactive murine Abs (Crawford et al., 2015). The P domain has more surface exposure on a live virion than the S domain and should, therefore, be more accessible than the S domain. Both previously characterized mAbs, the human IgA 512 and the mouse IgG 10E9, target regions adjacent or at the HBGA-binding site on the P2 subdomain thereby directly preventing the binding of glycans (Shanker et al., 2016; Koromyslova et al., 2019). Here, the inventors describe a crystal structure of a human derived neutralizing antibody in complex with a GII.4 strain of NoV. The crystal structure of Nano-85, an alpaca derived nanobody, which is much smaller in molecular size when compared to a Fab, in complex with the GII.4 P domain was also recently reported (Koromyslova et al., 2015). Nano-85 binds toward the proximal end of the P domain dimer, which in the context of the capsid would be closer to the S and P domain interface. The epitope recognized by this nanobody which consists of W520, N522, and T526 is entirely distinct from that recognized by NORO-320. Based on negative-stain images of VLPs in complex with this nanobody it is suggested that the binding disrupts particle assembly.

It is indeed intriguing that even though NORO-320 does not directly bind in close proximity to the receptor binding domain it still inhibits GII.4 VLPs from binding to glycans in vitro and inhibits viral replication of GII.4 Sydney 2012 virus (Alvarado et al., 2018). The blockade studies using IgG and Fab recombinant variants, as well as the originally isolated antibody that was a dimeric IgA molecule, show that the molecular size of the mAb influenced the potency of neutralization (FIG. 15). Blocking potential increased with the increase in molecular size of the NORO-320 variant tested. Therefore, blockade potential is a result of NORO-320 sterically blocking GII.4 VLPs from binding to glycans in vitro. Modeling of the Fab binding to the P domain in the context of the capsid using the only available X-ray structure of the GI.1 indicates that constant domain of the Fab clashes with the neighboring VP1 subunits potentially affecting the particle assembly. But the inventors' observation that Fab alone does not block the HBGA binding suggest that Fab binding does not affect capsid structure, and it is possible that the orientation of the constant domain in the context of the capsid is slightly altered to avoid clashes. However, the additional Fc region projecting out from the Fab, as in the context of IgA or IgG, may sterically hinder the glycan binding sites in the neighboring VP1 subunits. Thus, this study potentially identifies a novel mechanism of neutralization for GII.4 Sydney 2012 NoV. The amino acids critical for the interaction between the GII.4 P domain and NORO-320 also are conserved among GII.3, GII.6 and GII.17 strains, which suggests that they are neutralized similarly. It is also possible the bound NORO-320 IgG or the IgA affecting the particle integrity leading to disassembly is an additional factor contributing to neutralization.

These results suggest that even though there is a high degree of sequence and antigenic diversity in the capsid protein VP1 among circulating strains of human NoVs, common protective antigenic sites exist among these strains. Recognition of the P2 subdomain and the most conserved S domain of VP1 by human mAbs could be the molecular basis for broad cross-reactive neutralization. The novel neutralizing NoV epitope identified also informs us about a critical antigenic GII site that could later be used in the reformulation of broadly protective NoV vaccine candidates. These human mAbs also could be directly used as a prophylactic, a therapeutic, or a reagent for diagnosis.

TABLE 1

NUCLEOTIDE SEQUENCES FOR ANTIBODY VARIABLE REGIONS

| Clone | Variable Sequence Region | SEQ ID NO: |
|---|---|---|
| NORO-115 Heavy | caggtgcagctggtggagtctgggggaggcttggtcaagcctggggggtccctgagactctcctgtac agcctctggaatcaccatcagtggctactacatgagttggatccgccaggctccagggaagggactgg aatggattgtatacattaatacaagtggtagaaccatatactacgcagactctgtgaagggccggttct ccgtctccagggacaacgccaaggagtcgctgtatttgcaaatggacagcctgacggtcgatgacacg ggcatatattattgtgcgagagatcgattaccagcatctggttcccactggttccacccctggggccag ggaaccctggtcaccgtctcctcag | 1 |
| NORO-115 light | gacatcgtgatgacccagtctccagactccctggctgtgtctctgggcgggagggccaccatcaactgc aagtccagccagagtgttttatacacctccgacaataagaactacttagcctggtaccagcagcaacc aggacagcctcctaagctgctcatttcctgggcttctactcgggaatccggggtccctgaccgattcagt ggcagcgggtctgggacagatttcactctcaccatcagcaacctgcaggctgaagatgtggcagtttat tactgtcagcagtattataatagtcctctcgctttcggcggagggaccaaggtggagatcaaa | 2 |
| NORO-123 Heavy | caggtgcagctggtggagtctgggggaggcgtggtccagcctgggaggtccctgagactctcctgttc aacctctggattcaccttcagtcaatatcctatgcactgggtccgccaggctccaggcaaggggctgga gtgggtggcacttatatcctatgatggaatgaataaatactacgcagactccgtgagggccgattcac catctccagagacaattccgagaacacgcagtatctgcaaatgaacagcctgagaggtgacgacacg gctgtctattattgtgcgagagtcacgggcgattgtactggtaatagatgctcatattgggcatactact actacggtctggacgtctggggccaagggaccctggtcaccgtctcctca | 3 |

TABLE 1-continued

NUCLEOTIDE SEQUENCES FOR ANTIBODY VARIABLE REGIONS

| Clone | Variable Sequence Region | SEQ ID NO: |
|---|---|---|
| NORO-123 light | cagtctgccctgactcagcctcccctccgcgtccgggtctcctggacagtcagtcaccatctcctgcactg gaaccagtagtgacgttggtggttataagtatgtctcctggtaccaacagcacccaggcaaagccccc aaaactcatgatttatgaggtcactaggcggccctcaggggtccctgatcgcttctctggctccaagtctg gcaacacggccttcctgaccgtctctgggctccaggctgaggatgaggctgattattactgcggctcat atgcaggcagcaccacttccgggtatgtcttcggaactgggaccaaggtcatcgtccta | 4 |
| NORO-202A.1 Heavy | caggtgcagttggtgcagtctggggctgaggtgaagaagcctggggcctcagtgaaggtctcctgcaa ggcttctgaatacacctttaccggctactattttgcagtgggtgcgacaggcccctggacatgggcttga atggatgggatggatcaatcccagtggtggcacaaagtattcacagaagtttcagggcagggtcacca tgaccagggacacgtccatcactactgtctacatggaactgagcagactgagatctgacgacacggcc gtctattactgtgcgagagaccttcttaggaactggggtgatcatgatgcttttgatgtctggggccagg ggacaatggtcaccgtctcctcag | 5 |
| NORO-202A.1 light | cagtctgtgctgactcagccaccctcagcgtctgagaccccgggcaggggtcaccatctcttgttctg gaagcagctccaacatcggaagtaattttgtatgctggtaccagcaggtcccaggaacggccccaaa ctcctcatctataagaataatcagcggccctcaggggtccctgaccgattctctggctccaagtctggca cctcagcccctggccatcagtgggctccggtccgaggatgaggctgattattactgttcagcatggg atgacagcctgagtggtccggtattcggcggagggaccaagctgaccgtcctag | 6 |
| NORO-250B Heavy | caggtgcagctggtggagtctgggggaggcttggtcaagcctggagggtccctgacactctcctgtgc agcctctggattcaccttcagtgactactacatgaactggatccgccaggctccaggaagagactgg agtgggtttcatacattagtggtattatgagttccacaaactacgcagactctgtgaagggccgattca ccatctccagagacaccgccaagaagtcagtgtatctgcaaatgaacagcctgagagccgaggatac ggctgtgtattactgtgcgagagcaacctcacaggagctacctcttactactttgactcctggggcca gggaaccctggtcaccgtctcctca | 7 |
| NORO-250B Light | cagtctgtgctgacgcagccgccctcagtgtctggggcccagggcagagggtcaccatctcctgcact gggagcagctccaacatcggggcagattatgatgttcactggtaccaacaacttccaggagcagccc cagactcctcatctatgctgacatcaatcggccctcagggtccctgatcgattctctggctccaagtct ggcacctcagcctcctggccatcactgggctccaggctgaggatgaggctgattattactgccaatcc tatgacagaagcgtgagtggttcggcggtgttcggcggagggaccaaggtgaccgtccta | 8 |
| NORO-251A Heavy | caggtgcagctggtggagtctgggggaggcgtggtccagcctggggaggtccctgagactctcctgtgc agcctctggattcaccttcaggagctatggcattcactgggtccgccaggctccaggcaaggggctgg agtgggtggcacttatatcatatgatggaagtagtaaatactatgcagactcagtgaagggccgattc accatctccagagacaattccaagaacacgttgtatctgcaaatgaacagcctgagaagtgaggaca cggctgtgtattactgtgcgaaagtgaggttgacaagttatagcattggctggttttcctttgactactgg ggccagggtaccctggtcaccgtctcctca | 9 |
| NORO-251A Light | caggtgcagctggtggagtctgggggaggcgtggtccaggctggggaggtccctgagactctcctgtgc agcctctggattcaccttcaggagctatggcattcactgggtccgccaggctccaggcaaggggctgg agtgggtggcacttatatcatatgatggaagtagtaaatactatgcagactcagtgaagggccgattc accatctccagagacaattccaagaacacgttgtatctgcaaatgaacagcctgagaagtgaggaca cggctgtgtattactgtgcgaaagtgaggttgacaagttatagcattggctggttttcctttgactactgg ggccagggtaccctggtcaccgtctcctca | 10 |
| NORO-256A Heavy | caggtgcagctggtggagtctgggggaggcgtggtccaggctggggaggtccctgagactctcctgtgc agcctctggattcaccttcagaagttatggcatgcactgggtccgccaggctccaggcaaggggctgg agtgggtggcaattatatcatatgatggaagtagtaaatattatgcagactccgtgaagggccgattca ccatctccagagacaattccaagaacacgttgtatctgcaaatgaacagcctgagagttgaggacacg gctctatattactgtgcgaaagattttttacgtgtatacagttatggttggcactcttttgatatttgggc ctagggaccctggtcaccgtctcctca | 11 |
| NORO-256A Light | cagtctgtgttgacgcagccgcctcagtgtctgcggccccaggacagagggtcaccatctcctgctct ggaagcagctccaacattgggacttattatgtctcctggtaccagcatctcccaggaacagcccccaaa ctcctcatttatgacaatgataagcgaccctcaggggattcctgaccgattctctgcctccaagtctggca cgtcagccaccctggacatcgccggactccaaactggggacgaggccgattattactgcggaacatgg gatctcagcctgactgctggctgggtgttcggcggagggaccaagttgaccgtccta | 12 |
| NORO-278 Heavy | caggtgcagctggtggagtctgggggaggcgtggtccaggctggggaggtccctgagactctcctgtgc agcctctggattcaccttcagtagctatggcatgcactgggtccgccaggctccaggcaaggggctgg agtgggtggcagttatatcatatgatggaagtaataaatactatgcagactccgtgaagggccgattc accatctccagagacaattccaagaacacgctgtatctgcaaatgaacagcctgagagctgaggaca cggctgtgtattactgtgcgaaagttaccattatagcagcagctgatttgcttgactactggggccaggg aaccctggtcaccgtctcctca | 13 |
| NORO-278 light | cagtctgtgctgacgcagccgccctcagtgtctggggcccagggcagagggtcaccatctcctgcact gggagcagctccaacatcggggcaggttatgatgtacactggtaccagcagcttccaggaacagccc ccaaactcctcatctatggtaacagcaatcggccctcaggggtccctgaccgattctctggctccaagt ctggcacctcagcctcctggccatcactgggctccaggctgaggatgaggctgattattactgccagt cctatgacagcagcctgagtggtccggtggtattcggcggagggaccaagctgaccgtccta | 14 |
| NORO-279A Heavy | caggtgcagctggtggagtctgggggaggcgtggtccaggctggggaggtccctgagactctcctgcgc agcctctggattcaccttcacaaaatatggcatgcactgggtccgccaggctccaggcaaggggctgg agtgggtggcttttatagcatatgatggaagtgttaaatattatgagactccgcgaagggccgattcg | 15 |

TABLE 1-continued

NUCLEOTIDE SEQUENCES FOR ANTIBODY VARIABLE REGIONS

| Clone | Variable Sequence Region | SEQ ID NO: |
|---|---|---|
| | ccatttccagagacaatcccaagaatacagtatatctgcaaatgaacagcctgagagcagaagacac<br>ggctgtatattattgtgcgaaagtggagatacactattattcgaatagtctcttaggtatggacgtctgg<br>ggccaagggaccctggtcaccgtctcctca | |
| NORO-<br>279A<br>Light | cagtctgtgctgactcagccaccctcagcgtctgggaccccgggcagagggtcaccatctcttgttctg<br>gaggcaactccaacatcggaattagttatgtgtactggtaccagcatctcccaggaacggcccccaaa<br>ctcctcatatctaaaaataatctgcggccctcaggggtccctgaccgattctctgctccaagtctggca<br>cttcagcctccctggccatcagtggactccggtccgaggatgaggctgaatattactgtgcaacattgg<br>atatcaatatgacctgggtattcggcggagggaccaagctgaccgtccta | 16 |
| NORO-<br>296A<br>Heavy | caggtgcagctggtggagtctgggggaggcttggtcaagcctggagggtccctgagactctcctgtgc<br>agcctctggattcaccttcagtgagtactacatgagctgggtccgccaggctccagggaaggcgctgg<br>agtgggtttcatacattactagtagtttcagttccacaagctatgcagactctgtgaaggggccgattcgt<br>catctccagagacaacgccaagaactcactgtatctacaaatgaacagcctgagagtcgaggacacg<br>gccgtgtattactgtgcgagatatggcgcggagtatggttcgcggagtttctacttcctggactgggcc<br>agggcaccctggtcaccgtctcctca | 17 |
| NORO-<br>296A<br>Light | cagtctgtgctgacgcagccgccctcagtgtctggggcccagagcagagggtcaccatctcctgcact<br>gggagcagctccaacatcggggcaggttatgatgtacactggtaccaggtgcttccaggaatagcccc<br>caaactcctcatctacgataacaacaagcggccctcaggggtccctgaccgattctctggctccaagtc<br>tggcacctcagcctccctggccatcactgggctccaggctgaggatgaggctgattattactgccagtc<br>ctatgacagcaggctgagtagcaatgtggtattcggcggagggaccaaactgaccgtcctg | 18 |
| NORO-<br>303<br>Heavy | caggtgcagctggtggagtctgggggaggcgtggtccagcctggggaggtccctgagactctcctgtgc<br>agcctctggattcatcttcagtagctatgctatgcactgggtccgccaggctccaggcaaggggctaga<br>gtgggtggcagttatgtcatatgatggaaataataaatactacgcagactccgtgaagggccgattca<br>ccatctccagagacaattccaagaacacgctgtttctgcaaatgaacagcctgagacctgaggacacg<br>gccgtgtattattgtgcgagagattgtcgagtcggtgggtattcacctacggtatggacgtctggggc<br>caagggaccctggtcaccgtctcctca | 19 |
| NORO-<br>303<br>Light | cagtctgccctgactcagcctccctccgcgtccgggtctcctggacagtcagtcaccatctcctgcactg<br>gaaccagcagtgacgttggtggtttataactatgtctcctggtaccaacagcacccaggcaaagccccc<br>aaactcatgatgtatgagatcagtaagcggccctcaggggtccctgatcgcttctctggctccaagtctg<br>gcaacacggcctccctgaccgtctctgggctccaggctgaggatgaggctgattattactgcagctcat<br>atgcaggcacctacaactgtgtggtattcggcggagggaccaagctgaccgtccta | 20 |
| NORO-<br>310A<br>Heavy | gaggtgcagctggtggagtctgggggaggcttggtccggcctggggagtccctgagactctcctgtgta<br>gcctctggattcagcgtcagtgacaactacatgagctgggtccgccaggctccagggaagggactgca<br>gtgggtctccgttatttatagcggtggtactacattctacacagactccgtgaagggcagattcaccatc<br>tccagagacaagtccaagaacacgctgtttcttcaaatgaacagcctgagagccgaggacacggctg<br>tgtatttctgtacgcgagatccatcgcaatactatgatagtcgtggtcattactaccagactttcactccc<br>tcctttgactcctggggccagggaaccctggtcaccgtctcctca | 21 |
| NORO-<br>310A<br>Light | gacatccagatgacccagtctccatctgtcatgtctgcatctgtaggagacagagtcaccatcacttgtc<br>gggcgagtcaggacattagcgattatttagcctggtttcagcagaaaccagggaaagtccctaagcgc<br>ctgatctatgctgcatccagtttgcaaaatggggtcccatcaaggttcagcggcagtggatctgggaca<br>gaattcactctcacaatcagcagcctgcagcctgaagattttgcaacttattactgtctacagcatgata<br>cttaccctctcactttcggcggagggaccaaggtggagatcaaa | 22 |
| NORO-<br>312A<br>Heavy | caggtgcagctggtggagtctggggggaggcttggtcaagcctggagagtccctgagactctcctgtgc<br>agcctctggattcaccttcagtgactcctacatgagctggatccgccaggctccagggaagggactgg<br>agtgggttgcatacattagtggtatcatgagttccacaaactacgcagattctgtgaaaggccgattca<br>ccatctccagagacaacggcaagaactcagtgtatctgcaaatgaacaacctgagagccgaggacac<br>ggctgtgtactactgtgcaagagatgcccaatattgcagtggcggtaggtgctacttggtatttgactac<br>tggggccagggaaccctggtcaccgtctcctca | 23 |
| NORO-<br>312A<br>Light | cagtctgtgctgacgcagccgccctcagtgtctggggcccaggacagagggtcaccatctcttgcact<br>gggagcagctccaacatcggggcaggttatgaagtacactggtaccagcaacttccaggagcagccc<br>ccaaactcatcatctatggtaacaacaatcggccctcaggggtccctgaccgattctctggctccaagt<br>ctggcacctcagcctccctggccatcactgggctccaggctgacgatgaggctgattattactgccagt<br>cttatgacaacaggctaagggtattcggcggggggaccaagctgaccgtccta | 24 |
| NORO-<br>313.1<br>Heavy | caggtgcagctggtggagtctgggggaggcttggtcaagcctggagggtccctgagactctcctgtgc<br>agcctctggattcaccttcagtgacttctacatgagctggatccgccaggctccagggaaggggctgga<br>gtgggttgggtacattagctctattgctggtgccacaaattacgcagactctgtgaagggccgattcac<br>catctccagagacagctccaagaggtcactgtatctgcaaatgaacagcctgagagtcgaggacacg<br>gctgtatactactgtgcgagaatggggcgcttagagctggagcgacggcccattattactacccttttg<br>gacgtctggggccaagggaccctggtcaccgtctcctca | 25 |
| NORO-<br>313.1<br>Light | gatattgtgatgacccagtctccactctccctgcccgtcacccctggagagccggcctccatctcctgca<br>ggtctagtcagagcctcctgcatagtaatggatacaactatttggattggtacttgcagaagccaggc<br>agtctccacagctcctgatctttttgggttctaatcggcctccggggtccctgacaggttcagtggcag<br>tggatcaggcacagattttacactgaaaatcagcagagtggaggctgaggatgttggggtttattactg<br>catgcaagctctacaaactcggacttttggccaggggaccaagctggagatcaaa | 26 |

TABLE 1-continued

NUCLEOTIDE SEQUENCES FOR ANTIBODY VARIABLE REGIONS

| Clone | Variable Sequence Region | SEQ ID NO: |
|---|---|---|
| NORO-315B Heavy | caggtgcagctggtggagtctgggggaggcttggtcaagcctggagggtccctgagactctcctgtgtg gcctctggattcaccttcagcgactactacatgacctggttccgccagactccagggaggggctggag tggctttcatacattagtgctatcggaggttacacagaatacgcagactctgtgaagagccgattcatc atctctagagacaacggcaagaaatcactgtatcttcaaatgaacagcctcagagccgaggactccg gtgtctattactgtgcgagagaagattgtcatggtactagttgctactcggcgactggggccagggaa ccctggtcaccgtctcctca | 27 |
| NORO-315B Light | cagtctgtgctgacgcagccgccctcagtgtctggggccccagggcagagggtcaccatctcctgcact gggagcagctccaacatcggggcaggttatgatgtacactggtaccagcagcttccaggaacagccc ccaaactcctcatctatcataacaccaatcggccctcgggggtccctgaccgattctctggctccaagtc tggcacctcagcctacctgaccatcactgggctccaggctgaggatgaggctgattattactgccagtc atatgacagaagcctcagtaaatcgagggtgttcagcggagggaccaagctgaccgtccta | 28 |
| NORO-317 Heavy | caggtgcagctggtggagtctgggggaggcttggtcaagcctggagggtccctgagactctcctgtgta gcatctggattcaccttcagtgactactacatcagctgggtccgccaggctccagggaaggggctgga gtgggtttcatacattagtgctattaatagttatacaaactatgcagactctgtgagggccgattcacc gtctccagagacaacgccaagaagtcagtcttttttgcaaatgaatagcctgagagtcgacgacacggc tgtgtattattgtgcgagagatgtcggcggctcggttcggtatagcagcaactcgaacaaaaaatccta caactacttcgacccctggggccagggaaccctggtcaccgtctcctca | 29 |
| NORO-317 Light | tcctatgagctgacacagccaccctcggtgtcagtgtcccaggacagacggccacgatcacctgctc gggagatgttttgtcaaaggagtttgcttattggtaccagcagaagccaggccaggcccctgtgttggt gatatataaagacaatgagaggccctcagggatacctgagcgattctctggctccacctcagggacaa cagtcacgttgaccatcagtggagtcctggcagaagacgaggctcactattattgtcaatcagtagac accaggggcacttataaagtgttcggcggagggaccaagctgaccgtccta | 30 |
| NORO-320 Heavy | caggtgcagctggtgcagtctgggcctgaggtgaagaagcctgggtcctcggtgaaggtctcctgcaa ggcttctggaggcaccgtcagcagctatgctatcagctgggtgcgacaggcccctggacaagggcttg agtggatgggagggatcatcccatctttgataacaaactacgcacagaaattccagggcagatt acgattaccgcggacgaatccacgggcacaagcgacatggaactgagcagcctagatctgaggaca cggccgtgtattactgtgcgagagatcgcgtcccgtcttattctccttcgcggaggttttccactaagggg ggcgatgtggggaaaatacggtatggacgtctgggggccaagggaccctggtcaccgtctcctca | 31 |
| NORO-320 Light | gatattgtgatgactcagtctccactctccctgcccgtcacccctggagagccggcctccatctcctgna ggtctagtcagagcctcctgcatagtaatggatacaactatttggattggtacctgcagaagccagggc agtctccacagctcctgatctatttgggttctaatcgggcctccgggtccctgacaggttcagtggcag tggatcaggcacagattttacactgaaaatcagcaaagtggaggctgaggatgttggggtttattactg catgcaagctctacaaactcctcggacgttcggccaagggaccaaggtggaaatcaaa | 32 |
| NORO-329A Heavy | caggtgcagctggtggagtctgggggaggcttggtcaagcctggagggtccctgagactctcctgtgc agcctctggattcaccttcagtgactactacatgagctggatccgccaggctccagggaaggggctgg agtggatttcatatattagcagtagttttggttccacagactacgcaggctctatgaagggccgagatt cactctccagagacaacgccaagaattcactgtatctgcaaatgaacagcctgagagccgaggacacg gctgtgtattactgtgcgagatacaattactatggttcggggagtttcgtctttgactactggggccagg ggaccctggtcaccgtctcctca | 33 |
| NORO-329A Light | cagtctgtggcgactcagccaccctcagcgtctgggaccccgggcagagggtcaccatctcttgttct gggagcagctccaacatcggaagtaatactgtaagctggtaccagcaactcccaggaacggccccca aactcctcatttatagtaatgatcagcggccctcaggggtccctggccgattctctggctccaagtctgg cacctcagcctcctggccatcagtgggctccagtctgaggatgagggtgattattcctgtgcagcatg ggatgacagcctgaatggttgggtgttcggcggagggaccaagctgaccgtccta | 34 |
| NORO-118 Heavy | caggtgcagctggtggagtctggggggaggcgtggtccagcctggggggtccctgagactctcctgtac agcgtctggattcaccttcagtggtcatggcatgcactgggtccgccaggctccaggcaaggggctgg aatgggtgacatttatatcatatgatggaagtaataaattctatgcggactcagtgaagggccgattca tcatctccagagacaattccgagaacacgttgtttctgcagatgaacagcctgagaccggaagacacg ggagtctattggtgtgcgagagatggttacagaaatttggtcctcgttgggtggtacttcgatctctggg gccgtggcaccctggtcaccgtctcctca | 207 |
| NORO-118 Light | Not available | 208 |
| NORO-232 Heavy | Not available | 209 |
| NORO-232 Light | gagattgtgctgacccaaagtcccgctacacttagcctgtctcctggagattctgctacactgagctgta gagcttctcaggctgtgtctaccacctatctggcctggtatcagcagacaagaggacaagcccctaga ctgctgattcacggcacctacacaagagctatcggcattcctgacaagttttctggaaccggctctggc accgattttaccctgaccatctctggacttgccctgaggattttgctgtgtactactgccagcagtacag ctctagccccttacacctttggacagggcaccaagatcgagatcacc | 210 |

TABLE 1-continued

NUCLEOTIDE SEQUENCES FOR ANTIBODY VARIABLE REGIONS

| Clone | Variable Sequence Region | SEQ ID NO: |
|---|---|---|
| NORO-246A Heavy | Not available | 211 |
| NORO-246A Light | agcaacgaactgacacaagccccttctgtgtctgtgtctcctggacaaacagccagaatcacctgcttc<br>ggagatgctctggctaaccagtacagctactggtaccagagaaaaccaggacaggctccagtgctgg<br>tgatctacaaggacagcgagagacctagcggaattcctcagagattttctgcctccaatagcggcacc<br>acagtgacactgaccatcacaggagtgcaggctgaagatgaagccgattacttctgtcagagcgccg<br>attctacaggcatctacaaggtgtttggcggcggcacaaaactgacagttctg | 212 |
| NORO-263 Heavy | caggtgcagctggtggagtctgggggaggcttggtcaagcctggagggtccctgagactctcctgtgc<br>agcctctggattcaccttgagtgactactacatgagttggatccgccaggctccagggaaggggctgg<br>agtgggttgcatacatcagtagtagtcatacttccacatactacagagactctgtgaaggggccgattca<br>ccatctccagggacagcgccaagaagtcactgtatctgcaaatgaacagcctgagagtcgaggacac<br>ggctatatattactgtgcgagagattgggtaggtggtaggagcgcgtatagtgaccactggggccagg<br>gaaccctggtcaccgtctcctca | 213 |
| NORO-263 Light | tcctatgagctgacacagccaccctcggtgtcagtgtcccaggacaaacggccaggatcacctgctct<br>ggagatgcgttgccaagaagacctgctttttggtatcagcagaagtcaggccaggcccctgtgttggtc<br>atgtatgacgacagcaaacgaccctccgggatccctgagagattctctggctccagctcagggacagt<br>ggcccactgactattagtggggcccaggtggaggatgaagctgactaccactgttactcaacagaca<br>gcagtggtaaggaaagagttttcggcggagggaccaagctgaccgtcctc | 214 |
| NORO-273A Heavy | caggtccagctggtgcagtctggggctgaggtgaagaagcctggggcctcagtgaaaatttcctgcaa<br>ggcttctggatacgacttcactagttttcctatgcattgggtgcgcctggggcccggacaaaggcttgag<br>tggatgggatggatcagcgctgccaatggtaacacaaaatattcacagaagttccaggacagattcac<br>cattaccagggacacatccgcgagtatagtccacatggagttgagtagcctgagatctgaagacacgg<br>ctgtatactactgtgcgagggggggtatagtagtgggctgtacagatattccaactactactacggta<br>tgaccgtctggggccaagggaccctggtcaccgtctcctca | 215 |
| NORO-273A Light | gatattgtgatgacccagactccactctctctgtccgtcacccctggacagccggcctccatctcctgca<br>agtctagtgagagcctcctgcataatgatcgaaaaacctatttgttttggtacctgcagaagccaggcc<br>agcctccacaactcctgatcttcaagtctccaaccggttctctggagtgccagataggttcagtggcag<br>cggatcagggacagacttcacactgagaatcagccgtgtggaggctgaggatgttgggattttattact<br>gcttgcaaactacacagcttccgctcactttcggcggagggaccaaggtggagatcaaa | 216 |
| NORO-316 Heavy | Not available | 217 |
| NORO-316 Light | Not available | 218 |
| NORO-318 Heavy | Not available | 219 |
| NORO-318 Light | gatattgtgatgactcagtctccactctccctgcccgtcacccctggagagccggcctccatctcctgca<br>ggtctagtcagagcctccttcacagtgatggactcaactatttggattggtacctgctgaagccagggc<br>agcctccacagctcctgatctatttggcttctaatcgggcctccggggcccctgacaggttcagtggcag<br>tggatcaggcacagattttacactgacaatcagcagagtggaggctgaggatgttggaatttattactg<br>catggaagctctacaaactcctcccactttcggcggagggaccaaggtggagatcaaa | 220 |
| NORO-327A Heavy | Not available | 221 |
| NORO-327A Light | cagtctgtgctgacgcagtcgccctcagtgtctggggcccagggcagagggtcaccatctcctgcact<br>gggaccagctccaacatcggggcaggttatgatgtacactggtatcagcagtttcctggaacagcccc<br>caaactcctcatctctcataacaccaatcggccctcaggggtccctgaccgattctctggctccaagtct<br>ggcacctcagcctccctggccatcactgggctccaggctgaggatgaggctgattattactgccagtcc<br>tttgacagcagcctgcgggggttccagggtgttcggcggagggaccaagctgaccgtccta | 222 |
| NORO-156.3 Heavy | caggtgcagctacagcagtggggcgcaggactgttgaagccttcggagaccctgtccctcacctgcgc<br>tgtctatggtgggtccttcagtggttactactggagctggatccgccagcccccagggaaggggctgga<br>gtggattgggaaatcaatcatagtggaagcaccaactacaacccgtccctcaagagtcgagtcacc<br>atatcagtagacacgtccaagaaccagttctccctgaagctgagctctgtgaccgccgcggacacggc<br>tgtgtattactgtgcgagaggcttaatggacgtctggggcaagggaccctggtcaccgtctcctca | 288 |
| NORO-156.3 Light | gccatccggatgacccagtctccatcctcattctctgcatctacaggagacagagtcaccatcacttgtcgggcga<br>gtcagggtattagcagttatttagcctggtatcagcaaaaaccagggaaagcccctaagctcctgatctatgctg<br>catccactttgcaaagtggggtcccatcaaggttcagcggcagtggatctgggacagatttcactctcaccatca<br>gctgcctgcagtctgaagattttgcaacttattactgtcaacagtattatagttaccctcgcacttttggccagggg<br>accaagctggagatcaaac | 289 |

TABLE 1-continued

NUCLEOTIDE SEQUENCES FOR ANTIBODY VARIABLE REGIONS

| Clone | Variable Sequence Region | SEQ ID NO: |
|---|---|---|
| NORO-168.2 Heavy | caggtgcagctggtggagtctgggggaggcgtggtccagcctggggaggtccctgagactctcctgtgcagcctct ggattcacccttcagtagctatgctatgcactgggtccgccaggctccaggcaaggggctagagtgggtggcagtt atatcatatgatggaagtaataaatactacgcagactccgtgaagggccgattcaccatctccagagacaattcc aagaacacgctgtatctgcaaatgaacagcctgagagctgaggacacggctgtgtattactgtgcgaggtcagt tattgggtactactactacggtatggacgtctggggccaagggaccctggtcaccgtctcctca | 290 |
| NORO-168.2 Light | cagcctgtgctgactcagccaccttctgcatcagcctccctgggagcctcggtcacactcacctgcaccctgagca gcggctacagtaattataaagtggactggtaccagcagagaccagggaagggcccccggtttgtgatgcgagtg ggcactggtgggattgtgggatccaaggggatggcatccctgatcgcttctcagtcttgggctcaggcctgaat cggtacctgaccatcaagaacatccaggaagaggatgagagtgactaccactgtggggcagaccatggcagtg ggatcctattcggcggagggaccaagctgaccgtcctag | 291 |
| NORO-178.6 Heavy | caggtgcagctggtggagtctgggggaggcgtggtccagcctggggggtccctgagactctcctgtgcagcctct ggattcacttttcagtacctacggcatgaactgggtccgccaggctccaggcaggggactggagtgggtggcaga tatatcatatgatggaagtaatagtcgctatgcagactccgtgaagggccgattcaccatctccagagacaattc caagaacacgctatctctgcagatgaacgcctgagaactgaggacggctgtgtattattgtgcgaaagatt ggtatttggcaatggctggtgcagcttttgactcctggggccgggaaccctggtcaccgtctcctcag | 292 |
| NORO-178.6 Light | tcttctgagctgactcaggaccctgttgtgtctgtggccttgggacagacagtcaggatcacatgccaaggagac agcctcacaacctttatgcaagctggttccagcagaagccaggacaggcccctgcacttgtcctgtatggtaac gacaaccggccctcaggatcccagaccgattctctggctccaggtcaggaaacacagcttccttgaccatcact ggggctcaggcggaagatgaggctgactattactgtaactcccgggacagcagtggtaaaccctcattcggcgg agggaccaagctgaccgtcctaa | 293 |
| NORO-279A Heavy | caggtgcagctggtggagtctgggggaggcgtggtccagcctggggaggtccctgagactctcctgcgcagcctct ggattcaccttcacaaaatatggcatgcactgggtccgccaggctccaggcaaggggctggagtgggtggctttt atagcatatgatggaagtgttaaatattatggagactccgcgaagggccgattcgccatttccagagacaatccc aagaatacagtatctgcaaatgaacgcctgagagcagaacacggctgtatattattgtgcgaaagtgga gatacactattattcgaatagtctcttaggtatggacgtctggggccaagggaccctggtcaccgtctcctca | 294 |
| NORO-279A Light | cagtctgtgctgactcagccaccctcagcgtctgggaccccgggcagagggtcaccatctcttgttctggaggc aactccaacatcggaattagttatgtgtactggtaccagcagctcccaggaacggccccaaactcctcatatcta aaaataatctgcggccctcaggggtccctgaccgattctctgcctccaagtctggcacttcagcctccctggccat cagtggactccgtccgaggatgaggctgaatattactgtgcaacattggatatcaatatgacctgggtattcgg cggagggaccaagctgaccgtccta | 295 |
| NORO-323A Heavy | caggtgcagctggtggagtctgggggaggcgtggtccagcctggggaggtccctgcgactctcctgtgcagcctct ggattcaccttcagtggctcttcactgcactgggtccgccaggctccaggcaaggggctggagtgggtggcagct atatcatatgatggaactaatacatactatgcagactccgtgaagggccgattcacccctctcagagacaattcc aagaacacgctgtatctgcagatgaacagcctgagagctgaggacacggctgtgtattactgtgcgaaaccagt cctttccccctttgactactggggccagggaaccctggtcaccgtctcctcag | 296 |
| NORO-323A Light | cagtctgccctgactcagcctgcctccgtgtctgggtctcctggacagtcgatcaccatctcctgcactggaacca gcagtgacgttggtggttataattatgtttcctggtaccaacaacacccaggcaaagcccccaaactcttgatttta tgaggtcagtaatcggccctcaggggtttctagacgcttctctggctccaagtctggcaacacggcctccctgacc atctctggctccaggctgaggacgaggctgattattactgctgctcatataccagcagcagcactgaggtgttc ggcggagggaccaagctgaccgtcctag | 297 |

TABLE 2

PROTEIN SEQUENCES FOR ANTIBODY VARIABLE REGIONS

| Clone | Variable Sequence | SEQ ID NO. |
|---|---|---|
| NORO-115 Heavy | QVQLVESGGGLVKPGGSLRLSCTASGITISGYYMSWIRQAPGKGLEWIVYINTSG RTIYYADSVKGRFSVSRDNAKESLYLQMDSLTVDDTGIYYCARDRLPASGSHWFH PWGQGTLVTVSS | 35 |
| NORO-115 light | DIVMTQSPDSLAVSLGGRATINCKSSQSVLYTSDNKNYLAWYQQQPGQPPKLLIS WASTRESGVPDRFSGSGSGTDFTLTISNLQAEDVAVYYCQQYYNSPLAFGGGTK VEIK | 36 |
| NORO-123 Heavy | QVQLVESGGGVVQPGRSLRLSCSTSGFTFSQYPMHWVRQAPGKGLEWVALISY DGMNKYYADSVRGRFTISRDNSENTQYLQMNSLRGDDTAVYYCARVTGDCTGN RCSYWAYYYYGLDVWGQGTLVTVSS | 37 |
| NORO-123 light | QSALTQPPSASGSPGQSVTISCTGTSSDVGGYKYVSWYQQHPGKAPKLMIYEVT RRPSGVPDRFSGSKSGNTAFLTVSGLQAEDEADYYCGSYAGSTTSGYVFGTGTKVI VL | 38 |

TABLE 2-continued

PROTEIN SEQUENCES FOR ANTIBODY VARIABLE REGIONS

| Clone | Variable Sequence | SEQ ID NO. |
|---|---|---|
| NORO-202A.1 Heavy | QVQLVQSGAEVKKPGASVKVSCKASEYTFTGYYLQWVRQAPGHGLEWMGWIN PSGGTKYSQKFQGRVTMTRDTSITTVYMELSRLRSDDTAVYYCARDLLRNWGDH DAFDVWGQGTMVTVSS | 39 |
| NORO-202A.1 light | QSVLTQPPSASETPGQGVTISCSGSSSNIGSNFVCWYQQVPGTAPKLLIYKNNQR PSGVPDRFSGSKSGTSASLAISGLRSEDEADYYCSAWDDSLSGPVFGGGTKLTVL | 40 |
| NORO-250B Heavy | QVQLVESGGGLVKPGGSLTLSCAASGFTFSDYYMNWIRQAPGKRLEWVSYISGI MSSTNYADSVKGRFTISRDTAKKSVYLQMNSLRAEDTAVYYCARATSQGATSYYF DSWGQGTLVTVSS | 41 |
| NORO-250B Light | QSVLTQPPSVSGAPGQRVTISCTGSSSNIGADYDVHWYQQLPGAAPRLLIYADIN RPSGVPDRFSGSKSGTSASLAITGLQAEDEADYYCQSYDRSVSGSAVFGGGTKVT VL | 42 |
| NORO-251A Heavy | QVQLVESGGGVVQPGRSLRLSCAASGFTFRSYGIHWVRQAPGKGLEWVALISYD GSSKYYADSVKGRFTISRDNSKNTLYLQMNSLRSEDTAVYYCAKVRLTSYSIGWFS FDYWGQGTLVTVSS | 43 |
| NORO-251A Light | QSVLTQPPSVSAAPGQKVTISCSGSSSNIANYYVSWYQQLPGRAPKLLIYDNNKR PSGIPDRISGSKSGTSATLGITGLQTGDEADYYCGTWDTSLSAWVFGGGTKLTVL | 44 |
| NORO-256A Heavy | QVQLVESGGGVVQAGRSLRLSCAASGFTFRSYGMHWVRQAPGKGLEWVAIISY DGGSKYYADSVKGRFTISRDNSKNTLYLQMNSLRVEDTALYYCAKDFLRVYSYGW HSFDIWGLGTLVTVSS | 45 |
| NORO-256A Light | QSVLTQPPSVSAAPGQRVTISCSGSSSNIGTYYVSWYQHLPGTAPKLLIYDNDKRP SGIPDRFSASKSGTSATLDIAGLQTGDEADYYCGTWDLSLTAGWVFGGGTKLTVL | 46 |
| NORO-278 Heavy | QVQLVESGGGVVQPGRSLRLSCAASGFTFSSYGMHWVRQAPGKGLEWVAVISY DGSNKYYADSVKGRFTISRDNSKNTLYLQMNSLRAEDTAVYYCAKVTIIAAADLLD YWGQGTLVTVSS | 47 |
| NORO-278 light | QSVLTQPPSVSGAPGQRVTISCTGSSSNIGAGYDVHWYQQLPGTAPKLLIYGNSN RPSGVPDRFSGSKSGTSASLAITGLQAEDEADYYCQSYDSSLSGPVVFGGGTKLTV L | 48 |
| NORO-279A Heavy | QVQLVESGGGVVQPGRSLRLSCAASGFTFTKYGMHWVRQAPGKGLEWVAFIAY DGSVKYYGDSAKGRFAISRDNPKNTVYLQMNSLRAEDTAVYYCAKVEIHYYSNSL LGMDVWGQGTLVTVSS | 49 |
| NORO-279A Light | QSVLTQPPSASGTPGQRVTISCSGGNSNIGISYVYWYQHLPGTAPKLLISKNNLRP SGVPDRFSASKSGTSASLAISGLRSEDEAEYYCATLDINMTWVFGGGTKLTVL | 50 |
| NORO-296A Heavy | QVQLVESGGGLVKPGGSLRLSCAASGFTFSEYYMSWVRQAPGKALEWVSYITSS FSSTSYADSVKGRFVISRDNAKNSLYLQMNSLRVEDTAVYYCARYGAEYGSRSFYF LDWGQGTLVTVSS | 51 |
| NORO-296A Light | QSVLTQPPSVSGAPEQRVTISCTGSSSNIGAGYDVHWYQVLPGIAPKLLIYDNNKR PSGVPDRFSGSKSGTSASLAITGLQAEDEADYYCQSYDSRLSSNVVFGGGTKLTVL | 52 |
| NORO-303 Heavy | QVQLVESGGGVVQPGRSLRLSCAASGFIFSSYAMHWVRQAPGKGLEWVAVMS YDGNNKYYADSVKGRFTISRDNSKNTLFLQMNSLRPEDTAVYYCARDCRVGWVF TYGMDVWGQGTLVTVSS | 53 |
| NORO-303 Light | QSALTQPPSASGSPGQSVTISCTGTSSDVGGYNYVSWYQQHPGKAPKLMMYEIS KRPSGVPIRFSGSKSGNTASLTVSGLQAEDEADYYCSSYAGTYNCVVFGGGTKLTV L | 54 |
| NORO-310A Heavy | EVQLVESGGGLVRPGESLRLSCVASGFSVSDNYMSWVRQAPGKGLQWVSVIYS GGTTFYTDSVKGRFTISRDKSKNTLFLQMNSLRAEDTAVYFCTRDPSQYYDSRGH YYQTFTPSFDSWGQGTLVTVSS | 55 |
| NORO-310A Light | DIQMTQSPSVMSASVGDRVTITCRASQDISDYLAWFQQKPGKVPKRLIYAASSLQ NGVPSRFSGSGSGTEFTLTISSLQPEDFATYYCLQHDTYPLTFGGGTKVEIK | 56 |
| NORO-312A Heavy | QVQLVESGGALVKPGESLRLSCAASGFTFSDSYMSWIRQAPGKGLEWVAYISGI MSSTNYADSVKGRFTISRDNGKNSVYLQMNNLRAEDTAVYYCARDAQYCSGGR CYLVFDYWGQGTLVTVSS | 57 |

TABLE 2-continued

PROTEIN SEQUENCES FOR ANTIBODY VARIABLE REGIONS

| Clone | Variable Sequence | SEQ ID NO. |
|---|---|---|
| NORO-312A Light | QSVLTQPPSVSGAPGQRVTISCTGSSSNIGAGYEVHWYQQLPGAAPKLIIYGNNN RPSGVPDRFSGSKSGTSASLAITGLQADDEADYYCQSYDNRLRVFGGGTKLTVL | 58 |
| NORO-313.1 Heavy | QVQLVESGGGLVKPGGSLRLSCAASGFTFSDFYMSWIRQAPGKGLEWVGYISSIA GATNYADSVKGRFTISRDSSKRSLYLQMNSLRVEDTAVYYCARMGRLELERRPHY YYPLDVWGQGTLVTVSS | 59 |
| NORO-313.1 Light | DIVMTQSPLSLPVTPGEPASISCRSSQSLLHSNGYNYLDWYLQKPGQSPQLLIFLG SNRASGVPDRFSGSGSGTDFTLKISRVEAEDVGVYYCMQALQTRTFGQGTKLEIK | 60 |
| NORO-3158 Heavy | QVQLVESGGGLVKPGGSLRLSCVASGFTFSDYYMTWFRQTPGRGLEWLSYISAIG GYTEYADSVKSRFIISRDNGKKSLYLQMNSLRAEDSGVYYCAREDCHGTSCYSGD WGQGTLVTVSS | 61 |
| NORO-3158 Light | QSVLTQPPSVSGAPGQRVTISCTGSSSNIGAGYDVHWYQQLPGTAPKLLIYHNTN RPSGVPDRFSGSKSGTSAYLTITGLQAEDEADYYCQSYDRSLSKSRVFSGGTKLTVL | 62 |
| NORO-317 Heavy | QVQLVESGGGLVKPGGSLRLSCVASGFTFSDYYISWVRQAPGKGLEWVSYISAIN SYTNYADSVRGRFTVSRDNAKKSVFLQMNSLRVDDTAVYYCARDVGGSVRYSSN SNKKSYNYFDPWGQGTLVTVSS | 63 |
| NORO-317 Light | SYELTQPPSVSVSPGQTATITCSGDVLSKEFAYWYQQKPGQAPVLVIYKDNERPS GIPERFSGSTSGTTVTLTISGVLAEDEAHYYCQSVDTRGTYKVFGGGTKLTVL | 64 |
| NORO-320 Heavy | QVQLVQSGPEVKKPGSSVKVSCKASGGTVSSYAISWVRQAPGQGLEWMGGIIPI FDTTNYAQKFQGRVTITADESTGTSDMELSSLRSEDTAVYYCARDRVPSYSPSRRF STKGAMWGKYGMDVWGQGTLVTVSS | 65 |
| NORO-320 Light | DIVMTQSPLSLPVTPGEPASISXRSSQSLLHSNGYNYLDWYLQKPGQSPQLLIYLG SNRASGVPDRFSGSGSGTDFTLKISKVEAEDVGVYYCMQALQTPRTFGQGTKVEI K | 66 |
| NORO-329A Heavy | QVQLVESGGGLVKPGGSLRLSCAASGFTFSDYYMSWIRQAPGKGLEWISYISSSF GSTDYAGSMKGRFTISRDNAKNSLYLQMNSLRAEDTAVYYCARYNYYGSGSFVF DYWGQGTLVTVSS | 67 |
| NORO-329A Light | QSVATQPPSASGTPGQRVTISCSGSSSNIGSNTVSWYQQLPGTAPKLLIYSNDQR PSGVPGRFSGSKSGTSASLAISGLQSEDEGDYSCAAWDDSLNGWVFGGGTKLTV L | 68 |
| NORO-118 Heavy | Not available | 223 |
| NORO-118 Light | Not available | 224 |
| NORO-232 Heavy | Not available | 225 |
| NORO-232 Light | EIVLTQSPATLSLSPGDSATLSCRASQAVSTTYLAWYQQTRGQAPRLLIHGTYTRAI GIPDKFSGTGSGTDFTLTISGLAPEDFAVYYCQQYSSSPYTFGQGTKIEIT | 226 |
| NORO-246A Heavy | Not available | 227 |
| NORO-246A Light | SNELTQAPSVSVSPGQTARITCFGDALANQYSYWYQRKPGQAPVLVIYKDSERPS GIPQRFSASNSGTTVTLTITGVQAEDEADYFCQSADSTGIYKVFGGGTKLTVL | 228 |
| NORO-263 Heavy | QVQLVESGGGLVKPGGSLRLSCAASGFTLSDYYMSWIRQAPGKGLEWVAYISSS HTSTYYRDSVKGRFTISRDSAKKSLYLQMNSLRVEDTAIYYCARDWVGGRSAYSD HWGQGTLVTVSS | 229 |

TABLE 2-continued

PROTEIN SEQUENCES FOR ANTIBODY VARIABLE REGIONS

| Clone | Variable Sequence | SEQ ID NO. |
|---|---|---|
| NORO-263 Light | SYELTQPPSVSVSPGQTARITCSGDALPRRPAFWYQQKSGQAPVLVMYDDSKRP SGIPERFSGSSSGTVATLTISGAQVEDEADYHCYSTDSSGKERVFGGGTKLTVL | 230 |
| NORO-273A Heavy | QVQLVQSGAEVKKPGASVKISCKASGYDFTSFPMHWVRLGPGQRLEWMGWIS AANGNTKYSQKFQDRFTITRDTSASIVHMELSSLRSEDTAVYYCARGGYSSGLYRY SNYYYGMTVWGQGTLVTVSS | 231 |
| NORO-273A Light | DIVMTQTPLSLSVTPGQPASISCKSSESLLHNDRKTYLFWYLQKPGQPPQLLIFQV SNRFSGVPDRFSGSGSGTDFTLRISRVEAEDVGIYYCLQTTQLPLTFGGGTKVEIK | 232 |
| NORO-316 Heavy | Not available | 233 |
| NORO-316 Light | Not available | 234 |
| NORO-318 Heavy | Not available | 235 |
| NORO-318 Light | DIVMTQSPLSLPVTPGEPASISCRSSQSLLHSDGLNYLDWYLLKPGQPPQLLIYLAS NRASGAPDRFSGSGSGTDFTLTISRVEAEDVGIYYCMEALQTPPTFGGGTKVEIK | 236 |
| NORO-327A Heavy | Not available | 237 |
| NORO-327A Light | QSVLTQSPSVSGAPGQRVTISCTGTSSNIGAGYDVHWYQQFPGTAPKLLISHNTN RPSGVPDRFSGSKSGTSASLAITGLQAEDEADYYCQSFDSSLRGSRVFGGGTKLTV L | 238 |
| NORO-156.3 Heavy | QVQLQQWGAGLLKPSETLSLTCAVYGGSFSGYYWSWIRQPPGKGLEWIGEINHS GSTNYNPSLKSRVTISVDTSKNQFSLKLSSVTAADTAVYYCARGLMDVWGQGTL VTVSS | 298 |
| NORO-156.3 Light | AIRMTQSPSSFSASTGDRVTITCRASQGISSYLAWYQQKPGKAPKLLIYAASTLQS GVPSRFSGSGSGTDFTLTISCLQSEDFATYYCQQYYSYPRTFGQGTKLEIK | 299 |
| NORO-168.2 Heavy | QVQLVESGGGVVQPGRSLRLSCAASGFTFSSYAMHWVRQAPGKGLEWVAVISY DGSNKYYADSVKGRFTISRDNSKNTLYLQMNSLRAEDTAVYYCARSVIGYYYGM DVWGQGTLVTVSS | 300 |
| NORO-168.2 Light | QPVLTQPPSASASLGASVTLTCTLSSGYSNYKVDWYQQRPGKGPRFVMRVGTG GIVGSKGDGIPDRFSVLGSGLNRYLTIKNIQEEDESDYHCGADHGSGILFGGGTKL TVL | 301 |
| NORO-178.6 Heavy | QVQLVESGGGVVQPGRSLRLSCAASGFTFSTYGMNWVRQAPGRGLEWVADISY DGSNSRYADSVKGRFTISRDNSKNTLSLQMNGLRTEDTAVYYCAKDWYLAMAG AAFDSWGPGTLVTVSS | 302 |
| NORO-178.6 Light | SSELTQDPVVSVALGQTVRITCQGDSLTTFYASWFQQKPGQAPALVLYGNDNRP SGIPDRFSGSRSGNTASLTITGAQAEDEADYYCNSRDSSGKPSFGGGTKLTVL | 303 |
| NORO-279A Heavy | QVQLVESGGGVVQPGRSLRLSCAASGFTFTKYGMHWVRQAPGKGLEWVAFIAY DGSVKYYGDSAKGRFAISRDNPKNTVYLQMNSLRAEDTAVYYCAKVEIHYYSNSL LGMDVWGQGTLVTVSS | 304 |
| NORO-279A Light | QSVLTQPPSASGTPGQRVTISCSGGNSNIGISYVYWYQHLPGTAPKLLISKNNLRP SGVPDRFSASKSGTSASLAISGLRSEDEAEYYCATLDINMTWVFGGGTKLTVL | 305 |
| NORO-323A Heavy | QVQLVESGGGVVQPGRSLRLSCAASGFTFSGSSLHWVRQAPGKGLEWVAAISY DGTNTYYADSVKGRFTLSRDNSKNTLYLQMNSLRAEDTAVYYCAKPVLSPFDYW GQGTLVTVSS | 306 |

TABLE 2-continued

PROTEIN SEQUENCES FOR ANTIBODY VARIABLE REGIONS

| Clone | Variable Sequence | SEQ ID NO. |
|---|---|---|
| NORO-323A Light | QSALTQPASVSGSPGQSITISCTGTSSDVGGYNYVSWYQQHPGKAPKLLIYEVSN RPSGVSRRFSGSKSGNTASLTISGLQAEDEADYYCCSYTSSSTEVFGGGTKLTVL | 307 |

TABLE 3

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| NORO-115 | GITISGYY (69) | INTSGRTI (70) | ARDRLPASGSHWFHP (71) |
| NORO-123 | GFTFSQYP (72) | ISYDGMNK (73) | ARVTGDCTGNRCSYWAYYYYGLDV (74) |
| NORO-202A.1 | EYTFTGYY (75) | INPSGGT (76) | ARDLLRNWGDHDAFDV (77) |
| NORO-250B | GFTFSDYY (78) | ISGIMSST (79) | ARATSQGATSYYFDS (80) |
| NORO-251A | GFTFRSYG (81) | ISYDGSSK (82) | AKVRLTSYSIGWFSFDY (83) |
| NORO-256A | GFTFRSYG (84) | ISYDGGSK (85) | AKDFLRVYSYGWHSFDI (86) |
| NORO-278 | GFTFSSYG (87) | ISYDGSNK (88) | AKVTIIAAADLLDY (89) |
| NORO-279A | GFTFTKYG (90) | IAYDGSVK (91) | AKVEIHYYSNSLLGMDV (92) |
| NORO-296A | GFTFSEYY (93) | ITSSFSST (94) | ARYGAEYGSRSFYFLD (95) |
| NORO-303 | GFIFSSYA (96) | MSYDGNNK (97) | ARDCRVGWVFTYGMDV (98) |
| NORO-310A | GFSVSDNY (99) | IYSGGTT (100) | TRDPSQYYDSRGHYYQTFTPSFDS (101) |
| NORO-312A | GFTFSDSY (102) | ISGIMSST (103) | ARDAQYCSGGRCYLVFDY (104) |
| NORO-313.1 | GFTFSDFY (105) | ISSIAGAT (106) | ARMGRLELERRPHYYYPLDV (107) |
| NORO-315B | GFTFSDYY (108) | ISAIGGYT (109) | AREDCHGTSCYSGD (110) |
| NORO-317 | GFTFSDYY (111) | ISAINSYT (112) | ARDVGGSVRYSSNSNKKSYNYFDP (113) |
| NORO-320 | GGTVSSYA (114) | IIPIFDTT (115) | ARDRVPSYSPSRRFSTKGAMWGKYGMDV (116) |
| NORO-329A | GFTFSDYY (117) | ISSSFGST (118) | ARYNYYGSGSFVFDY (119) |
| NORO-118 | GFTFSGHG (239) | ISYDGSNK (240) | ARDGYRNLVLVGWYFDL (241) |
| NORO-232 | Not available (242) | Not available (243) | Not available (245) |
| NORO-246A | Not available (246) | Not available (247) | Not available (248) |

TABLE 3-continued

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| NORO-263 | GFTLSDYY (249) | ISSSHTST (250) | ARDWVGGRSAYSDH (251) |
| NORO-273A | GYDFTSFP (252) | ISAANGNT (253) | ARGGYSSGLYRYSNYYYGMTV (254) |
| NORO-316 | Not available (255) | Not available (256) | Not available (257) |
| NORO-318 | Not available (258) | Not available (259) | Not available (260) |
| NORO-327A | Not available (261) | Not available (262) | Not available (263) |
| NORO-156.3 | GGSFSGYY (308) | INHSGST (309) | ARGLMDV (310) |
| NORO-168.2 | GFTFSSYA (311) | ISYDGSNK (312) | ARSVIGYYYYGMDV (313) |
| NORO-178.6 | GFTFSTYG (314) | ISYDGSNS (315) | AKDWYLAMAGAAFDS (316) |
| NORO-279A | GFTFTKYG (317) | IAYDGSVK (318) | AKVEIHYYSNSLLGMD (319) |
| NORO-323A | GFTFSGSS (320) | ISYDGTNT (321) | AKPVLSPFDY (322) |

TABLE 4

CDR LIGHT CHAIN SEQUENCES

| Antibody | CDRH1 (SEQ ID NO:) | CDRH2 (SEQ ID NO:) | CDRH3 (SEQ ID NO:) |
|---|---|---|---|
| NORO-115 | QSVLYTSDNKNY (120) | WAS (121) | QQYYNSPLA (122) |
| NORO-123 | SSDVGGYKY (123) | EVT (124) | GSYAGSTTSGYV (125) |
| NORO-202A.1 | SSNIGSNF (126) | KNN (127) | SAWDDSLSGPV (128) |
| NORO-250B | SSNIGADYD (129) | ADI (130) | QSYDRSVSGSAV (131) |
| NORO-251A | SSNIANYY (132) | DNN (133) | GTWDTSLSAWV (134) |
| NORO-256A | SSNIGTYY (135) | DND (136) | GTWDLSLTAGWV (137) |
| NORO-278 | SSNIGAGYD (138) | GNS (139) | QSYDSSLSGPVV (140) |
| NORO-279A | NSNIGISY (141) | KNN (142) | ATLDINMTWV (143) |
| NORO-296A | SSNIGAGYD (144) | DNN (145) | QSYDSRLSSNVV (146) |
| NORO-303 | SSDVGGYNY (147) | EIS (148) | SSYAGTYNCVV (149) |
| NORO-310A | QDISDY (150) | AAS (151) | LQHDTYPLT (152) |
| NORO-312A | SSNIGAGYE (153) | GNN (154) | QSYDNRLRV (155) |
| NORO-313.1 | QSLLHSNGYNY (156) | LGS (157) | MQALQTRT (158) |
| NORO-315B | SSNIGAGYD (159) | HNT (160) | QSYDRSLSKSRV (161) |
| NORO-317 | VLSKEF (162) | KDN (163) | QSVDTRGTYKV (164) |
| NORO-320 | QSLLHSNGYNY (165) | LGS (166) | MQALQTPRT (167) |
| NORO-329A | SSNIGSNT (168) | SND (169) | AAWDDSLNGWV (170) |
| NORO-118 | Not available (264) | Not available (265) | Not available (266) |
| NORO-232 | QAVSTTY (267) | GTY (268) | QQYSSSPYT (269) |
| NORO-246A | ALANQY (270) | KDS (271) | QSADSTGIYKV (272) |
| NORO-263 | ALPRRP (273) | DDS (274) | YSTDSSGKERV (275) |
| NORO-273A | ESLLHNDRKTY (276) | QVS (277) | LQTTQLPLT (278) |
| NORO-316 | Not available (279) | Not available (280) | Not available (281) |

TABLE 4-continued

CDR LIGHT CHAIN SEQUENCES

| Antibody | CDRH1 (SEQ ID NO:) | CDRH2 (SEQ ID NO:) | CDRH3 (SEQ ID NO:) |
|---|---|---|---|
| NORO-318 | QSLLHSDGLNY (282) | LAS (283) | MEALQTPPT (284) |
| NORO-327A | SSNIGAGYD (285) | HNT (286) | QSFDSSLRGSRV (287) |
| NORO-156.3 | QGISSY (323) | AAS (324) | QQYYSYPRT (325) |
| NORO-168.2 | SGYSNYK (326) | VGTGGIVG (327) | GADHGSGIL (328) |
| NORO-178.6 | SLTTFY (329) | GND (330) | NSRDSSGKPS (331) |
| NORO-279A | NSNIGISY (332) | KNN (333) | ATLDINMTWV (334) |
| NORO-323A | SSDVGGYNY (335) | EVS (336) | CSYTSSSTEV (337) |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
Atmar et al., *Curr Opin Infect Dis.*, 2018.
"Antibodies: A Laboratory Manual," Cold Spring Harbor Press, Cold Spring Harbor, NY, 1988.
Abbondanzo et al., *Am. J. Pediatr. Hematol. Oncol.*, 12(4), 480-489, 1990.
Allred et al., *Arch. Surg.*, 125(1), 107-113, 1990.
Atherton et al., *Biol. of Reproduction*, 32, 155-171, 1985.
Barzon et al., *Euro Surveill.* 2016 Aug. 11; 21(32).
Beltramello et al., *Cell Host Microbe* 8, 271-283, 2010.
Brown et al., *J. Immunol. Meth.*, 12; 130(1), 111-121, 1990.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.*, 74(2):425-433, 1977.
De Jager et al., *Semin. Nucl. Med.* 23(2), 165-179, 1993.
Dholakia et al., *J. Biol. Chem.*, 264, 20638-20642, 1989.
Diamond et al., *J Virol* 77, 2578-2586, 2003.
Doolittle and Ben-Zeev, *Methods Mol. Biol.*, 109, 215-237, 1999.
Duffy et al., *N. Engl. J. Med.* 360, 2536-2543, 2009.
Elder et al. Infections, infertility and assisted reproduction. Part II: Infections in reproductive medicine & Part III: Infections and the assisted reproductive laboratory. Cambridge UK: Cambridge University Press; 2005.
Gefter et al., *Somatic Cell Genet.*, 3:231-236, 1977.
Gornet et al., *Semin Reprod Med.* 2016 September; 34(5): 285-292. Epub 2016 Sep. 14.
Gulbis and Galand, *Hum. Pathol.* 24(12), 1271-1285, 1993.
Halfon et al., *PLoS ONE* 2010; 5 (5) e10569
Hessell et al., *Nature* 449, 101-4, 2007.
Khatoon et al., *Ann. of Neurology*, 26, 210-219, 1989.
King et al., *J. Biol. Chem.*, 269, 10210-10218, 1989.
Kohler and Milstein, *Eur. J. Immunol.*, 6, 511-519, 1976.
Kohler and Milstein, *Nature*, 256, 495-497, 1975.
Kyte and Doolittle, *J. Mol. Biol.*, 157(1):105-132, 1982.
Mansuy et al., *Lancet Infect Dis.* 2016 October; 16(10): 1106-7.
Nakamura et al., In: *Enzyme Immunoassays: Heterogeneous and Homogeneous Systems*, Chapter 27, 1987.
O'Shannessy et al., *J. Immun. Meth.*, 99, 153-161, 1987.
Persic et al., *Gene* 187:1, 1997 Potter and Haley, *Meth. Enzymol.*, 91, 613-633, 1983.
Purpura et al., *Lancet Infect Dis.* 2016 October; 16(10): 1107-8. Epub 2016 Sep. 19.
Remington's Pharmaceutical Sciences, 15th Ed., 3:624-652, 1990.
Tang et al., *J. Biol. Chem.*, 271:28324-28330, 1996.
Wawrzynczak & Thorpe, In: *Immunoconjugates, Antibody Conjugates In Radioimaging And Therapy Of Cancer*, Vogel (Ed.), NY, Oxford University Press, 28, 1987.
Yu et al., *J Immunol Methods* 336, 142-151, doi:10.1016/j.jim.2008.04.008, 2008.
Glass et al., *N Engl J Med* 361:1776-1785, 2009.
Fields et al., *Fields Virology*. Lippincott Williams & Wilkins; 2013.
Bok & Green, *N Engl J Med.* 367:2126-2132, 2012.
Vinjé J., *J Clin Microbiol* 53:373-381, 2015.
Jiang et al., *J Virol* 66:6527-6532, 1992.
Richardson et al., *Expert Rev Vaccines* 12:155-167, 2013.
Erdman et al., *J Clin Microbiol* 27:1417-1418, 1989.
Czako et al., *Clin Vaccine Immunol* 19:284-287, 2012.
Reeck et al., *J Infect Dis* 202:1212-1218, 2010.
Jones et al., *Science* 346:755-759, 2014.

Duizer et al., *J Gen Virol* 85:79-87, 2004.
Herbst-Kralovetz et al., *Emerging Infect Dis* 19:431-438, 2013.
Ettayebi et al., *Science* 353:1387-1393, 2016.
Costantini et al., *Emerging Infect Dis* 24:1453-1464, 2018.
Sapparapu et al., *PLoS Pathog* 12:e1005719, 2016.
Loisy et al., *J Virol Methods* 123:1-7, 2005.
Kageyama et al., *J Clin Microbiol* 41:1548-1557, 2003.
Green et al., *J Clin* Microbiol 31:2185-2191, 1993.
Iritani et al., *J Med Virol* 79:1187-1193, 2007.
Gray et al., *J Clin Microbiol* 32:3059-3063, 1994.
Atmar et al., *Clin Vaccine Immunol* 22:923-929, 2015.
Czako et al., *Clin Vaccine Immunol* 22:221-228, 2015.
Lindesmith et al., *PLoS Pathog* 8: e1002705, 2012a.
Choi J-M et al., *Proc Natl Acad Sci U.S.A.* 105:9175-9180, 2008.
Debbink et al., *J Virol* 86:1214-1226, 2012.
Lindesmith et al., *J Virol* 86:873-883, 2012b.
Lochridge et al., *J Gen Virol* 86:2799-2806, 2005.
Parra et al., *PLoS ONE* 8:e67592, 2013.
Karst & Baric, *J Virol* 89:5756-5759, 2015.
Huang et al., *Protein Eng Des Sel* 27:339-349, 2014.
Crawford et al., *Clin. Vaccine Immunol* 22:168-177, 2015.
Koromyslova et al., ed. *PLoS Pathog* 13:e1006636, 2017.
Smith & Crowe, *Microbiol Spectr* 3:AID-0027-2014, 2015.
Debbink et al., *J Infect Dis* 208:1877-1887, 2013.
Debbink et al., *Clin Infect Dis* 58:1746-1752, 2014.
El-Kamary et al., *J Infect Dis* 202:1649-1658, 2010.
Bernstein et al., *J Infect Dis* 211:870-878, 2015.
Tan et al., *J Virol* 85:753-764, 2011.
Ramirez et al., *Clin Immunol* 144:98-108, 2012.
Leroux-Roels et al., *J Infect Dis* 217:597-607, 2018.
Alvarado et al., *Gastroenterology* 155(6): 1898-1907, 2018.
Bartsch et al., *PLoS ONE* 11, e0151219, 2016.
Brochet et al., *Nucleic Acids Res.* 36, W503-W508, 2008.
Hale et al., *J. Medical Virol.*, 54(4), pp. 305-312, 1998.
Hall et al., A. J., Wikswo, M. E., Pringle, K., Gould, L. H., Parashar, U. D., Division of Viral Diseases, National Center for Immunization and Respiratory Diseases, CDC; United States, 2009-2012. MMWR Morb. Mortal. Wkly. Rep. 63, 491-495, 2014.
Knipe and Howley, Fields Virology (Lippincott Williams & Wilkins), 2013.
Koromyslova et al., *J. Virol.* 93, 1580, 2019.
Kou et al., *Clin. Vaccine Immunol.* 22, 160-167, 2015.
Laskowski and Swindells, *J. Chem. Inf. Model.*, 51, 2778-2786. [PubMed id: 21919503], 2011.
McCoy et al., *J. Appl. Cryst.* 40, 658-674, 2007.
McLean et al., *Mol. Immunol.* 37, 837-845, 2000.
Parker et al., *J. Virol.* 79, 7402-7409, 2005.
Parra et al., *J. Virol.* 86, 7414-7426, 2012.
Pettersen et al., *Comput Chem.* 25(13):1605-12, 2004.
Pires et al., *PLoS ONE* 10, e0142927, 2015.
Pletneva et al., *Virus Genes* 23, 5-16, 2001.
Prasad et al., *Science* 286, 287-290, 1999.
Shanker et al., *Proc Natl Acad Sci USA* 113(40):E5830-E5837 (Epub 2016 Sep. 19), 2016.
Shanker et al., *J. Virol.* 85(17): 8635-8645, 2011.
Tian et al., *J. Appl. Microbiol.* 109, 1753-1762, 2010.
Treanor et al., *J. Clin. Microbiol.* 31, 1630-1634, 1993.
Yoda et al., *J. Clin. Microbiol.* 41, 2367-2371, 2003.
Zheng et al., *J. Med. Virol.* 90, 671-676, 2018.

What is claimed is:

1. A method of detecting a norovirus infection in a subject comprising:
   (a) contacting a sample from said subject with an antibody or antigen binding fragment thereof comprising heavy chain CDR1-3 sequences comprising SEQ ID NOS: 114-116, and light chain CDR1-3 sequences comprising SEQ ID NOS: 165-167; and
   (b) detecting norovirus in said sample by binding of said antibody or antigen binding fragment thereof to a norovirus antigen in said sample.

2. A method of treating a subject infected with norovirus, or reducing the likelihood of infection of a subject at risk of contracting norovirus, comprising delivering to said subject an antibody or antigen binding fragment thereof comprising heavy chain CDR1-3 sequences comprising SEQ ID NOS: 114-116, and light chain CDR1-3 sequences comprising SEQ ID NOS: 165-167.

3. The method of claim 2, the antibody or antigen binding fragment thereof is encoded by heavy and light chain variable sequences comprising SEQ ID NOS: 31 and 32, respectively.

4. The method of claim 2, the antibody or antigen binding fragment thereof is encoded by heavy and light chain variable sequences having 95% identity to SEQ ID NOS: 31 and 32, respectively.

5. The method of claim 2, wherein said antigen binding fragment thereof is encoded by Previously presented heavy and light chain variable sequences having 70%, 80%, or 90% identity to SEQ ID NOS: 31 and 32, respectively.

6. The method of claim 2, wherein said antibody or antigen binding fragment thereof comprises heavy and light chain variable sequences comprising SEQ ID NOS: 65 and 66, respectively.

7. The method of claim 2, wherein said antibody or antigen binding fragment thereof comprises heavy and light chain variable sequences having 70%, 80% or 90% identity to SEQ ID NOS: 65 and 66, respectively.

8. The method of claim 2, wherein said antibody or antigen binding fragment thereof comprises heavy and light chain variable sequences having 95% identity to SEQ ID NOS: 65 and 66, respectively.

9. The method of claim 2, wherein the antigen binding fragment is a recombinant scFv (single chain fragment variable) antibody, Fab fragment, F(ab')$_2$ fragment, or Fv fragment.

10. The method of claim 2, wherein said antibody is an IgG, or a recombinant IgG antibody or antigen binding fragment thereof comprising an Fc portion mutated to alter FcR interactions, to increase half-life and/or increase therapeutic efficacy, or glycan modified to alter FcR interactions.

11. The method of claim 2, wherein said antibody is a chimeric antibody or a bispecific antibody.

12. The method of claim 2, wherein said antibody or antigen binding fragment thereof is administered prior to infection or after infection.

13. The method of claim 2, wherein said subject is a pregnant female, a sexually active female, or a female undergoing fertility treatments.

14. The method of claim 2, wherein delivering comprises antibody or antigen binding fragment thereof administration, or genetic delivery with an RNA or DNA sequence or vector encoding the antibody or antigen binding fragment thereof.

15. A monoclonal antibody or antigen binding fragment thereof, wherein the antibody or antigen binding fragment thereof comprising heavy chain CDR1-3 sequences comprising SEQ ID NOS: 114-116, and light chain CDR1-3 sequences comprising SEQ ID NOS: 165-167, wherein said antibody or antigen binding fragment thereof comprises an Fc portion mutated to eliminate or enhance FcR interactions to increase half-life and/or increase therapeutic efficacy or glycan modified to eliminate or enhance FcR interactions.

16. A hybridoma or engineered cell encoding an antibody or antigen binding fragment thereof wherein the antibody or antigen binding fragment thereof comprising heavy chain CDR1-3 sequences comprising SEQ ID NOS: 114-116, and light chain CDR1-3 sequences comprising SEQ ID NOS: 165-167.

17. A vaccine formulation comprising one or more antibodies or antibody fragments characterized by a first antibody or antigen binding fragment thereof according to claim 15.

18. A vaccine formulation comprising one or more expression vectors encoding a first antibody or antigen binding fragment thereof according to claim 15.

19. The antibody or antibody antigen binding thereof of claim 15, wherein:
   wherein the Fc portion mutated to eliminate or enhance FcR interactions comprises a mutation selected from a LALA, N297, GASD/ALIE, YTE and a LS mutation; or
   wherein the glycan modified antibody or antigen binding fragment thereof has an enzymatic addition, a chemical addition, has removal of glycans or is expressed in a cell line engineered with a defined glycosylating pattern.

20. The method of claim 1, wherein said antibody or antigen binding fragment thereof comprises heavy and light chain variable sequences comprising SEQ ID NOS: 65 and 66, respectively.

21. The monoclonal antibody or antigen binding fragment thereof of claim 15, wherein said antibody or antigen binding fragment thereof comprises heavy and light chain variable sequences comprising SEQ ID NOS: 65 and 66, respectively.

* * * * *